United States Patent
Shitara et al.

(10) Patent No.: US 7,939,077 B2
(45) Date of Patent: *May 10, 2011

(54) HUMANIZED ANTIBODY AGAINST FIBROBLAST GROWTH FACTOR-8 AND ANTIBODY FRAGMENT THEREOF

(75) Inventors: Kenya Shitara, Machida (JP); Kazuyasu Nakamura, Machida (JP); Maiko Hirota, Tokyo (JP); Naoki Shimada, Machida (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 1148 days.

This patent is subject to a terminal disclaimer.

(21) Appl. No.: 10/482,105

(22) PCT Filed: Jun. 28, 2002

(86) PCT No.: PCT/JP02/06591
§ 371 (c)(1), (2), (4) Date: May 19, 2004

(87) PCT Pub. No.: WO03/002608
PCT Pub. Date: Jan. 9, 2003

(65) Prior Publication Data
US 2004/0253234 A1 Dec. 16, 2004

(30) Foreign Application Priority Data
Jun. 28, 2001 (JP) .............................. P. 2001-196176

(51) Int. Cl.
*A61K 39/395* (2006.01)
*C07H 21/04* (2006.01)
*C07K 16/22* (2006.01)
*C12N 5/10* (2006.01)
*C12N 15/13* (2006.01)
*C12N 15/63* (2006.01)
*C12P 21/08* (2006.01)

(52) U.S. Cl. ................ 424/145.1; 424/138.1; 424/139.1; 424/142.1; 424/155.1; 435/7.23; 435/69.1; 435/70.1; 435/70.21; 435/320.1; 435/330; 435/336; 436/548; 436/64; 530/387.3; 530/387.7; 530/388.24; 536/25.53

(58) Field of Classification Search ................ 424/138.1, 424/139.1, 142.1, 145.1, 155.1; 435/7.23, 435/69.1, 70.1, 70.21, 320.1, 330, 336; 436/518, 436/536, 548, 64; 530/387.3, 387.7, 388.24; 536/23.53
See application file for complete search history.

(56) References Cited

U.S. PATENT DOCUMENTS
5,225,539 A    7/1993 Winter ........................ 530/387.3
(Continued)

FOREIGN PATENT DOCUMENTS
EP    0 799 835 A2 * 10/1997
(Continued)

OTHER PUBLICATIONS
Owens et al., 1994. The genetic engineering of monoclonal antibodies. Journal of Immunological Methods 168: 149-165.*
(Continued)

*Primary Examiner* — Shafiqul Haq
*Assistant Examiner* — James L Grun
(74) *Attorney, Agent, or Firm* — Nixon & Vanderhye, P.C.

(57) ABSTRACT

The present invention relates to an antibody against FGF-8, particularly a humanized antibody against FGF-8 and the antibody fragment thereof, a DNA sequence encoding the above antibody or the antibody fragment, a vector comprising the DNA sequence and a host cell transformed by the vector, a production process of the above antibody or the antibody fragment using the host cell, and a therapeutic agent and a diagnostic agent for cancer using the antibody or the antibody fragment.

8 Claims, 16 Drawing Sheets

U.S. PATENT DOCUMENTS

| | | | |
|---|---|---|---|
| 5,585,089 A | 12/1996 | Queen et al. | 424/133.1 |
| 5,693,761 A | 12/1997 | Queen et al. | 536/23.53 |
| 5,693,762 A | 12/1997 | Queen et al. | 530/387.3 |
| 5,952,472 A | 9/1999 | Hanai et al. | 530/387.1 |
| 6,180,370 B1 | 1/2001 | Queen et al. | 435/69.6 |
| 6,310,184 B1 | 10/2001 | Hanai et al. | 530/387.1 |
| 6,331,415 B1 | 12/2001 | Cabilly et al. | 435/69.6 |

FOREIGN PATENT DOCUMENTS

| | | | |
|---|---|---|---|
| EP | 0 882 794 A2 | | 12/1998 |
| JP | 2001-46066 | | 2/2001 |
| WO | 92/12734 | * | 8/1992 |

OTHER PUBLICATIONS

Tanaka et al, Cancer Research, May 15, 1998, vol. 58, No. 10, pp. 2053-2056.

Vaughan et al, Nature Biotechnology, Jun. 1998, vol. 16, No. 6, pp. 535-539.

Lorenzi et al, Expression cloning, developmental expression and chromosomal localization of fibroblast growth factor-8, Oncogene (1995), vol. 10, pp. 2051-2055.

Jones et al, Nature, vol. 321, May 29, 1986, pp. 522-525.

Riechmann et al, Nature, vol. 332, Mar. 24, 1988, pp. 323-327.

Gnanapragasam et al "FGF8 isoform b expression in human prostate cancer", British Journal of Cancer (2003) 88, 1432-1438.

Morrison et al "Chimeric human antibody molecules: Mouse antigen-binding domains with human constant region domains", Proc. Natl. Acad. Sci., Nov. 1984, vol. 81, pp. 6851-6855.

Kettleborough et al, "Humanization of a mouse monoclonal antibody by CDR-grafting: the importance of framework residues on loop conformation", Protein Engineering, vol. 4, No. 7, pp. 773-783, 1991.

Canadian Office Action dated Mar. 6, 2009, issued in connection with Canadian Patent Application No. 2,451,854.

Rudikoff et al, "Single amino acid substitution altering antigen-binding specificity", Proc. Natl. Acad. Sci., vol. 79, pp. 1979-1983, Mar. 1982.

* cited by examiner

SEQUENCE LISTING

<160> NUMBER OF SEQ ID NOS: 41

<210> SEQ ID NO 1
<211> LENGTH: 420

```
<212> TYPE: DNA
<213> ORGANISM: Mus musculus
<220> FEATURE:
<221> NAME/KEY: CDS
<222> LOCATION: (1)..(420)

<400> SEQUENCE: 1 atg gaa tgg atc tgg atc ttt ctc ttc ttc ctc tca gga act aca ggt     48
Met Glu Trp Ile Trp Ile Phe Leu Phe Phe Leu Ser Gly Thr Thr Gly
 1               5                  10                  15 gtc tac tcc cag gtt cag ctg cag cag tct gga gct gag gtg gcg agg     96
Val Tyr Ser Gln Val Gln Leu Gln Gln Ser Gly Ala Glu Val Ala Arg
             20                  25                  30 ccc ggg gct tca gtg aaa ctg tcc tgc aag gct tct ggc tac acc ttc    144
Pro Gly Ala Ser Val Lys Leu Ser Cys Lys Ala Ser Gly Tyr Thr Phe
         35                  40                  45 act gac tac tat cta aac tgg gtg aag cag agg tct gga cag ggc ctt    192
Thr Asp Tyr Tyr Leu Asn Trp Val Lys Gln Arg Ser Gly Gln Gly Leu
     50                  55                  60 gag tgg att gga gag att gat cct gga agt gat agt ata tat tat aat    240
Glu Trp Ile Gly Glu Ile Asp Pro Gly Ser Asp Ser Ile Tyr Tyr Asn
 65                  70                  75                  80 gaa aac ttg gag ggc agg gcc aca ctg act gca gac aaa tcc tcc agc    288
Glu Asn Leu Glu Gly Arg Ala Thr Leu Thr Ala Asp Lys Ser Ser Ser
                 85                  90                  95 aca gcc tac atg cag ctc aac agc ctg aca tct gag gac tct gca gtc    336
Thr Ala Tyr Met Gln Leu Asn Ser Leu Thr Ser Glu Asp Ser Ala Val
            100                 105                 110 tat ttc tgt gca aga tat ggg tat tct aga tac gac gta agg ttt gtc    384
Tyr Phe Cys Ala Arg Tyr Gly Tyr Ser Arg Tyr Asp Val Arg Phe Val
        115                 120                 125 tac tgg ggc caa ggg act ctg gtc act gtc tct aca                    420
Tyr Trp Gly Gln Gly Thr Leu Val Thr Val Ser Thr
    130                 135                 140

<210> SEQ ID NO 2
<211> LENGTH: 140
<212> TYPE: PRT
<213> ORGANISM: Mus musculus

<400> SEQUENCE: 2

Met Glu Trp Ile Trp Ile Phe Leu Phe Phe Leu Ser Gly Thr Thr Gly
 1               5                  10                  15

Val Tyr Ser Gln Val Gln Leu Gln Gln Ser Gly Ala Glu Val Ala Arg
             20                  25                  30

Pro Gly Ala Ser Val Lys Leu Ser Cys Lys Ala Ser Gly Tyr Thr Phe
         35                  40                  45

Thr Asp Tyr Tyr Leu Asn Trp Val Lys Gln Arg Ser Gly Gln Gly Leu
     50                  55                  60

Glu Trp Ile Gly Glu Ile Asp Pro Gly Ser Asp Ser Ile Tyr Tyr Asn
 65                  70                  75                  80

Glu Asn Leu Glu Gly Arg Ala Thr Leu Thr Ala Asp Lys Ser Ser Ser
                 85                  90                  95

Thr Ala Tyr Met Gln Leu Asn Ser Leu Thr Ser Glu Asp Ser Ala Val
            100                 105                 110

Tyr Phe Cys Ala Arg Tyr Gly Tyr Ser Arg Tyr Asp Val Arg Phe Val
        115                 120                 125

Tyr Trp Gly Gln Gly Thr Leu Val Thr Val Ser Thr
    130                 135                 140
```

```
<210> SEQ ID NO 3
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 3 atg aag ttg cct gtt agg ctg ttg gtg ctg atg ttc tgg att cct gct      48
Met Lys Leu Pro Val Arg Leu Leu Val Leu Met Phe Trp Ile Pro Ala
  1               5                  10                  15 tcc agg agt gat gtt ttg atg acc caa act cca ctc tcc ctg cct gtc      96
Ser Arg Ser Asp Val Leu Met Thr Gln Thr Pro Leu Ser Leu Pro Val
             20                  25                  30 agt ctt gga gat caa gcc tcc atc tct tgc aga tct agt cag agt ctt     144
Ser Leu Gly Asp Gln Ala Ser Ile Ser Cys Arg Ser Ser Gln Ser Leu
         35                  40                  45 gta cat agt aat gga aga acc tat tta gaa tgg tac ctg cag aaa cct     192
Val His Ser Asn Gly Arg Thr Tyr Leu Glu Trp Tyr Leu Gln Lys Pro
     50                  55                  60 ggc cag tca cca aag gtc ctg atc tac aaa gtt tcc aac cga att tct     240
Gly Gln Ser Pro Lys Val Leu Ile Tyr Lys Val Ser Asn Arg Ile Ser
 65                  70                  75                  80 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
                 85                  90                  95 ctc aaa atc agc aga gtg gag gct gag gat ctg gga gtt tat ttc tgc     336
Leu Lys Ile Ser Arg Val Glu Ala Glu Asp Leu Gly Val Tyr Phe Cys
            100                 105                 110 ttt cag ggt tca cat gtt ccg tac acg ttc gga ggg ggg acc aag ctg     384
Phe Gln Gly Ser His Val Pro Tyr Thr Phe Gly Gly Gly Thr Lys Leu
        115                 120                 125 gaa ata aaa                                                          393
Glu Ile Lys
    130

<210> SEQ ID NO 4
<211> LENGTH: 131
<212> TYPE: PRT
<213> ORGANISM: Mus musculus

<400> SEQUENCE: 4

Met Lys Leu Pro Val Arg Leu Leu Val Leu Met Phe Trp Ile Pro Ala
  1               5                  10                  15

Ser Arg Ser Asp Val Leu Met Thr Gln Thr Pro Leu Ser Leu Pro Val
             20                  25                  30

Ser Leu Gly Asp Gln Ala Ser Ile Ser Cys Arg Ser Ser Gln Ser Leu
         35                  40                  45

Val His Ser Asn Gly Arg Thr Tyr Leu Glu Trp Tyr Leu Gln Lys Pro
     50                  55                  60

Gly Gln Ser Pro Lys Val Leu Ile Tyr Lys Val Ser Asn Arg Ile Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Phe Gln Gly Ser His Val Pro Tyr Thr Phe Gly Gly Gly Thr Lys Leu
        115                 120                 125

Glu Ile Lys
    130
```

```
<210> SEQ ID NO 5
<211> LENGTH: 5
<212> TYPE: PRT
<213> ORGANISM: Mus musculus

<400> SEQUENCE: 5

Asp Tyr Tyr Leu Asn
 1               5

<210> SEQ ID NO 6
<211> LENGTH: 17
<212> TYPE: PRT
<213> ORGANISM: Mus musculus

<400> SEQUENCE: 6

Glu Ile Asp Pro Gly Ser Asp Ser Ile Tyr Tyr Asn Glu Asn Leu Glu
 1               5                  10                  15

Gly

<210> SEQ ID NO 7
<211> LENGTH: 12
<212> TYPE: PRT
<213> ORGANISM: Mus musculus

<400> SEQUENCE: 7

Tyr Gly Tyr Ser Arg Tyr Asp Val Arg Phe Val Tyr
 1               5                  10

<210> SEQ ID NO 8
<211> LENGTH: 16
<212> TYPE: PRT
<213> ORGANISM: Mus musculus

<400> SEQUENCE: 8

Arg Ser Ser Gln Ser Leu Val His Ser Asn Gly Arg Thr Tyr Leu Glu
 1               5                  10                  15

<210> SEQ ID NO 9
<211> LENGTH: 7
<212> TYPE: PRT
<213> ORGANISM: Mus musculus

<400> SEQUENCE: 9

Lys Val Ser Asn Arg Ile Ser
 1               5

<210> SEQ ID NO 10
<211> LENGTH: 9
<212> TYPE: PRT
<213> ORGANISM: Mus musculus

<400> SEQUENCE: 10

Phe Gln Gly Ser His Val Pro Tyr Thr
 1               5

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
```

-continued

```
ctgaattcgc ggccgctagt cc                                           22
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 12

```
atgggccctt ggtggaggct gtagagacag tgaccagag                         39
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13

```
ctgaattcgc ggccgctgct gt                                           22
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14

```
atcgtacgtt ttatttccag cttggtcc                                     28
```

<210> SEQ ID NO 15
<211> LENGTH: 25
<212> TYPE: PRT
<213> ORGANISM: Homo sapiens

<400> SEQUENCE: 15

```
Gln Val Thr Val Gln Ser Ser Pro Asn Phe Thr Gln His Val Arg Glu
 1               5                  10                  15

Gln Ser Leu Val Thr Asp Gln Leu Cys
            20                  25
```

<210> SEQ ID NO 16
<211> LENGTH: 121
<212> TYPE: PRT
<213> ORGANISM: Artificial Sequence
<220> FEATURE:
<223> OTHER INFORMATION: Description of Artificial Sequence: synthetic
      protein

<400> SEQUENCE: 16

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Glu Ile Asp Pro Gly Ser Asp Ser Ile Tyr Tyr Asn Glu Asn Leu
    50                  55                  60

Glu Gly Arg Val Thr Ile Thr Ala Asp Thr Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Ser
        115                 120
```

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: synthetic
      protein

<400> SEQUENCE: 17

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Leu Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
            100                 105                 110
```

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: synthetic
      protein

<400> SEQUENCE: 18

```
Gln Val Gln Leu Val Gln Ser Gly Ala Glu Val Ala Arg Pro Gly Ala
 1               5                  10                  15

Ser Val Lys Val Ser Cys Lys Ala Ser Gly Tyr Thr Phe Thr Asp Tyr
            20                  25                  30

Tyr Leu Asn Trp Val Arg Gln Arg Ser Gly Gln Gly Leu Glu Trp Ile
        35                  40                  45

Gly Glu Ile Asp Pro Gly Ser Asp Ser Ile Tyr Tyr Asn Glu Asn Leu
    50                  55                  60

Glu Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Ser
        115                 120
```

<210> SEQ ID NO 19
<211> LENGTH: 112

```
<212> TYPE: PRT
<213> ORGANISM: Artificial Sequence
<220> FEATURE:
<223> OTHER INFORMATION: Description of Artificial Sequence: synthetic
      protein

<400> SEQUENCE: 19

Asp Val Val Met Thr Gln Ser Pro Leu Ser Leu Pro Val Ser Leu Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Lys Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 20
<211> LENGTH: 141
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
caggaaacag ctatgacgaa ttcgcggccg cacactgact ctaaccatgg aatggatctg     60
gatctttctc ttcttcctct caggaactac aggtgtctac tcccaggtgc agctggtgca    120
gtctggggct gaggtgaaga a                                              141

<210> SEQ ID NO 21
<211> LENGTH: 141
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
aggatcgatc tctcccatcc actcaagccc ttgtccgggg gcctgccgca cccagtttag     60
atagtagtca gtgaaggtgt atccagaagc cttgcaggag accttcactg aggccccggg    120
cttcttcacc tcagccccag a                                              141

<210> SEQ ID NO 22
<211> LENGTH: 141
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
ggatgggaga gatcgatcct ggaagtgata gtatatatta taatgaaaac ttggagggca     60
gagtcacgat taccgcggac acatccacga gcacagccta catggagctg agcagcctga    120
gatctgagga cacggccgtg t                                              141
```

<210> SEQ ID NO 23
<211> LENGTH: 141
<212> TYPE: DNA
<213> ORGANISM: Artificial Sequence
<220> FEATURE:
<223> OTHER INFORMATION: Description of Artificial Sequence:synthetic DNA

<400> SEQUENCE: 23

```
gttttcccag tcacgactag tgggcccttg gtggaggctg aggagacggt gaccagggtt      60
ccctggcccc agtagacaaa ccttacgtcg tatctagaat acccatatct cgcacagtaa     120
tacacggccg tgtcctcaga t                                               141
```

<210> SEQ ID NO 24
<211> LENGTH: 141
<212> TYPE: DNA
<213> ORGANISM: Artificial Sequence
<220> FEATURE:
<223> OTHER INFORMATION: Description of Artificial Sequence:synthetic DNA

<400> SEQUENCE: 24

```
caggaaacag ctatgacgaa ttcgcggccg cacactgact ctaaccatgg aatggatctg      60
gatctttctc ttcttcctct caggaactac aggtgtctac tcccaggtgc agctggtgca     120
gtctggggct gaggtggcga g                                               141
```

<210> SEQ ID NO 25
<211> LENGTH: 141
<212> TYPE: DNA
<213> ORGANISM: Artificial Sequence
<220> FEATURE:
<223> OTHER INFORMATION: Description of Artificial Sequence:synthetic DNA

<400> SEQUENCE: 25

```
aggatcgatc tctccaatcc actcaagccc ttgtccagac ctctgccgca cccagtttag      60
atagtagtca gtgaaggtgt atccagaagc cttgcaggag accttcactg aggccccggg     120
cctcgccacc tcagccccag a                                               141
```

<210> SEQ ID NO 26
<211> LENGTH: 141
<212> TYPE: DNA
<213> ORGANISM: Artificial Sequence
<220> FEATURE:
<223> OTHER INFORMATION: Description of Artificial Sequence:synthetic DNA

<400> SEQUENCE: 26

```
ggattggaga gatcgatcct ggaagtgata gtatatatta taatgaaaac ttggagggca      60
gagtcacgat taccgcggac acatccacga gcacagccta catggagctg agcagcctga     120
gatctgagga cacggccgtg t                                               141
```

<210> SEQ ID NO 27
<211> LENGTH: 141
<212> TYPE: DNA
<213> ORGANISM: Artificial Sequence
<220> FEATURE:
<223> OTHER INFORMATION: Description of Artificial Sequence:synthetic DNA

<400> SEQUENCE: 27

```
gttttcccag tcacgactag tgggcccttg gtggaggctg aggagacggt gaccagggtt      60
```

```
ccctggcccc agtagacaaa ccttacgtcg tatctagaat acccatatct cgcacagaaa    120
tacacggccg tgtcctcaga t                                              141
```

<210> SEQ ID NO 28
<211> LENGTH: 130
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28

```
caggaaacag ctatgacgaa ttcaggttgc ctcctcaaaa tgaagttgcc tgttaggctg     60
ttggtgctga tgttctggat tcctgcttcc aggagtgata tcgtgatgac tcagtctcca    120
ctctccctgc                                                           130
```

<210> SEQ ID NO 29
<211> LENGTH: 130
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 29

```
agactggcct ggcttctgca ggtaccattc taaataggtt cttccattac tatgtacaag     60
actctgacta gatctgcagg agatggaggc cggctctcca ggggtgacgg gcagggagag    120
tggagactga                                                           130
```

<210> SEQ ID NO 30
<211> LENGTH: 130
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 30

```
tgcagaagcc aggccagtct ccacagctcc tgatctataa agtttccaac cgaatttctg     60
gggtcccaga caggttcagt ggcagtggat ccgggacaga tttcacactg aaaatcagca    120
gggtggaggc                                                           130
```

<210> SEQ ID NO 31
<211> LENGTH: 129
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 31

```
gttttcccag tcacgactag tcgtacgttt gatttccacc ttggtccctt ggccgaacgt     60
gtacggaaca tgtgaaccct gaaagcagta ataaaccccg acgtcctcag cctccaccct    120
gctgatttt                                                            129
```

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence:synthetic

DNA

<400> SEQUENCE: 32
caggaaacag ctatgacgaa ttcaggttgc ctcctcaaaa tgaagttgcc tgttaggctg     60
ttggtgctga tgttctggat tcctgcttcc aggagtgatg ttgtgatgac tcagtctcca    120
ctctccctgc                                                          130

<210> SEQ ID NO 33
<211> LENGTH: 130
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 33
agactggcct ggcttctgca ggtaccattc taaataggtt cttccattac tatgtacaag     60
actctgacta gatctgcagg agatggaggc cggctctcca agactgacgg gcagggagag    120
tggagactga                                                          130

<210> SEQ ID NO 34
<211> LENGTH: 130
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 34
tgcagaagcc aggccagtct ccaaaggtcc tgatctataa agtttccaac cgaatttctg     60
gggtcccaga caggttcagt ggcagtggat ccgggacaga tttcacactg aaaatcagca    120
gggtggaggc                                                          130

<210> SEQ ID NO 35
<211> LENGTH: 129
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 35
gttttcccag tcacgactag tcgtacgttt gatttccacc ttggtccctt ggccgaacgt     60
gtacggaaca tgtgaaccct gaaagcagaa ataaacccg acgtcctcag cctccaccct    120
gctgattt                                                            129

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 36
atggtacctg cagaagccag gccagtctcc acaggtcct                           39

<210> SEQ ID NO 37
<211> LENGTH: 39
<212> TYPE: DNA
<213> ORGANISM: Artificial Sequence
<220> FEATURE:

<223> OTHER INFORMATION: Description of Artificial Sequence:synthetic
      DNA

<400> SEQUENCE: 37
atggtacctg cagaagccag gccagtctcc acagctcct                           39

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: synthetic
      protein

<400> SEQUENCE: 38

Asp Ile Val Met Thr Gln Ser Pro Leu Ser Leu Pro Val Ser Leu Gly
1               5                   10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: Description of Artificial Sequence: synthetic
      protein

<400> SEQUENCE: 39

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 40
<211> LENGTH: 121
<212> TYPE: PRT
<213> ORGANISM: Mus musculus

<400> SEQUENCE: 40

Gln Val Gln Leu Gln Gln Ser Gly Ala Glu Val Ala Arg Pro Gly Ala

```
                 1               5                  10                 15
Ser Val Lys Leu Ser Cys Lys Ala Ser Gly Tyr Thr Phe Thr Asp Tyr
                    20                  25                  30

Tyr Leu Asn Trp Val Lys Gln Arg Ser Gly Gln Gly Leu Glu Trp Ile
                35                  40                  45

Gly Glu Ile Asp Pro Gly Ser Asp Ser Ile Tyr Tyr Asn Glu Asn Leu
    50                  55                  60

Glu Gly Arg Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Tyr Gly Tyr Ser Arg Tyr Asp Val Arg Phe Val Tyr Trp Gly
                100                 105                 110

Gln Gly Thr Leu Val Thr Val Ser Thr
                115                 120

<210> SEQ ID NO 41
<211> LENGTH: 112
<212> TYPE: PRT
<213> ORGANISM: Mus musculus

<400> SEQUENCE: 41

Asp Val Leu Met Thr Gln Thr Pro Leu Ser Leu Pro Val Ser Leu Gly
  1               5                  10                 15

Asp Gln Ala Ser Ile Ser Cys Arg Ser Ser Gln Ser Leu Val His Ser
                20                  25                  30

Asn Gly Arg Thr Tyr Leu Glu Trp Tyr Leu Gln Lys Pro Gly Gln Ser
                35                  40                  45

Pro Lys Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Tyr Thr Phe Gly Gly Gly Thr Lys Leu Glu Ile Lys
                100                 105                 110
```

US 7,939,077 B2

HUMANIZED ANTIBODY AGAINST FIBROBLAST GROWTH FACTOR-8 AND ANTIBODY FRAGMENT THEREOF

This application is the U.S. national phase of international application PCT/JP02/06591 filed 28 Jun. 2002, which designated the U.S. PCT/JP02/05691 claims priority to JP Application No. 2001-196176 filed 28 Jun. 2001. The entire contents of these applications are incorporated herein by reference.

TECHNICAL FIELD

The present invention relates to an antibody against FGF-8, particularly a humanized antibody against FGF-8 and the antibody fragment thereof. Moreover, the present invention relates to a DNA sequence encoding the above antibody or the antibody fragment. The present invention relates to a vector comprising the DNA sequence and a host cell transformed by the vector. Moreover, the present invention relates to a production process of the above antibody or the antibody fragment using the host cell, and a therapeutic agent and a diagnostic agent for cancer using the antibody or the antibody fragment.

BACKGROUND ART

Androgen induced growth factor (AIGF) is a factor isolated in 1992 from a culture supernatant of a mouse mammary tumor cell line SC-3 [*J. Steroid Biochem.*, 27 459 (1987)] which shows sex hormone-dependent growth. AIGF is a growth factor which is induced and produced by androgen stimulation and activates growth of SC-3 cells in an autocrine manner [*Proc. Natl. Acad. Sci.*, 89, 8928-8932, (1992)]. As a result of gene cloning, it was found that it has a homology of 30 to 40% with fibroblast growth factor (FGF) family at the amino acid sequence, and it was named FGF-8. Thereafter, human FGF-8 gene was cloned from a human placenta genomic library using mouse FGF-8 gene as a probe, and it was shown that it coincided with the mouse FGF-8 at 85% in the nucleotide sequence and at 100% in the amino acid sequence [*FEBS Letters*, 363, 226 (1995)]. It has been assumed that sex hormone induced growth factors would play an autocrine role in cancers such as prostate cancer and breast cancer which show sex hormone-dependent growth, and the finding of FGF-8, though in a mouse system, was the first evidence of such a mechanism. It has been assumed that FGF-8 may also relate to generation and growth of cancers in human by a similar mechanism, but the it has not been demonstrated. However, it was reported that when FGF-8 was added, growth of certain human prostate cancer cell line was accelerated [*FEBS Letters*, 363, 226 (1995)], expression of mRNA in various human cancer cell lines such as prostate cancer, breast cancer and ovarian cancer was confirmed [*Cell Growth & Differ.*, 7, 1425 (1996), *Oncogene*, 18, 1053 (1999), *Int. J Cancer*, 88, 718 (2000)] and FGF-8s presented in human cancer tissues of prostate cancer, breast cancer and ovarian cancer was over-expressed compared to FGF-8s presented in normal tissues [*Cancer Res.*, 58, 2053, *Oncogene*, 18, 2755 (1999), *Oncogene*, 18, 1053 (1999), *Int. J. Cancer*, 88, 718 (2000)]. Thus, such a possibility has been pointed out that FGF-8 also plays an autocrine and paracrine role on the sex hormone-dependent growth of cancer cells in human. On the other hand, since high frequency expression of FGF-8 has also been observed in various hormone-independent human prostate cancer cells, prostate cancer tissues and breast cancer cells [*Cell Growth & Differ.*, 7, 1425 (1996), *Oncogene*, 18, 2755 (1999), *Oncogene*, 18, 1053 (1999)], there is a high possibility that expression of FGF-8 is controlled by sex hormone independent fashion. Furthermore, since there is a report that antisense DNA for FGF-8 inhibited in vitro and in vivo growth of a hormone-independent prostate cancer cell line [*Oncogene*, 16, 1487 (1998)], the presence of an FGF-8-dependent growth mechanism is also suggested in cancers which lost hormone-dependency.

Based on these facts, antibodies against FGF-8 are effective in analyzing biological function of FGF-8 for cancer cells and also in diagnosing cancer cells such as prostate cancer and breast cancer using an immunological detection method. Furthermore, in neutralizing antibodies which inhibits functions of FGF-8, it is expected that they are useful for analyzing the biological function of FGF-8, diagnosing cancers such as prostate cancer, breast cancer and ovarian cancer and treating sex hormone-dependent cancers and sex hormone-independent cancers. Thus, the inventors of the present invention conducted preparation of an antibody against FGF-8, and as a result, succeeded in preparing a mouse monoclonal antibody KM1334 which specifically reacts with FGF-8 and inhibits the function of FGF-8 (Japanese Published Unexamined Patent Application No. 271391/97).

It is known in general that when an antibody derived from a non-human animal, e.g., a mouse antibody, is administered to human, it is recognized as an foreign substance and induces a human antibody against the mouse antibody (human anti-mouse antibody hereinafter referred to as "HAMA") in the human body. It is known that the HAMA reacts with the administered mouse antibody to cause side effects [*J. Clin. Oncol.*, 2, 881 (1984), *Blood*, 65, 1349 (1985), *J. Natl. Cancer Inst.*, 80 932 (1988), *Proc. Natl. Acad. Sci. U.S.A.*, 82, 1242 (1985)], to quicken disappearance of the administered mouse antibody from the body [*J. Nucl. Med.*, 26, 1011 (1985), *Blood*, 65, 1349 (1985), *J. Natl. Cancer Inst.*, 80, 937 (1988)], and to reduce therapeutic effects of the mouse antibody [*J. Immunol.*, 135, 1530 (1985), *Cancer Res.*, 46, 6489 (1986)].

In order to solve these problems, attempts have been made to convert an antibody derived from a non-human animal into a humanized antibody such as a human chimeric antibody or a human CDR-grafted antibody using genetic engineering technique.

The human chimeric antibody consists of an antibody the V region derived from a non-human animal antibody and the C region derived from a human antibody [*Proc. Natl. Acad. Sci. U.S.A.*, 81, 6851 (1984)]. The human CDR-grafted antibody consists of the amino acid sequence of CDR in the V region derived from a non-human animal antibody is grafted into an appropriate position of a human antibody [*Nature*, 321, 522 (1986)]. In comparison with antibodies derived from non-human animals such as mouse antibodies and the like, these humanized antibodies have various advantages for clinical applications. For example, regarding immunogenicity and stability in blood, it has been reported that blood half-life of a human chimeric antibody became about 6 times as long as a mouse antibody when administered to human [*Proc. Natl. Acad. Sci. U.S.A.*, 86, 4220 (1989)]. In the case of a human CDR-grafted antibody, it has been reported that its immunogenicity was reduced and its serum half-life was prolonged in comparison with a mouse antibody in experiment using a monkey [*J. Immunol.*, 147, 1352 (1991)]. Thus, it is expected that the humanized antibodies have less side effects and their therapeutic effects continue for a longer time than antibodies derived from non-human animals.

Furthermore, since the human CDR-grafted antibody is prepared using genetic engineering technique, molecules in various forms can be prepared. For example, when the 1 subclass is used as an H chain C region (CH) of a human antibody, a humanized antibody having a high effector function such as antibody-dependent cell-mediated cytotoxic activity can be prepared [*Cancer Res.*, 56, 1118 (1996)]. A humanized antibody having a high effector function is quite effective when an antigen exists on the surface of cells such as cancer cells and destruction of the target cell is desired. On the other hand, in the case where only function which neutralizes the target molecule is required or in the case where side effects by the destruction of the target cell might be caused, the side effects can be avoided and a prolonged blood serum half-time in comparison with a mouse antibody is expected by using the 4 subclass as CH of the human antibody [*Immunol.*, 85, 668 (1995)] because the 4 subclass usually has a low effector function [*J. Exp. Med.*, 166, 1351 (1987), *J. Exp. Med.*, 168, 1351 (1998)]. Furthermore, according to the recent advances in protein engineering and genetic engineering, antibody fragments having a smaller molecular weight such as Fab, Fab', F(ab')$_2$, scFv [*Science*, 242, 423 (1988)], diabody [*Nature Biotechnol.*, 15, 629 (1997)], dsFv [*Molecular Immunol.*, 32, 249 (1995)] and a peptide containing CDR [*J. Biol. Chem.*, 271, 2966 (1996)] can be prepared as humanized antibodies. The antibody fragments are excellent in transitional activity into target tissue in comparison with complete antibody molecules [*Cancer Res.*, 52, 3402 (1992)].

It is considered that the humanized antibodies are more desirable than antibodies derived from non-human animals such as mouse antibodies, when used in clinical applications to human.

As discussed above, if humanized antibodies which specifically react with FGF-8 and inhibit function of FGF-8 or antibody fragments thereof are prepared, they are expected to be used as effective diagnostic agents or therapeutic agents for diseases relating to FGF-8 such as cancer. However, such antibodies or antibody fragments have not been prepared yet until now.

DISCLOSURE OF THE INVENTION

An object of the present invention is to provide a humanized antibody or the antibody fragment which specifically reacts with FGF-8 which is considered to be a growth factor of prostate cancer, breast cancer, ovarian cancer and the like and which further inhibits the biological function of FGF-8.

The inventors of the present invention obtained antibody H chain cDNA and L chain cDNA from a hybridoma KM1334 (FERM BP-5451) which produces a mouse antibody against FGF-8 belonging to IgG1 subclass, found that the V regions and CDRs were novel amino acid sequences, and expressed and purified an anti-FGF-8 human chimeric antibody and an anti-FGF-8 human CDR-grafted antibody by cloning cDNAs encoding the novel V regions or VH and VL comprising CDRs into an expression vector for animal cell comprising cDNAs encoding CH of a human antibody and L chain C region (CL) of a human antibody to thereby construct a vector for humanized antibody expression and then introducing the vector for expression antibody expression into an animal cell. Thus, the present invention has been accomplished.

(1) A humanized antibody which specifically reacts with fibroblast growth factor-8 (FGF-8) and inhibits biological function of FGF-8, or the antibody fragment thereof.

(2) The humanized antibody or the antibody fragment thereof according to (1), which comprises complementarity determining region (CDR) 1, CDR2 and CDR3 of an antibody heavy chain (H chain) variable region (V region) comprising the amino acid sequences represented by SEQ ID NOs:5, 6 and 7, respectively.

(3) The humanized antibody or the antibody fragment thereof according to (1), which comprises complementarity determining region (CDR) 1, CDR2 and CDR3 of an antibody light chain (L chain) variable region (V region) comprising the amino acid sequences represented by SEQ ID NOs:8, 9 and 10, respectively.

(4) The humanized antibody or the antibody fragment thereof according to any one of (1) to (3), which comprises CDR1, CDR2 and CDR3 of an antibody heavy chain (H chain) variable region (V region) comprising the amino acid sequences represented by SEQ ID NOs:5, 6 and 7, respectively, and CDR1, CDR2 and CDR3 of an antibody light chain (L chain) variable region (V region) comprising the amino acid sequences represented by SEQ ID NOs:8, 9 and 10, respectively.

(5) The antibody or the antibody fragment thereof according to any one of (1) to (4), wherein the humanized antibody is a human chimeric antibody or a human CDR-grafted antibody.

(6) The antibody or the antibody fragment thereof according to (5), wherein the human chimeric antibody comprises a heavy chain (H chain) variable region (V region) and a light chain (L chain) V region of a monoclonal antibody against FGF-8.

(7) The antibody or the antibody fragment thereof according to (5) or (6), wherein the human chimeric antibody comprises a heavy chain (H chain) variable region (V region) and a light chain (L chain) V region of a monoclonal antibody against FGF-8, and an H chain constant region (C region) and an L chain C region of a human antibody.

(8) The human chimeric antibody or the antibody fragment thereof according to any one of (5) to (7), wherein VH of the antibody comprises an amino acid sequence represented by SEQ ID NO:40.

(9) The human chimeric antibody or the antibody fragment thereof according to any one of (5) to (7), wherein VL of the antibody comprises an amino acid sequence represented by SEQ ID NO:41.

(10) The human chimeric antibody or the antibody fragment thereof according to any one of (5) to (7), wherein VH and VL of the antibody comprise amino acid sequences represented by SEQ ID NOs:40 and 41, respectively.

(11) The human chimeric antibody or the antibody fragment thereof according to any one of (5) to (7), which is KM3034 or KM3334, wherein VH and VL of the antibody comprise amino acid sequences represented by SEQ ID NOs:40 and 41, respectively.

(12) The antibody or the antibody fragment thereof according to (5), wherein the human CDR-grafted antibody comprises CDRs of VH and VL of a monoclonal antibody against FGF-8.

(13) The antibody or the antibody fragment thereof according to (5) or (12), wherein the human CDR-grafted antibody comprises CDRs of VH and VL of a monoclonal antibody against FGF-8, and framework regions (FRs) of VH and VL of a human antibody.

(14) The antibody or the antibody fragment thereof according to any one of (5), (12) and (13), wherein the human CDR-grafted antibody comprises CDRs of VH and VL of a monoclonal antibody against FGF-8, and an H chain C region and an L chain C region of a human antibody.

(15) The human CDR-grafted antibody or the antibody fragment thereof according to any one of (5) and (12) to (14), wherein CDR1, CDR2 and CDR3 of VH of the antibody comprise amino acid sequences represented by SEQ ID NOs: 5, 6 and 7, respectively.

(16) The human CDR-grafted antibody or the antibody fragment thereof according to any one of (5) and (12) to (14), wherein CDR1, CDR2 and CDR3 of VL of the antibody comprise amino acid sequences represented by SEQ ID NOs: 8, 9 and 10, respectively.

(17) The human CDR-grafted antibody or the antibody fragment thereof according to any one of (5) and (12) to (14), wherein CDR1, CDR2 and CDR3 of VH of the antibody comprises amino acid sequences represented by SEQ ID NOs:5, 6 and 7, respectively, and wherein CDR1, CDR2 and CDR3 of VL of the antibody comprises amino acid sequences represented by SEQ ID NOs:8, 9 and 10, respectively.

(18) The human CDR-grafted antibody or the antibody fragment thereof according to any one of (5) and (12) to (17), wherein VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:16 is substituted.

(19) The human CDR-grafted antibody or the antibody fragment thereof according to any one of (5) and (12) to (17), wherein VL of the antibody comprises an amino acid sequence in which at least one amino acid residue selected from Ile at position 2, Val at position 3, Thr at position 14, Pro at position 15, Gln at position 50, Leu at position 51 and Tyr at position 92 in the amino acid sequence represented by SEQ ID NO:17 is substituted.

(20) The human CDR-grafted antibody or the antibody fragment thereof according to any one of (5) and (12) to (17), wherein VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:16 is substituted, and wherein VL of the antibody comprises an amino acid sequence in which at least one amino acid residue selected from Ile at position 2, Val at position 3, Thr at position 14, Pro at position 15, Gln at position 50, Leu at position 51 and Tyr at position 92 in the amino acid sequence represented by SEQ ID NO:17 is substituted.

(21) The human CDR-grafted antibody or the antibody fragment thereof according to any one of (5) and (12) to (20), wherein VH of the antibody comprises the amino acid sequence represented by SEQ ID NO:16 or 18.

(22) The human CDR-grafted antibody or the antibody fragment thereof according to any one of (5) and (12) to (20), wherein VL of the antibody comprises the amino acid sequence represented by SEQ ID NO:17, 19, 38 or 39.

(23) The human CDR-grafted antibody or the antibody fragment thereof according to any one of (5) and (12) to (20), wherein VH of the antibody comprises the amino acid sequence represented by SEQ ID NO:16 or 18, and wherein VL of the antibody comprises the amino acid sequence represented by SEQ ID NO:17, 19, 38 or 39.

(24) The human CDR-grafted antibody or the antibody fragment thereof according to any one of (5) and (12) to (20), wherein VH and VL of the antibody comprise amino acid sequences represented by SEQ ID NOs:16 and 19, respectively.

(25) The human CDR-grafted antibody or the antibody fragment thereof according to any one of (5) and (12) to (20), wherein VH and VL of the antibody comprise amino acid sequences represented by SEQ ID NOs:16 and 38, respectively.

(26) The human CDR-grafted antibody or the antibody fragment thereof according to any one of (5) and (12) to (20), wherein VH and VL of the antibody comprise amino acid sequences represented by SEQ D NOs:16 and 39, respectively.

(27) The antibody fragment according to any one of (1) to (26), wherein the antibody fragment is selected from the group consisting of Fab, Fab', F(ab')$_2$, a single chain antibody (scFv), a dimerized variable region (V region) fragment (diabody), a disulfide-stabilized V region fragment (dsFv) and a peptide comprising a complementarity determining region (CDR).

(28) A DNA encoding the humanized antibody or the antibody fragment thereof according to any one of (1) to (27).

(29) A recombinant vector comprising the DNA according to (28).

(30) A transformant obtained by introducing the recombinant vector according to (29) into a host cell.

(31) A process for producing an antibody or the antibody fragment thereof, which comprises culturing the transformant according to (30) in a medium to prepare and accumulate the antibody or the antibody fragment thereof according to any one of (1) to (27) in the culture, and recovering the antibody or the antibody fragment thereof from the culture.

(32) A medicament which comprises, as an active ingredient, at least one selected from the antibody and the antibody fragment according to any one of (1) to (27).

(33) An agent for treating a cancer, which comprises, as an active ingredient, at least one selected from the antibody and the antibody fragment according to any one of claims 1 to 27.

(34) An agent for diagnosing a cancer, which comprises, as an active ingredient, at least one selected from the antibody and the antibody fragment according to any one of claims 1 to 27.

The present invention relates to a humanized antibody which specifically reacts with FGF-8 and inhibits biological function of FGF-8, or the antibody fragment thereof.

The biological function of FGF-8 includes sex hormone-dependent and -independent growth acceleration activity for various cancer cells such as prostate cancer, breast cancer and ovarian cancer [*Proc. Natl. Acad. Sci. U.S.A.*, 89, 8928 (1992)], vascularization function [*Oncogene*, 20, 2791 (2001)], and function in development of arthrosis [*Development*, 127, 2471 (2000), *Nature Genet.*, 26, 460 (2000)].

The humanized antibody includes a human chimeric antibody, a human CDR-grafted antibody and the like.

A human chimeric antibody is an antibody comprising VH and VL of an antibody derived from a non-human animal, and CH and CL of a human antibody. The non-human animal may be any of mouse, rat, hamster, rabbit and the like, so long as a hybridoma can be prepared therefrom.

The human chimeric antibody of the present invention can be produced by obtaining cDNAs encoding VH and VL from a hybridoma which produces a monoclonal antibody which reacts specifically with FGF8, inserting the cDNAs into an expression vector for animal cell, having genes encoding a human antibody CH and a human antibody CL to construct a vector for human chimeric antibody expression, and introducing the vector into an animal cell to express the antibody.

Any CH of a human chimeric antibody may be used, so long as it belongs to human immunoglobulin (hIg), and those of hIgG class are preferred, and any one of subclasses further belonging to hIgG such as γ1, γ2, γ3 and γ4 can be used. Also, any CL of a human chimeric antibody can be used, so long as it belongs to hIg, and those of κ class or λ class can be used.

The human chimeric antibody which specifically reacts with FGF-8 (anti-FGF8 chimeric antibody) includes a human chimeric antibody which comprises complementarity determining region (hereinafter referred to as "CDR") 1, CDR2 and CDR3 of an antibody heavy chain (H chain) variable region (V region) comprising the amino acid sequences represented by SEQ ID NOs:5, 6 and 7, respectively and/or comprises CDR1, CDR2 and CDR3 of an antibody light chain (L chain) variable region (V region) comprising the amino acid sequences represented by SEQ ID NOs:8, 9 and 10, respectively, and preferably a human chimeric antibody in which VH comprises the amino acid sequence represented by SEQ ID NO:40 and/or VL comprises the amino acid sequence represented by SEQ ID NO:41. Examples include antibody KM3034 in which VH of the antibody comprises the amino acid sequence represented by SEQ ID NO:40, CH of the human antibody comprises an amino acid sequence of γ1 subclass, VL of the antibody comprises the amino acid sequence represented by SEQ ID NO:41 and CL of the human antibody comprises an amino acid sequence of κ class.

A human CDR-grafted antibody is an antibody in which CDR amino acid sequences of VH and VL of an antibody derived from a non-human animal are grafted into appropriate positions of VH and VL of an human antibody.

The human CDR-grafted antibody of the present invention can be produced by grafting CDR sequences of VH and VL of an antibody which specifically reacts with FGF8 of a non-human animal into FRs in VH and VL of any human antibody to construct cDNAs encoding V regions obtained, inserting the cDNAs into an expression vector for animal cell, having DNAs encoding CH and CL of a human antibody to construct a vector for human CDR-grafted antibody expression, and then introducing it into an animal cell to express the antibody.

Any CH of human CDR-grafted antibody may be used, so long as it belongs to hIg, but those of hIgG class are preferred and any one of subclasses further belonging to hIgG such as γ1, γ2, γ3 and γ4 can be used Also, any CL of human CDR-grafted antibody may be used so long as it belongs to hIg, and those of κ class or λ class can be used.

The human CDR-grafted antibody which specifically reacts with FGF-8 (anti-FGF-8-CDR-grafted antibody) includes a human CDR-grafted antibody which comprises CDR1, CDR2 and CDR3 of an antibody VH comprising the amino acid sequences represented by SEQ ID NOs:5, 6 and 7, respectively and/or comprises CDR1, CDR2 and CDR3 of an antibody VL comprising the amino acid sequences represented by SEQ ID NOs:8, 9 and 10, respectively, preferably a human CDR-grafted antibody in which VH comprises the amino acid sequence represented by SEQ ID NO:16 and/or VL comprises the amino acid sequence represented by SEQ ID NO:17, and more preferably a human CDR-grafted antibody in which VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:16 is substituted with an other amino acid residue, a human CDR-grafted antibody in which VL of the antibody comprises an amino acid sequence in which at least one amino acid residue selected from Ile at position 2, Val at position 3, Thr at position 14, Pro at position 15, Gln at position 50, Leu at position 51 and Tyr at position 92 in the amino acid sequence represented by SEQ ID NO:17 is substituted with an other amino acid residue, and a human CDR-grafted antibody in which VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:16 is substituted with an other amino acid, and wherein VL of the antibody comprises an amino acid sequence in which at least one amino acid residue selected from Ile at position 2, Val at position 3, Thr at position 14, Pro at position 15, Gln at position 50, Leu at position 51 and Tyr at position 92 in the amino acid sequence represented by SEQ ID NO:17 is substituted with an other amino acid. Examples of VH include the amino acid sequence represented by SEQ ID NO:18 in which six residues of Lys at position 12, Lys at position 13, Ala at position 40, Pro at position 41, Met at position 48 and Tyr at position 95 in the amino acid sequence represented by SEQ ID NO:16 are modified with Ala, Arg, Arg, Ser, Ile and Phe, respectively. Examples of VL include the amino acid sequence represented by SEQ ID NO:19 in which six residues of Ile at position 2, Thr at position 14, Pro at position 15, Gln at position 50, Leu at position 51 and Tyr at position 92 in the amino acid sequence represented by SEQ ID NO:17 are modified with Val, Ser, Leu, Lys, Val and Phe, respectively, the amino acid sequence represented by SEQ ID NO:38 in which four residues of Thr at position 14, Pro at position 15, Leu at position 51 and Tyr at position 92 are modified with Ser, Leu, Val and Phe, respectively, and the amino acid sequence represented by SEQ ID NO:39 in which three residues of Ile at position 2, Leu at position 51 and Tyr at position 92 are modified with Val, Val and Phe, respectively.

Examples include a human CDR-grafted antibody in which VH of the antibody comprises the amino acid sequence represented by SEQ ID NO:16 or 18, a human CDR-grafted antibody in which VL of the antibody comprises the amino acid sequence represented by SEQ ID NO:17, 19, 38 or 39, a human CDR-grafted antibody in which VH and VL of the antibody comprise the amino acid sequences represented by SEQ ID NO:16 or 18 and SEQ ID NO:17, 19, 38 or 39, respectively, and the like, preferably a human CDR-grafted antibody in which VH and VL of the antibody comprise the amino acid sequence represented by SEQ ID NO:16 and SEQ ID NO:19, respectively, a human CDR-grafted antibody in which VH and VL of the antibody comprise the amino acid sequence represented by SEQ ID NO:16 and SEQ ID NO:38, respectively, and a human CDR-grafted antibody in which VH and VL of the antibody comprise the amino acid sequence represented by SEQ ID NO:16 and SEQ ID NO:39, respectively.

The antibody fragment of the present invention includes Fab, Fab', F(ab')$_2$, scFv, diabody, dsFv, a peptide comprising CDR, and the like.

An Fab is an antibody fragment having a molecular weight of about 50,000 and antigen binding activity, in which about a half of the N-terminal side of H chain and the entire L chain, among fragments obtained by treating IgG with a protease, papain (cut at an amino acid residue at position 224 of the H chain), are bound together through a disulfide bond (S—S bond).

The Fab of the present invention can be obtained by treating a human CDR-grafted antibody of the present invention which specifically reacts with FGF-8, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and antigen binding activity, which is slightly larger than the Fab bound via an S—S bond of the hinge region, among fragments obtained by treating IgG with a protease, pepsin (cut at the amino acid residue at position 234 in H chain).

The F(ab')$_2$ of the present invention can be obtained by treating an antibody which specifically reacts with FGF-8, with a protease, pepsin. Also, the F(ab')$_2$ can be produced by binding Fab' described below via an thioether bond or an S—S bond.

An Fab' is an antibody fragment having a molecular weight of about 50,000 and antigen binding activity, which is obtained by cutting an S—S bond of the hinge region of the above F(ab')$_2$.

The Fab' of the present invention can be obtained by treating F(ab') which specifically reacts with FGF-8, with a reducing agent, dithiothreitol. Also, the Fab' can be produced by inserting DNA encoding the Fab' of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (P) of 12 or more residues and which has an antigen-binding activity.

The scFv of the present invention can be produced by obtaining cDNAs encoding VH and VL of an antibody which specifically reacts with FGF-8, constructing DNA encoding the scFv, inserting the DNA into an expression vector for prokaryote or an expression vector for eukaryote, and then introducing the expression vector into a prokaryote or eukaryote to express the scFv.

A diabody is an antibody fragment in which scFv's having the same or different antigen binding specificity forms a dimer, and has an divalent antigen binding activity to the same antigen or two specific antigen binding activity to different antigens.

The diabody of the present invention, for example, a divalent diabody which specifically reacts with FGF-8, can be produced by obtaining cDNAs encoding VH and VL of the antibody, constructing DNA encoding scFv having a polypeptide linker of 3 to 10 residues, inserting the DNA into an expression vector for prokaryote or an expression vector for eukaryote, and then introducing the expression vector into a prokaryote or eukaryote to express the diabody.

A dsFV is obtained by binding polypeptides in which one amino acid residue of each of VH and VL is substituted with a cysteine residue via an S—S bond between the cysteine residues. The amino acid residue which is substituted with a cysteine residue can be selected based on a three-dimensional structure estimation of the antibody in accordance with the method shown by Reiter el al. [*Protein Engineerng*, 7, 697 (1994)].

The dsFv of the present invention can be produced by obtaining cDNAs encoding VH and VL of an antibody which specifically reacts with FGF-8, constructing DNA encoding the dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of CDR of VH or VL. A peptide comprising plural CDRs can be prepared by binding them directly or via an appropriate peptide linker.

The peptide comprising CDR of the present invention can be produced by constructing cDNAs encoding CDRs of VH and VL of an antibody which specifically reacts with FGF-8, inserting the cDNAs into an expression vector for prokaryote or an expression vector for eukaryote, and then by introducing the expression vector into a prokaryote or eukaryote to express the peptide. Also, the peptide comprising CDR can also be produced by a chemical synthesis method such as an Fmoc method (fluorenylmethoxycarbonyl method), a tBoc method (t-butyloxycarbonyl method), or the like.

A process for producing the human chimeric antibody, the human CDR-grafted antibody and the antibody fragment thereof which specifically react with FGF-8 and inhibit the function of FGF-8, a method for evaluating the activity and a method for using them are explained below.

1. Production of Human Chimeric Antibody and Human CDR-Grafted Antibody (1) Construction of Vector for Humanized Antibody Expression A vector for expression of humanized antibody is an expression vector for animal cell into which DNAs encoding CH and CL of a human antibody have been inserted, and is constructed by cloning each of DNAs encoding CH and CH of a human antibody into an expression vector for animal cell.

The C region of a human antibody may be CH and CL of any human antibody. Examples include CH belonging to γ1 subclass and CL belonging to κ class of a human antibody, and the like. As the DNAs encoding CH and CL of a human antibody, a chromosomal DNA comprising an exon and an intron or cDNA can be used. As the expression vector for animal cell, any expression vector can be used, so long as a C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981)], pSGIβd2-4 [*Cytotechnology*, 4, 173 (1990)], pSEI UK1Sed1-3 [*Cytotechnol.*, 13, 79 (1993)] and the like. Examples of a promoter and enhancer used for an expression vector for animal cell include an SV40 early promoter and enhancer [*J. Biochem.*, 101, 1307 (1987)], a Moloney mouse leukemia virus LTR promoter and enhancer [*Biochem. Biophys. Res. Comun.*, 149, 960 (1987)], an immunoglobulin H chain promoter [*Cell*, 41, 479 (1985)] and enhancer [*Cell*, 33, 717 (1983)], and the like.

The vector for expression of humanized antibody may be either of a type in which the H chain and the L chain of the antibody exist on separate vectors or of a type in which both chains exist on the same vector (tandem type). In respect of easiness of construction of a vector for expression of humanized antibody expression, easiness of introduction into animal cells, and balance between the expression amounts of the H chain and the L chain of the antibody in animal cells, a tandem type of the vector for expression of humanized antibody is preferred [*J. Immunol. Methods*, 167, 271 (1994)]. Examples of the tandem type of the vector for humanized antibody expression include pKANTEX93 (WO97/10354), pEE 18 [HYBRIDOMA, 17, 559 (1998)], and the like.

The constructed vector for expression of humanized antibody can be used for expression of a human chimeric antibody and a human CDR-grafted antibody in animal cells.

(2) Preparation of cDNA Encoding V Region of Antibody Derived from Non-Human Animal and Analysis of Amino Acid Sequence cDNAs encoding VH and VL of a non-human animal antibody such as a mouse antibody are obtained as follows.

mRNA is extracted from hybridoma cells producing a mouse antibody or the like, which synthesizes cDNA. The synthesized cDNA is inserted into a vector such as a phage or a plasmid to prepare a cDNA library. Each of a recombinant phage or recombinant plasmid containing cDNA encoding VH and a recombinant phage or recombinant plasmid containing cDNA encoding VL is isolated from the library using a part of the C region or V region of a mouse antibody as the probe. The full nucleotide sequences of VH and VL of the mouse antibody of interest on the recombinant phage or recombinant plasmid are determined, and the full amino acid sequences of VH and VL are deduced from the nucleotide sequences.

The non-human animal may be any animal such as mouse, rat, hamster or rabbit, so long as a hybridoma can be produced therefrom.

The method for preparing a total RNA from a hybridoma include a guanidine thiocyanate-cesium trifluoroacetate method [*Methods in Enzymol.*, 154, 3 (1987)] and the like. The method for preparing mRNA from total RNA include an oligo (dT) immobilized cellulose column method [*Molecular Cloning: A Laboratory Manual*, Cold Spring Harbor Lab. Press, New York (1989)] and the like. Also, a kit for preparing mRNA from a hybridoma cell includes Fast Track mRNA Isolation Kit (manufactured by Invitrogen), Quick Prep mRNA Purification Kit (manufactured by Pharmacia) and the like.

The method for synthesizing cDNA and preparing a cDNA library include conventional methods [*Molecular Cloning: A Laboratory Manual*, Cold Spring Harbor Lab. Press, New York (1989); *Current Protocols in Molecular Biology*, Supplement 1-34]; a method using a commercially available kit such as Super Script™ Plasmid System for cDNA Synthesis and Plasmid Cloning (manufactured by GIBCO BRL), ZAP-cDNA Kit (manufactured by Stratagene); and the like.

Any vector into which the cDNA synthesized using MRNA extracted from a hybridoma as the template may be inserted for preparing a cDNA library, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λEx-Cell and pT7T3 18U (manufactured by Pharmacia), pcD2 [*Mol. Cell. Biol.*, 3, 280 (1983)], pUC18 [*Gene*, 33, 103 (1985)] and the like.

Any *E. coli* for introducing the cDNA library constructed by a phage or plasmid vector may be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

A colony hybridization or plaque hybridization method using an isotope- or fluorescence-labeled probe may be used for selecting cDNA clones encoding VH and VL of an antibody derived from a non-human animal in the cDNA library [*Molecular Cloning: A Laboratory Manual*, Cold Spring Harbor Lab. Press, New York (1989)]. Also, the cDNAs encoding VH and VL can be prepared through polymerase chain reaction [PCR; *Molecular Cloning: A Laboratory Manual*, Cold Spring Harbor Lab. Press, New York (1989); *Current Protocols in Molecular Biology*, Supplement 1-34] by preparing primers and using CDNA prepared from mRNA or a CDNA library as the template.

The nucleotide sequence of the cDNA can be determined by digesting the cDNA selected by the above method with appropriate restriction enzymes and the like, cloning the fragments into a plasmid such as pBluescript SK(-) (manufactured by Stratagene), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as ABI377 (manufactured by Applied biosystems) or the like.

Whether the obtained cDNAs encode the full amino acid sequences of VH and VL of the antibody containing a secretory signal sequence can be confirmed by estimating the full amino acid sequences of VH and VL from the determined nucleotide sequence and comparing them with full amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full amino acid sequences of VH and VL of the antibody comprising a secretory signal sequence with full amino acid sequences of VH and VL of known antibodies [*Sequences of Proteins of Immunological Interest*, US Dept. Health and Human Services (1991)], and the subgroup to which they belong can be known. Furthermore, the amino acid sequence of each of CDRs of VH and VL can be identified.

Moreover, the novelty of the sequence can be examined by carrying out a homology search with sequences in any database, for example, SWISS-PROT, PIR-Protein or the like using the full amino acid sequences of VH and VL, for example, according to the BLAST method [*J. Mol. Biol*, 215, 403 (1990)] or the like.

(3) Construction of Human Chimeric Antibody Expression Vector

A human chimeric antibody expression vector can be constructed by cloning cDNAs encoding VH and VL of an antibody derived from a non-human animal in upstream of DNAs encoding CH and CL of a human antibody on the vector for expression of humanized antibody as described in the item 1(1). For example, by using a plasmid comprising cDNAs encoding VH and VL of an antibody derived from a non-human animal as the template, VH and VL of the antibody are amplified by PCR using primers at the 5'-terminal side and the 3'-terminal side comprising a recognition sequence of an appropriate restriction enzyme and a nucleotide sequence encoding the V region, the respective amplified product is cloned into a plasmid such as pBluescript SK(-) (manufactured by Stratagene), the nucleotide sequence is determined according to the method described in the item 1(2), and thus a plasmid comprising the DNA sequences encoding the amino acid sequences of VH and VL of the desired antibody is obtained. cDNAs encoding the amino acid sequences of VH and VL of the antibody are isolated from the plasmid and are cloned so as to express them in an appropriate form in upstream of the genes encoding the C regions of the H chain and L chain of the human antibody in the vector for expression of humanized antibody described in the item 1(1) to thereby construct a vector for a humanized chimeric antibody expression.

(4) Construction of cDNA Encoding V Region of Human CDR-Grafted Antibody cDNAs encoding VH and VL of a human CDR-grafted antibody can be obtained as follows. First, amino acid sequences of FRs in VH and VL of a human antibody to which amino acid sequences of CDRs in VH and VL of an antibody derived from a non-human animal antibody are grafted are selected. Any amino acid sequences of FRs in VH and VL of a human antibody can be used, so long as they are derived from a human antibody. Examples include amino acid sequences of FRs in VH and VL of human antibodies registered in database such as Protein Data Bank, and amino acid sequences common to subgroups of FRs in VH and VL of human antibodies [*Sequences of Proteins of Immunological Interest*, US Dept. Health and Human Services (1991)], and the like. Among these, in order to produce a human CDR-grafted antibody having potent activity, amino acid sequences having high homology (at least 60% or more) with amino acid sequence of FRs in VH and VL of a target antibody derived from a non-human animal is preferably selected.

Then, amino acid sequences of CDRs in VH and VL of the antibody derived from a non-human animal are grafted to the selected amino acid sequences of FRs in VH and VL of a human antibody to design amino acid sequences of VH and VL of a human CDR-grafted antibody. The designed amino acid sequences are converted to nucleotide sequences by considering the frequency of codon usage found in nucleotide sequences of genes encoding antibodies [*Sequence of Proteins of Immunological Interest*, US Dept. Health and Human Services (1991)], and the DNA sequences encoding the amino acid sequences of VH and VL of a human CDR-grafted antibody are designed. Several synthetic DNAs having a length of about 100 nucleotides are synthesized based on the designed nucleotide sequences, and PCR is carried out by using them. In this case, it is preferred in each of VH and VL that 6 synthetic DNAs are designed in view of the reaction efficiency of PCR and the lengths of DNAs which can be synthesized. Furthermore, they can be easily cloned into the vector for humanized antibody expression constructed in the item 1(1) by introducing the recognition sequence of an appropriate restriction enzyme to the 5' end of the synthetic DNAs present at both ends. After the PCR, an amplified product is cloned into a plasmid such as pBluescript SK(−) (manufactured by Stratagene), and the nucleotide sequences are determined according to the method described in the item 1(2) to obtain a plasmid having nucleotide sequences encoding VH and VL of a designed human CDR-grafted antibody.

(5) Modification of Amino Acid Sequence of V Region of Human CDR-Grafted Antibody It is known that when a human CDR-grafted antibody is produced by simply grafting only CDRs in VH and VL of an antibody derived from a non-human animal in FRs in VH and VL of a human antibody, its antigen-binding activity is lower than that of the original antibody derived from a non-human animal [*BIO/TECHNOLOGY*, 9, 266 (1991)]. As the reason, it is considered that several amino acid residues in not only CDRs but also FRs directly or indirectly relate to antigen-binding activity in VH and VL of the original antibody derived from a non-human animal, and that they are changed to different amino acid residues of different FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased [*BIO/TECHNOLOGY*, 9, 266 (1991)]. In the production of a human CDR-grafted antibody, how to efficiently identify the amino acid residues relating to the antigen binding activity in FR is most important, so that the three-dimensional structure of an antibody is constructed and analyzed by X-ray crystallography [*J. Mol. Biol*, 112, 535 (1977)], computer-modeling [*Protein Engineering*, 7, 1501 (1994)] or the like. Although the information of the three-dimensional structure of antibodies has been useful in the production of a human CDR-grafted antibody, a method for producing a human CDR-grafted antibody which is applicable to all antibodies has not been established yet. Therefore, various attempts must currently be necessary, for example, several modified antibodies of each antibody are produced to examine the relationship between each of the modified antibodies and its antibody binding activity.

The modification of the selected amino acid sequence of FR in VH and VL of a human antibody can be accomplished by PCR using various synthetic DNA for modification. With regard to the amplified product obtained by the PCR, the nucleotide sequence is determined according to the method as described in the above 1(2) to conform whether the objective modification has been carried out is confirmed.

(6) Construction of Vector for Human CDR-Grafted Antibody Expression

A vector for human CDR-grafted antibody expression can be constructed by cloning cDNAs encoding VH and VL of the human CDR-grafted antibody constructed in the item 1(4) and 1(5) into upstream of DNAs encoding CH and CL of the human antibody in the vector for expression of humanized antibody as described in the item 1(1). For example, when recognition sites for an appropriate restriction enzymes are introduced to the 5'-terminal of synthetic DNAs positioned at both ends among synthetic DNAs used in the construction of VH and VL of the human CDR-grafted antibody in the item 1(4) and 1(5), cloning can be carried out so that they are expressed in an appropriate form in upstream of DNAs encoding CH and CL of the human antibody in the vector for expression of humanized antibody as described in the item 1(1).

(7) Transient Expression of Humanized Antibodies

In order to efficiently evaluate the antigen binding activity of various humanized antibodies produced, the humanized antibodies can be expressed transiently using the humanized antibody expression vector as described in the item 1(3) and 1(6) or the modified expression vector thereof Any cell can be used as a host cell, so long as the host cell can express a humanized antibody. Generally, COS-7 cell (ATCC CRL1651) is used in view of its high expression amount [*Methods in Nucleic Acids Res.*, CRC Press, p. 283 (1991)]. The method for introducing the expression vector into COS-7 cell include a DEAE-dextran method [*Methods in Nucleic Acids Res.*, CRC Press, p. 283 (1991)], a lipofection method [*Proc. Natl. Acad. Sci. USA*, 84, 7413 (1987)] and the like.

After the vector is introduced into the cell, the expression amount and antigen binding activity of the humanized antibody in the culture supernatant can be determined by the enzyme immunoassay [ELISA; *Antibodies: A Laboratory Manual*, Cold Spring Harbor Laboratory, Chapter 14 (1988); *Monoclonal Antibodies: Principles and Practice*, Academic Press Limited (1996)] and the like.

(8) Stable Expression of Humanized Antibody

A transformant which produces a humanized antibody stably can be obtained by introducing into an appropriate host cell the humanized antibody expression vector described in the items 1(3) and 1(6).

The method for introducing the expression vector into a host cell include electroporation [Japanese Published Unexamined Patent Application No. 257891/90, *Cytotechnology*, 3, 133 (1990)] and the like.

Any cell can be used as the host cell into which the vector for humanized antibody expression is to be introduced, so long as it can express a humanized antibody. Examples include mouse SP2/0-Ag14 cell (ATCC CRL1581), mouse P3X63-Ag8.653 cell (ATCC CRL1580), CHO cell in which a dihydrofolate reductase gene (dhfr) is detective [*Proc. Natl.*

*Acad. Sci. U.S.A.*, 77, 4216 (1980)], rat YB2/3HL.P2.G11. 16Ag20 cell (YB2/0 cell, ATCC CRL1662) and the like.

After the expression vector is introduced into the cell, transformants which express a humanized antibody stably are selected by culturing in a medium for animal cell culture comprising an agent such as G418 sulfate (G418, manufactured by Sigma) or the like [*J. Immunol. Methods*, 167, 271 (1994)]. The medium for animal cell culture includes PRMI1640 medium (manufactured by Nissui Pharmaceutical), GIT medium (manufactured by Nissui Pharmaceutical), EX-CELL302 medium (manufactured by JRH), IMDM medium (manufactured by GIBCO BRL), Hybridoma-SFM medium (manufactured by GIBCO BRL), media obtained by adding various additives such as FBS to these media, and the like. The humanized antibody can be produced and accumulated in a culture medium by culturing the selected transformants in a medium. The amount and the antigen binding activity of the humanized antibody expressed in the culture medium can be measured by ELISA or the like. Also, the production amount of the humanized antibody can be increased by transformant using dhfr amplification system or the like [*J. Immunol. Methods*, 167, 271 (1994)].

The humanized antibody can be purified from the medium culturing the transformant by using a protein A column [*Antibodies, A Laboratory Manual*, Cold Spring Harbor Laboratory, Chapter 8 (1988), *Monoclonal Antibodies: Principles and Practice*, Academic Press Limited (1996)]. Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis [SDS-PAGE; *Nature*, 227, 680 (1970)], Western blotting [*Antibodies, A Laboratory Manual*, Cold Spring Harbor Laboratory, Chapter 12 (1988), *Monoclonal Antibodies: Principles and Practice*, Academic Press Limited (1996)], and the like.

2. Preparation of Antibody Fragment

The antibody fragment can be prepared based on the humanized antibody described in the item 1 genetically or proteinochemically. The antibody fragment includes Fab, F(ab')$_2$, Fab', scFv, Diabody, dsFv, a peptide comprising CDR and the like.

(1) Preparation of Fab

Fab can be prepared by treating IgG with a proteolytic enzyme papain. After the papain treatment, when the original antibody is an IgG subclass having a protein A binding activity, uniform Fab can be collected by passing through a protein A column in order to separate IgG molecules and Fc fragments [*Monoclonal Antibodies: Principles and Practice*, third edition (1995)]. When the original antibody is an antibody of IgG subclass having no protein A binding activity, Fab can be collected by ion exchange chromatography in a fraction eluted at a low salt concentration [*Monoclonal Antibodies: Principles and Practice*, third edition (1995)]. Furthermore, Fab can also be prepared genetically by using *Escherichia coli*. For example, an Fab expression vector can be prepared by cloning the DNA encoding the antibody V region described in the items 1(2), 1(3) and 1(5) into a vector for expression of Fab. As the vector for expression of Fab, any vector can be used, so long as a DNA encoding Fab can be inserted and expressed. Examples include pIT106 [*Science*, 240, 1041 (1988)] and the like. Fab can be formed and accumulated in an inclusion body or periplasmic space by introducing the Fab expression vector into an appropriate *Escherichia coli*. Fab having a binding activity can be obtained from the inclusion body by a refolding method generally used for producing a protein, and when it is expressed in the periplasmic space, the Fab having a binding activity is leaked in the culture supernatant. Uniform Fab can be purified after the refolding or from the culture medium using an antigen-linked column [*Antibody Engineering, A Practical Guide*, W. H. Freeman and Company (1992)].

(2) Preparation of F(ab')$_2$

F(ab')$_2$ can be prepared by treating IgG with a protease pepsin. After the pepsin treatment, uniform F(ab')$_2$ can be recovered by a purification procedure similar to the case of Fab [*Monoclonal Antibodies: Principles and Practice*, third edition, Academic Press (1995)]. Furthermore, it can also be prepared by the method described in the item 2(3) in which Fab' is treated with maleimide such as o-PDM or bismaleimide hexane to form a thioether bond, or a method in which it is treated with DTNB to form an S—S bond [*Antibody Engineering, A Practical Approach*, IRL PRESS (1996)].

(3) Preparation of Fab'

Fab' can be prepared by treating F(ab')$_2$ described in the item 2(2) with a reducing agent such as dithiothreitol. Furthermore, Fab' can be prepared genetically by using *Escherichia coli*. For example, an Fab' expression vector can be constructed by cloning the DNA encoding the antibody V region described in the items 1(2), 1(4) and 1(5) into a vector for expression of Fab'. As the vector for expression of Fab', any vector can be used, so long as a DNA encoding Fab' can be inserted and expressed. Examples include pAK19 [*Bio/Technology*, 10, 163 (1992)] and the like. Fab' can be formed and accumulated in an inclusion body or periplasmic space by introducing the Fab' expression vector into an appropriate *Escherichia coli*. Fab' having a binding activity can be obtained from the inclusion body by a refolding method generally used for producing a protein, and when it is expressed in the periplasmic space, it can be collected extracellularly by disrupting the cells with a treatment such as lysozyme partial digestion, osmotic pressure shock or sonication. Uniform Fab' can be purified after the refolding or from the disrupted cell suspension using a protein G column or the like [*Antibody Engineering, A Practical Approach*, IRL PRESS (1996)].

(4) Preparation of scFv scFv can be prepared genetically using a phage or *Escherichia coli*. For example, a DNA encoding scFv is produced by ligating DNAs encoding the antibody VH and VL described in the items 1(2), 1(4) and 1(5) via a DNA encoding a polypeptide linker comprising an amino acid sequence of 12 residues or more. An scFv expression vector can be constructed by cloning the DNA into a vector for expression of scFv. As the vector for expression of scFv, any vector can be used, so long as DNA encoding scFv can be inserted and expressed. Examples include pCANTAB5E (manufactured by Pharmacia), Phfa [*Hum. Antibody Hybridoma*, 5, 48 (1994)] and the like. The scFv expression vector was introduced into an appropriate *Escherichia coli* and infected with a helper phage to thereby obtain a phage which expresses scFv fused with the phage surface protein on the phage surface. Also, scFv can be formed and accumulated in the inclusion body or periplasmic space of *Escherichia coli* into which scFv expression vector is introduced. scFv having a binding activity can be obtained from the inclusion body by a refolding method generally used for producing a protein, and when it is expressed in the periplasmic space, it can be collected extracellularly by disrupting the cells with a treatment such as lysozyme partial digestion, osmotic pressure shock, sonication or the like. Uniform scFv can be purified after the refolding or from the disrupted cell suspension by cation exchange chromatography or the like [*Antibody Engineering, A Practical Approach*, IRL PRESS (1996)].

(5) Preparation of Diabody

Diabody can be prepared by changing the polypeptide linker used to prepare the above scFv to about 3 to 10 residues. A divalent diabody can be prepared when VH and VL of one antibody species is used. A diabody having two different specificity can be prepared when VH and VL of two antibody species are used [*FEBS Letters*, 453, 164 (1999), *Int. J. Cancer*, 77, 763 (1998)].

(6) Preparation of dsFv dsFv can be prepared genetically by using *Escherichia coli*. First, DNAs in which an encoded amino acid residue is replaced with a cysteine residue are produced by introducing mutation into appropriate positions of the DNAs encoding the antibody VH and VL described in the items 1(2), 1(4) and 1(5). Expression vectors for VH and VL can be produced by cloning each of the DNAs into a vector for expression of dsFv. As the vector for expression of dsFv, any vector can be used, so long as DNA encoding dsFv can be inserted and expressed. Examples include pULI9 [*Protein Engineering*, 7, 697 (1994)] and the like. The expression vectors for VH and VL are introduced into an appropriate *Escherichia coli* to thereby form and accumulate the VH and VL in the inclusion body or periplasmic space. The VH and VL are obtained from the inclusion body or periplasmic space and mixed, and dsFv having a binding activity can be obtained by a refolding method generally used for producing a protein. After the refolding, it can be further purified by ion exchange chromatography, gel filtration or the like [*Protein Engineering*, 7, 697 (1994)].

(7) Preparation of Peptide Comprising CDR

A peptide comprising CDR can be prepared by a chemical synthesis method such as Fmoc or tBoc. Also, a DNA encoding a peptide comprising CDR is prepared, and the resulting DNA is cloned into an appropriate vector for expression to thereby prepare the peptide comprising CDR. As the vector for expression, any vector can be used, so long as a DNA encoding a peptide comprising CDR is inserted and expressed. Examples include pLEX (manufactured by Invitrogen), pAX4a+ (manufactured by Invitrogen) and the like. The expression vector is introduced into an appropriate *Escherichia coli* so that the peptide comprising CDR can be formed and accumulated in the inclusion body or periplasmic space. The peptide comprising CDR can be obtained from the inclusion body or periplasmic space, and it can be purified by ion exchange chromatography, gel filtration or the like [*Protein Engineering*, 7, 697 (1994)].

3. Activity Evaluation of Humanized Antibody or Antibody Fragment (1) Antigen Binding Activity The FGF-8 binding activity of the prepared humanized antibody or antibody fragment can be measured by ELISA or surface plasmon resonance [*J. Immunol. Methods*, 145, 229 (1991)] or the like.

(2) Inhibition Activity for Function having FGF-8

The inhibition activity for function having FGF-8 of the prepared humanized antibody or the antibody fragment can be measured, e.g., by a cell growth test using a cell line. For example, the inhibition activity for function having FGF-8 of the prepared humanized antibody or antibody fragment can be measured by culturing the mouse breast cancer cell line SC-3 [*Proc. Natl. Acad. Sci. USA.*, 89, 8928 (1992)], the mouse fibroblast cell line NIH3T3 or a human prostate cancer, breast cancer or ovarian cancer cell line as the target cells, using a medium containing 1 to 100 ng/ml of FGF-8 or testosterone, for a period of 24 to 72 hours after adding the humanized antibody or the antibody fragment serially diluted to a final concentration of 0.001 to 100 µg/ml to the medium, and then measuring the number of viable cells using an MTT [3-(4,5-dimethyl-2-thiazonyl)-2,5-diphenyl-2H-tetrazolium bromide] solution, a cell counting kit, a WST-1 kit or the like. Also, the activity of the humanized antibody or the antibody fragment to inhibit binding of FGF-8 to the cell surface receptor can be measured by Bolton-Hunter method in which FGF-8 labeled with $^{125}$I is used [*Biochem. J.*, 133, 527 (1973)] or the like to the above cell lines.

(3) In Vitro Antitumor Effect

In vivo antitumor effect of the prepared humanized antibody or the antibody fragment can be evaluated, for example, by using the nude mouse cancer cell transplantation system shown below.

a. Evaluation of Antitumor Effect for Early Cancer Model

The mouse breast cancer cell line SC-3 is suspended in PBS to give a density of $1\times10^7$ cells/ml and subcutaneously transplanted into 6- to 8-week-old male nude mice at a dose of 0.1 ml/animal ($1\times10^6$ cells/animal). Just after the transplantation, the humanized antibody or the antibody fragment is administered into the mouse abdominal cavity or caudal vein at a dose of 10 µg to 400 µg/animal. The antibody is administered at a frequency of 1 to 7 times a week in a total of 1 to 10 times. The antitumor effect can be evaluated by periodically measuring tumor volumes for 14 to 60 days after the tumor transplantation, and comparing the tumor volumes with those of the negative control antibody administered group or the solvent administered group. Also, the tumor volume (V) is calculated based on the following equation by measuring its length (L), width (W) and height (H) using slide calipers.

$$V (\text{mm}^3) = (L) \times (W) \times (H) \times 0.5236$$

b. Evaluation of Antitumor Effect for Advanced Cancer Model

SC-3 is suspended in PBS to give a density of $1\times10^7$ cells/ml and subcutaneously transplanted into 6- to 8-week-old male nude mice at a dose of 0.1 ml/animal ($1\times10^6$ cells/animal). When the tumor volume becomes approximately from 100 to 300 mm$^3$ (around the 14th day after tumor transplantation), administration of the humanized antibody or antibody fragment into the mouse abdominal cavity or caudal vein is started at a dose of from 10 µg to 400 µg/animal. The antibody is administered at a frequency of 1 to 7 times a week in a total of 1 to 10 times. The antitumor effect can be evaluated in the same manner as in the early cancer model of a.

4. Method for using Humanized Antibody or Antibody Fragment Thereof

Since the humanized antibody or the antibody fragment thereof of the present invention specifically binds to FGF-8 which is considered to be a growth factor of human cancer cells which show sex hormone-dependent growth and inhibits the function of FGF-8, it will be useful in treating and diagnosing human cancers such as prostate cancer, breast cancer, ovarian cancer and testis tumor. Also, since the proportion of amino acid sequences derived from human antibodies of the humanized antibody or the antibody fragment thereof is higher than that in antibodies derived from a non-human animal, it is expected that the humanized antibody or the antibody fragment thereof shows strong cytotoxic activity in the human body, it does not show immunogenicity, and its effects continue for a long time.

The humanized antibody or the antibody fragment thereof of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in an antibody or peptide formulation.

The dosage form includes sprays, capsules, tablets, granules, syrups, emulsions, suppositories, injections, ointments, tapes, and the like.

Formulations suitable for oral administration include emulsions, syrups, capsules, tablets, powders, granules, and the like.

Liquid preparations such as emulsions and syrups, can be produced by using additives, for example, water; saccharides such as sucrose, sorbitol, fructose, glycols such as polyethylene glycol, propylene glycol, oils such as sesame oil, olive oil, soybean oil; antiseptics such as p-hydroxybenzoate; and flavors such as strawberry flavor, peppermint.

Capsules, tablets, powders, granules and the like can be produced by using additives, for example, fillers such as lactose, glucose, sucrose, mannitol; disintegrating agents such as starch, sodium alginate, lubricants such as magnesium stearate; talc, binders such as polyvinyl alcohol, hydroxypropylcellulose, gelatin; surfactants such as fatty acid esters; and plasticizers such as glycerine.

Formulations suitable for parenteral administration include injections, suppositories, sprays and the like.

Injections can be prepared by using a carrier such as a salt solution, a glucose solution or a mixture thereof.

Suppositories can be prepared by using a carrier such as cacao butter, hydrogenated fat or carboxylic acid.

Also, sprays can be prepared from the antibody itself or using a carrier or the like which does not stimulate oral and airway mucous membranes of patients and can facilitate absorption of the antibody or antibody fragment thereof by dispersing it as minute particles.

The carrier includes lactose, glycerine, and the like. Depending on the properties of the antibody or the antibody fragment and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 0.01 mg/kg to 20 mg/kg per day per adult.

Figure 1:
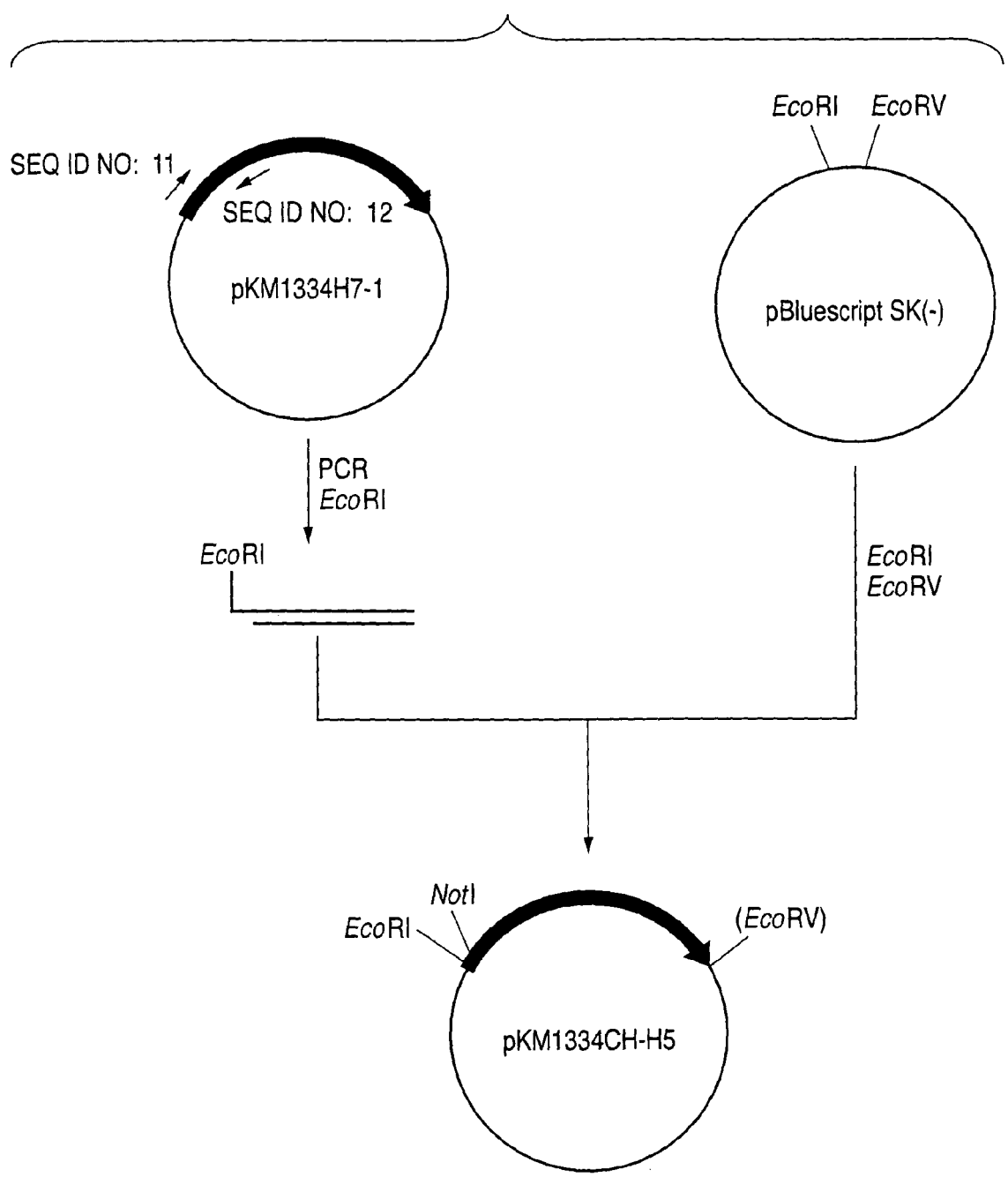
FIG. 1 shows construction steps of plasmid pKM1334CH-H5.

The present invention is explained below based on Examples, however, the scope of the present invention is not limited thereto.

BEST MODE FOR CARRYING OUT THE INVENTION

Example 1

Preparation of Anti-FGF-8 Chimeric Antibody

1. Isolation and Analysis of cDNA Encoding the V Region of Anti-FGF-8 Mouse Antibody
(1) Preparation of mRNA from Hybridoma Cells Producing Anti-FGF-8 Mouse Antibody From $1 \times 10^7$ cells of a hybridoma KM1334 (FERM BP-5451) capable of producing a mouse antibody against FGF-8 (hereinafter referred to as "anti-FGF-8 mouse antibody"), about 8 µg of mRNA was prepared by using a mRNA preparation kit Fast Track mRNA Isolation Kit (manufactured by Invitrogen) according to the manufacture's instructions attached thereto.

(2) Preparation of Anti-FGF-8 Mouse Antibody H Chain and L Chain cDNA Libraries

From 5 µg of mRNA of KM1334 obtained in item 1(1) of Example 1, cDNA having an EcoRI-NotI adapter on both termini was synthesized by using Time Saver cDNA Synthesis Kit (manufactured by Amersham Pharmacia Biotech) according to the manufacture's instructions attached thereto. Next, cDNA libraries were prepared by using λ ZAPII Cloning Kit (manufactured by Stratagene). First, a total amount of the cDNA was dissolved in 20 µl of sterile water and then fractionated by agarose gel electrophoresis to collect about 0.1 µg for each of a cDNA fragment of about 1.5 kb which corresponds to the H chain of IgG class antibody and a cDNA fragment of about 1.0 kb which corresponds to the L chain of κ class. Next, each of 0.1 µg of the cDNA fragment of about 1.5 kb and 0.1 µg of the cDNA fragment of about 1.0 kb was ligated with 1 µg of the λZAPII vector in which termini had been dephosphorylated with Calf Intestine Alkaline Phosphatase after digestion with a restriction enzyme EcoRI according to the manufacture's instructions attached thereto.

Using Gigapack II Packaging Extracts Gold (manufactured by Stratagene) according to the manufacture's instructions attached thereto, 4 µl of the each reaction solution after the ligation was packaged into λ phage, and an appropriate amount thereof was infected with *Escherichia coli* XL1-Blue [*Biotechniques*, 5, 376 (1987)] to obtain about $8.1 \times 10^4$ and $5.5 \times 10^4$ of phage clones as H chain cDNA library and L chain cDNA library of KM1334, respectively. Next, each phage was fixed on a nylon membrane according to the conventional method [*Molecular Cloning: A Laboratory Manual*, Cold Spring Harbor Lab. Press, New York (1989)].

(3) Cloning of Anti-FGF-8 Mouse Antibody H Chain and L Chain cDNA

Using ECL Direct Nucleic Acid Labelling and Detection Systems (manufactured by Amersham Pharmacia Biotech) according to the manufacture's instructions attached thereto, clones of the H chain cDNA library and L chain cDNA library of KM1334 on the nylon membrane prepared in the item 1(2) of Example 1 were detected by using mouse antibody C region cDNA [H chain is a DNA fragment containing mouse Cγ1 cDNA [*J. Immunol.*, 146, 2010 (1991)] and L chain is a DNA fragment containing mouse Cκ CDNA [*Cell*, 22, 197 (1980)] as a probe to obtain 10 phage clones for each of the H chain and L chain clones which strongly reacted to the probe. Next, according to the manufacture's instructions of λZAPII Cloning Kit (manufactured by Stratagene), each phage clone was converted into plasmid by the in vivo excision method. Nucleotide sequence of cDNA contained in each of the thus obtained plasmids was determined by the dideoxy method [*Molecular Cloning: A Laboratory Manual*, Cold Spring Harbor Lab. Press, New York (1989)] using Big Dye Terminator Kit ver. 2 (manufactured by Applied Biosystems). As a result, a plasmid pKM1334H7-1 containing a full length functional H chain cDNA and a plasmid pKM1334L7-1 containing a full length functional L chain cDNA, in which ATG sequence considered to be an initiation codon is present in the 5'-terminal of the cDNA, were obtained.

(4) Analysis of Amino Acid Sequence of V Region of Anti-FGF-8 Mouse Antibody

A full nucleotide sequence of VH contained in the plasmid pKM1334H7-1 is shown in SEQ ID NO:1, its deduced full amino acid sequence is shown in SEQ ID NO:2, a full nucleotide sequence of VL contained in the plasmid pKM1334L7-1 is shown in SEQ ID NO:3, and its deduced full amino acid sequence is shown in SEQ ID NO:4. Based on the comparison with sequence data of known mouse antibodies [*Sequences of Proteins of Immunological Interest*, US Dept. Health and Human Services (1991)] and comparison with results of the analysis of N-terminal amino acid sequences of H chain and L chain of purified anti-FGF-8 mouse antibody KM1334, carried out by automatic Edman degradation using a protein sequencer PPSQ-10 (manufactured by Shimadzu Corporation), it was found that each cDNA thus isolated is a full length cDNA encoding the anti-FGF-8 mouse antibody KM1334 containing a secretory signal sequence, and the amino acid sequence at positions 1 to 19 of H chain shown in SEQ ID NO:2 and the amino acid sequence at positions 1 to 19 of L chain shown in SEQ ID NO:4 are the secretory signal sequences. Also, amino acid sequences of VH and VL excluding the secretory signal sequence are shown in SEQ ID NO:40 and SEQ ID NO:41, respectively.

Next, novelty of the amino acid sequences of VH and VL of the anti-FGF-8 mouse antibody KM1334 was examined. Using GCG Package (version 9.1, manufactured by Genetics Computer Group) as a sequence analyzing program, an amino acid sequence data base of known proteins [PIR-Protein (Release 56.0)] was retrieved by the BLAST method [*J. Mol. Biol.*, 215, 403 (1990)]. As a result, completely identical sequences were not found regarding both H chain and L chain, so that it was confirmed that VH and VL of the anti-FGF-8 mouse antibody KM1334 are novel amino acid sequences.

In addition, CDRs of VH and VL of the anti-FGF-8 mouse antibody KM1334 were identified by comparing them with known antibody amino acid sequences. Amino acid sequences of CDR1, 2 and 3 of VH of the anti-FGF-8 mouse antibody KM1334 are shown in SEQ ID NOs:5, 6 and 7, respectively, and amino acid sequences of CDR1, 2 and 3 of VL in SEQ D NOs:8, 9 and 10, respectively.

2. Stable Expression of Anti-FGF-8 Chimeric Antibody using Animal Cells
(1) Construction of Plasmid Containing VH cDNA of Anti-FGF-8 Chimeric Antibody Using 50 ng of the plasmid pKM1334H7-1 obtained in the item 1(3) of Example 1 as the template, synthetic DNA fragments having the nucleotide sequences shown in SEQ ID NOs:11 and 12 (manufactured by GENSET) were added as primers to give a final concentration of 0.3 µmol/l, and PCR was carried out by firstly heating 50 µl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase (manufactured by TOYOBO). The reaction product was purified, dissolved in sterile water and then allowed to react at 37° C.

for 1 hour by using 10 units of restriction enzyme EcoRI (manufactured by Takara Shuzo). The reaction solution was fractionated by agarose gel electrophoresis to collect about 0.3 μg of an EcoRI fragment of about 0.48 kb (5'-terminal side is EcoRI, 3'-terminal side is blunt end).

Next, 3 μg of plasmid pBluescript SK(–) was allowed to react with 10 units of restriction enzyme EcoRI (manufactured by Takara Shuzo) and 10 units of restriction enzyme EcoRV (manufactured by Takara Shuzo) at 37° C. for 1 hour. The reaction solution was fractionated by agarose gel electrophoresis to collect about 2 μg of an EcoRI-EcoRV fragment of about 2.95 kb.

Next, 0.1 μg of the EcoRI fragment of VH cDNA and 0.1 μg of the EcoRI-EcoRV fragment derived from the plasmid pBluescript SK(–) obtained in the above were added to 10 μl in total volume of sterile water and ligated by using Ligation High (manufactured by TOYOBO). Using the thus obtained recombinant plasmid DNA solution, *E. coli* XL1-Blue was transformed to obtain a plasmid pKM1334CH—H5 shown in FIG. 1 containing VH cDNA of anti-FGF-8 chimeric antibody.

(2) Construction of Plasmid Containing VL cDNA of Anti-FGF-8 Chimeric Antibody

Using 50 ng of the plasmid pKM1334L7-1 obtained in the item 1(3) of Example 1 as the template, synthetic DNA fragments having the nucleotide sequences shown in SEQ ID NOs:13 and 14 (manufactured by GENSET) were added as primers to give a final concentration of 0.3 μmol/l, and PCR was carried out by firstly heating 50 μl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase (manufactured by TOYOBO). The reaction product was purified, dissolved in sterile water and then allowed to react at 37° C. for 1 hour by using 10 units of restriction enzyme EcoRI (manufactured by Takara Shuzo). The reaction solution was fractionated by agarose gel electrophoresis to collect about 0.3 μg of an EcoRI fragment of about 0.45 kb (5'-terminal side is EcoRI, 3'-terminal side is blunt end).

Figure 2:
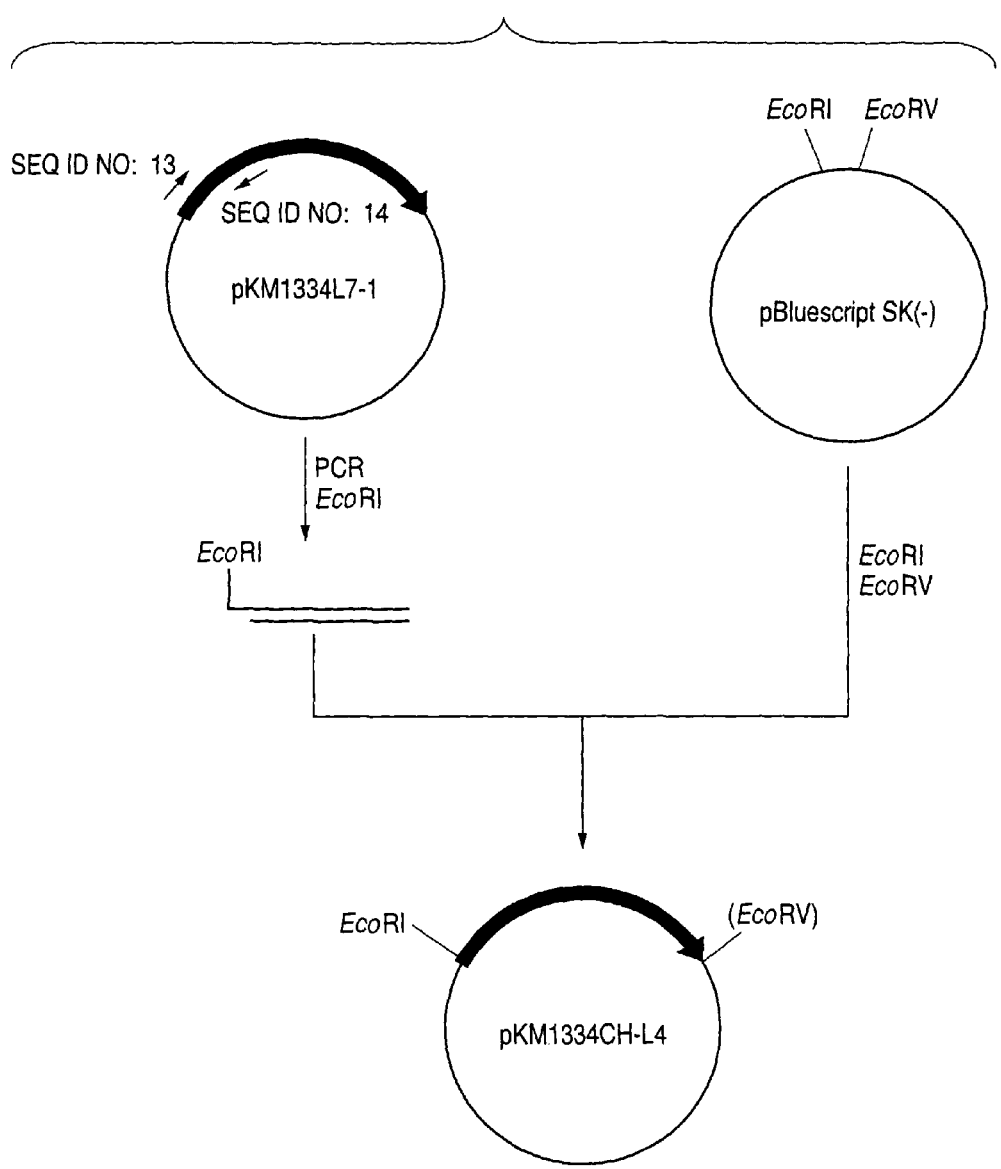
FIG. 2 shows construction steps of plasmid pKM1334CH-L4.

Next, 0.1 μg of the EcoRI fragment of VL cDNA and 0.1 μg of the EcoRI-EcoRV fragment derived from the plasmid pBluescript SK(–) both obtained in the above were added to 10 μl in total volume of sterile water and ligated using Ligation High (manufactured by TOYOBO). Using the thus obtained recombinant plasmid DNA solution, *E. coli* XL1-Blue was transformed to obtain a plasmid pKM1334CH-L4 shown in FIG. 2 containing VL cDNA of anti-FGF-8 chimeric antibody.

(3) Construction of Anti-FGF-8 Chimeric Antibody Expression Vector pKANTEX1334

Using the humanized antibody expression vector pKANTEX93 described in WO97/10354 and the plasmids pKM1334CH-H5 and pKM1334CH-L4 obtained in the items 2(1) and 2(2) of Example 1, an anti-FGF-8 chimeric antibody expression vector pKANTEX1334 was constructed as follows.

A reaction was carried out by mixing 3 μg of the plasmid pKM1334CH-H5 obtained in the item 2(1) of Example 1 with 10 units of restriction enzyme NotI (manufactured by New England Biolabs) and 10 units of restriction enzyme ApaI (manufactured by Takara Shuzo) at 37° C. for 1 hour. The reaction solution was fractionated by agarose gel electrophoresis to collect about 0.2 μg of a NotI-ApaI fragment of about 0.48 kb.

Next, 3 μg of the humanized antibody expression vector pKANTEX93 was allowed to react with 10 units of restriction enzyme ApaI (manufactured by Takara Shuzo) and 10 units of restriction enzyme NotI (manufactured by New England Biolabs) at 37° C. for 1 hour. The reaction solution was fractionated by agarose gel electrophoresis to collect about 2 μg of an ApaI-NotI fragment of about 12.8 kb.

Figure 3:
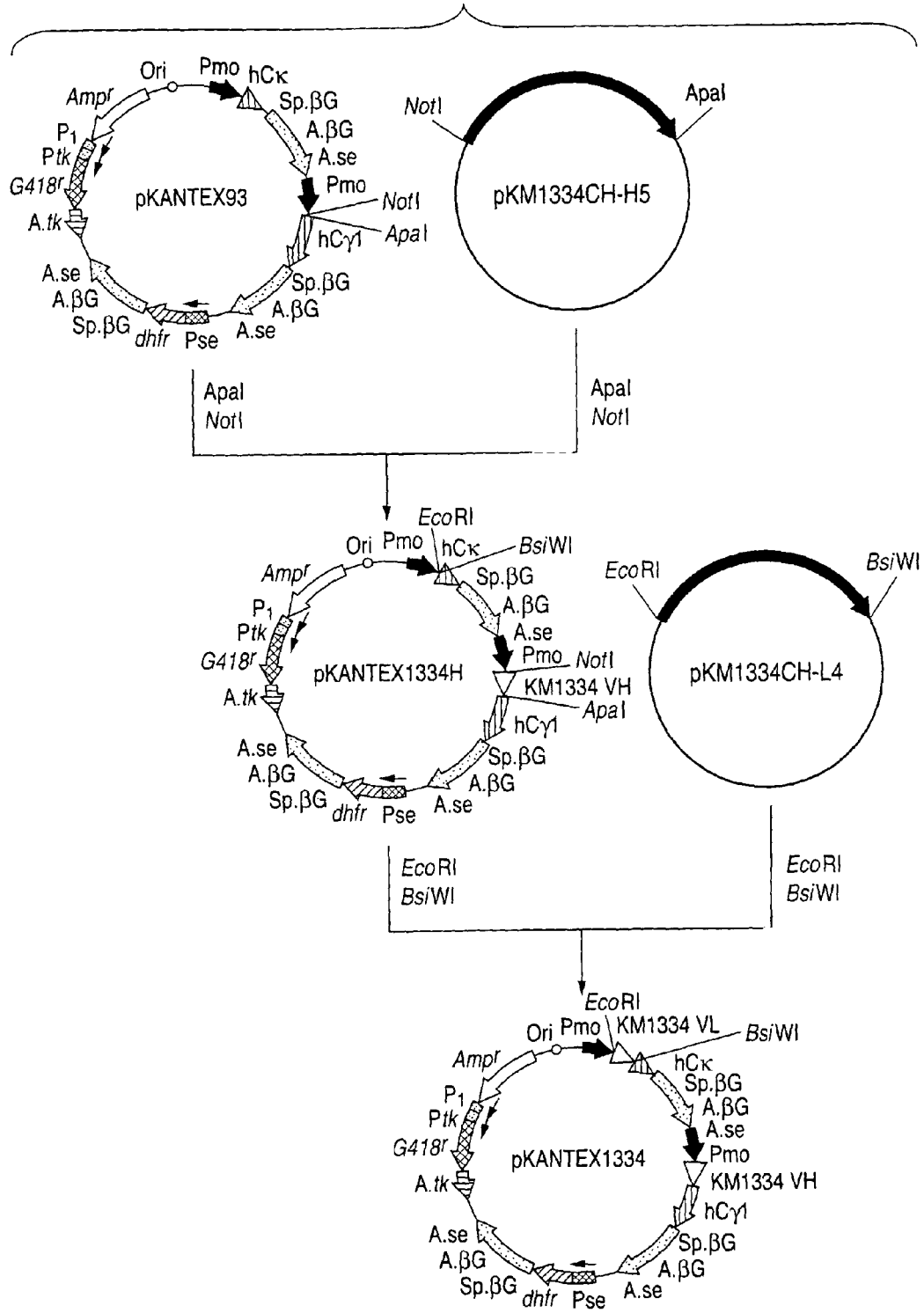
FIG. 3 shows construction steps of plasmid pKANTEX1334.

Next, 0.1 μg of the NotI-ApaI fragment derived from the plasmid pKM1334CH-H5 and 0.1 μg of the NotI-ApaI fragment derived from the plasmid pKANTEX93 were added to 10 μl in total volume of sterile water and ligated by using Ligation High (manufactured by TOYOBO). Using the thus obtained recombinant plasmid DNA solution, *E. coli* XL1-Blue was transformed to obtain the plasmid pKANTEX1334H shown in FIG. 3.

Next, 3 μg of the plasmid pKM1334CH-L4 obtained in the item 2(2) of Example 1 was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 0.2 μg of an EcoRI-BsiWI fragment of about 0.45 kb.

Next, 3 μg of the plasmid pKANTEX1334H obtained in the above was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 2 μg of an EcoRI-BsiWI fragment of about 13.30 kb.

Next, 0.1 μg of the EcoRI-BsiWI fragment derived from the plasmid pKM1334CH-L4 and 0.1 μg of the EcoRI-BsiWI fragment derived from the plasmid pKANTEX1334H were added to 10 μl in total volume of sterile water and ligated using Ligation High (manufactured by TOYOBO). Using the thus obtained recombinant plasmid DNA solution, the *E. coli* XL1-Blue was transformed to obtain the plasmid pKANTEX1334 shown in FIG. 3.

Using 400 μg of the thus obtained plasmid, analysis of its nucleotide sequence was carried out by the dideoxy method [*Molecular Cloning: A Laboratory Manual*, Cold Spring Harbor Lab. Press, New York (1989)] using Big Dye Terminator Kit ver. 2 (manufactured by Applied Biosystems), thereby confirming that a plasmid into which the DNA of interest had been cloned was obtained.

(4) Stable Expression of Anti-FGF-8 Chimeric Antibody using CHO-DG44 Cell

Using the anti-FGF-8 chimeric antibody expression vector pKANTEX1334 obtained in the item 2(3) of Example 1, expression of anti-FGF-8 chimeric antibody in CHO/DG44 cell [*Proc. Natl., Acad. Sci. USA*, 77, 4216 (1980)] was carried out as follows.

After 10 μg of the plasmid pKANTEX1334 was introduced into $1.6 \times 10^6$ cells of CHO/DG44 cell by electroporation [*Cytotechnology*, 3, 133 (1990)], the cells were suspended in 10 to 30 ml of IMDM-1×HT supplement-dFBS(10) [IMDM medium containing 10% of dialyzed fetal bovine serum (dFBS) and 1×HT supplement, (all manufactured by GIBCO)] and dispensed at 100 μl/well into a 96 well microtiter plate (manufactured by IWAKI). After culturing at 37° C. for 24 hours in a 5% $CO_2$ incubator, the culture medium was changed to IMDM-dFBS(10) prepared by eliminating HT supplement alone, followed by culturing for 1 to 2 weeks. Culture supernatants were recovered from wells where resistant colonies were grown and became confluent, and the antigen binding activity of anti-FGF-8 chimeric antibodies in the supernatants was measured by the ELISA shown in the item 2(6) of Example 1.

Regarding the transformants of wells in which expression of anti-FGF-8 chimeric antibodies was found in the culture supernatants, in order to increase antibody expression quantity using a dhfr gene amplification system, they were inoculated into a 24 well plate and cultured for 2 weeks in IMDM-dFBS(10) medium containing 50 nmol/l methotrexate (MTX; manufactured by SIGMA) which is an inhibitor of the dhfr gene product dihydrofolate reductase. The MTX concentration was further increased to 200 nmol/l and then to 500 nmol/l, followed by culturing for 2 weeks at each increasing step to induce transformants showing 500 nmol/l MTX resistance. When the transformants became confluent in wells, the antigen binding activity of anti-FGF-8 chimeric antibodies in the supernatants was measured by the ELISA shown in the item 2(6) of Example 1. Finally, transformants capable of growing in the IMDM-dFBS(10) medium containing 500 nmol/l MTX and of highly expressing anti-FGF-8 chimeric antibodies were obtained. Regarding the thus obtained transformants, single cell isolation (cloning) was carried out by limiting dilution method, and a transformed cell clone showing the highest expression of anti-FGF-8 chimeric antibody was named KM3034 Also, the KM3034 has been deposited on Dec. 26, 2001, as FERM BP-7836 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

(5) Stable Expression of Anti-FGF-8 Chimeric Antibody using YB2/0 Cell

Using the anti-FGF-8 chimeric antibody expression vector pKANTEX1334 obtained in the item 2(3) of Example 1, expression of anti-FGF-8 chimeric antibody in YB2/0 cell (ATCC CRL 1662) was carried out as follows.

After 10 μg of the plasmid pKANTEX1334 was introduced into 4×10$^6$ cells of YB2/0 cell (ATCC CRL1662) by electroporation [*Cytotechnology*, 3, 133 (1990)], the cells were suspended in 40 ml of Hybridoma-SFM-FBS(5) [Hybridoma-SFM medium (manufactured by Gibco) containing 5% fetal bovine serum (FBS, manufactured by PAA Laboratories)] and dispensed at 200 μl/well into a 96 well culture plate (manufactured by Sumitomo Bakelite). After culturing at 37° C. for 24 hours in a 5% CO$_2$ incubator, G418 was added to give a concentration of 1 mg/ml, followed by culturing for 1 to 2 weeks. Culture supernatants were recovered from wells in which colonies of transformants showing G418-resistance were grown and their propagation was confirmed, and the antigen binding activity of anti-FGF-8 chimeric antibodies in the supernatants was measured by the ELISA shown in the item 2(6) of Example 1.

Regarding the transformants of wells in which expression of anti-FGF-8 chimeric antibodies was found in the culture supernatants, in order to increase antibody expression quantity using a dhfr gene amplification system, they were suspended in the Hybridoma-SFM-FBS(5) medium containing 1 mg/ml G418 and 50 nmol/l MTX (manufactured by SIGMA) to give a density of 1 to 2×10$^5$ cells/ml, and dispensed at 1 ml into a 24 well plate (manufactured by Greiner). By culturing at 37° C. for 1 to 2 weeks in a 5% CO$_2$ incubator, transformants showing 50 nmol/l MTX resistance were induced. The antigen binding activity of anti-FGF-8 chimeric antibodies in the culture supernatants in wells where proliferation of transformants was observed was measured by the ELISA shown in the item 2(6) of Example 1.

Regarding the transformants of wells in which expression of anti-FGF-8 chimeric antibodies was found in the culture supernatants, the MTX concentration was increased by the same method as described above, and a transformant 5-D capable of growing in the Hybridoma-SFM-FBS(5) medium containing 1 mg/ml G418 and 200 nmol/l MTX at final concentrations and of highly expressing anti-FGF-8 chimeric antibody was obtained. Regarding the thus obtained transformant, cloning was carried out by limiting dilution method to obtain a transformed cell line showing the highest expression of anti-FGF-8 chimeric antibody. The thus obtained transformed cell was named KM3334.

(6) Binding Activity of Antibody to FGF-8 Peptide (ELISA)

Compound 1 (SEQ ID NO:15) was selected as human FGF-8 peptide with which the anti-FGF-8 antibody can react. In order to use in the activity measurement by ELISA, its conjugate with bovine serum albumin (BSA; manufactured by Nacalai Tesque) was prepared and used as the antigen. That is, 100 μl of 25 mg/ml SMCC [4-(N-maleimidomethyl) cyclohexane-1-carboxylic acid N-hydroxysuccinimide ester] (manufactured by Sigma)-DMSO solution was added dropwise under stirring to 900 μl of PBS solution containing 10 mg of BSA, followed by slowly stirring for 30 minutes. After 1 ml of the reaction solution was applied to a gel filtration column such as NAP-10 column which had been equilibrated with 25 ml of PBS, the eluate eluted with 1.5 ml of PBS was used as a BSA-SMCC solution. The BSA concentration of each fraction was measured based on the absorbance at 280 nm. Next, 200 μl of DMSO was added to 1.0 mg of Compound 1 which was then completely dissolved by adding 800 μl of PBS, the above BSA-SMCC solution (2.5 mg as BSA) added thereto under stirring, followed by slowly stirring at room temperature for 3 hours. The reaction solution was dialyzed overnight at 4° C. against PBS, sodium azide was added thereto to give a final concentration of 0.05%, the mixture was filtered through a 0.22 μm filter, and the filtrate was used as a BSA-compound 1 solution.

The conjugate prepared in the above was dispensed at 50 μl/well into a 96 well plate for ELISA (manufactured by Greiner) at a concentration of 0.5 to 1.0 μg/ml and allowed to stand for adsorption overnight at 4° C. After washing with PBS, 1% BSA-containing PBS (BSA-PBS) was added at 100 μl/well and allowed for blocking of remaining active groups to react at room temperature for 1 hour. After washing each well with 0.05% Tween-containing PBS (Tween-PBS), culture supernatants of transformants or purified antibodies were added at 50 μl/well and allowed to react at room temperature for 1 hour. After the reaction, each well was washed with Tween-PBS and then a peroxidase-labeled goat anti-human IgG (H & L) antibody solution (manufactured by American Qualex) diluted 3,000 to 6,000-folds with BSA-PBS was added as a secondary antibody solution at 50 μl/well and allowed to react at room temperature for 1 hour. After the reaction and subsequent washing with Tween-PBS, an ABTS substrate solution [a solution prepared by dissolving 0.55 g of 2,2'-azinobis(3-ethylbenzothiazoline-6-sulfonic acid) ammonium in 1 L of 0.1 M citrate buffer (pH 4.2) and adding 1 μl/ml hydrogen peroxide just before use] was added at 50 μl/well for color development, and the reaction was stopped by adding 5% SDS solution at 50 μl/well. Thereafter, absorbance at 415 nm (OD415) was measured.

3. Purification of Anti-FGF-8 Chimeric Antibody (1) Culturing of CHO-DG44 Cell-Derived Expression Cell and Purification of Antibody The anti-FGF-8 chimeric antibody-expressing transformed cell line KM3034 obtained in the item 2(4) of Example 1 was suspended in IMDM-dFBS(10) medium containing 500 nmol/l MTX to give a density of 1 to 2×10$^5$ cells/ml and dispensed at 40 ml into a 175 cm$^2$ flask (manufactured by Greiner). When the cells became confluent by culturing at 37° C. for 5 to 7 days in a 5% CO$_2$ incubator, the culture supernatant was discarded and the cells were washed with 20 ml of PBS. After discarding PBS and subsequently adding 40 ml of EXCELL301 medium (manufactured by JRH), the cells were cultured at 37° C. for 7 to 14 days in a 5% $CO_2$ incubator and then the culture supernatant was recovered. Using Prosep-A (manufactured by Millipore) column and according to the manufacture's instructions attached thereto, the anti-FGF-8 chimeric antibody was purified from the culture supernatant. The thus obtained anti-FGF-8 chimeric antibody was named KM3034.

(2) Culturing of YB2/0 Cell-Derived Expression Cells and Purification of Antibody The anti-FGF-8 chimeric antibody-expressing transformed cell line KM3334 obtained in the item 2(5) of Example 1 was cultured in Hybridoma-SFM (manufactured by Gibco) medium containing 200 nmol/l MTX and 5% in concentration of Daigo's GF21 (manufactured by Wako Pure Chemical Industries) at 37° C. in a 5% $CO_2$ incubator using a 175 cm² flask (manufactured by Greiner). Using Prosep-A (manufactured by Millipore) column and according to the manufacture's instructions attached thereto, the anti-EGF-8 chimeric antibody was purified from the culture supernatant which had been recovered after 8 to 10 days of the culturing. The thus obtained anti-FGF-8 chimeric antibody was named KM3334.

4. Analysis of Purified Anti-FGF-8 Chimeric Antibody

About 4 μg of each of the two anti-FGF-8 chimeric antibodies KM3034 and KM3334 expressed in respective animal cells, purified and obtained in the item 3 of Example 1 was subjected to SDS-PAGE according to the known method [*Nature*, 227, 680 (1970)] to analyze their molecular weights and purity. In each of the purified anti-FGF-8 chimeric antibodies, a single band of about 150 Kd in molecular weight was found under non-reducing conditions, and two bands of about 50 Kd and about 25 Kd were found under reducing conditions. These molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG type antibody has a molecular weight of about 150 Kd under non-reducing conditions and is degraded into H chains having a molecular weight of about 50 Kd and L chains having a molecular weight of about 25 Kd under reducing conditions due to cleavage of S—S bond in the molecule [*Antibodies: A Laboratory Manual*, Cold Spring Harbor Laboratory, Chapter 14 (1988); *Monoclonal Antibodies: Principles and Practice*, Academic Press Limited (1996)], so that it was confirmed that each anti-FGF-8 chimeric antibody was expressed and purified as an antibody molecule of correct structure.

5. Activity Evaluation of Purified Anti-FGF-8 Chimeric Antibodies

Figure 4:
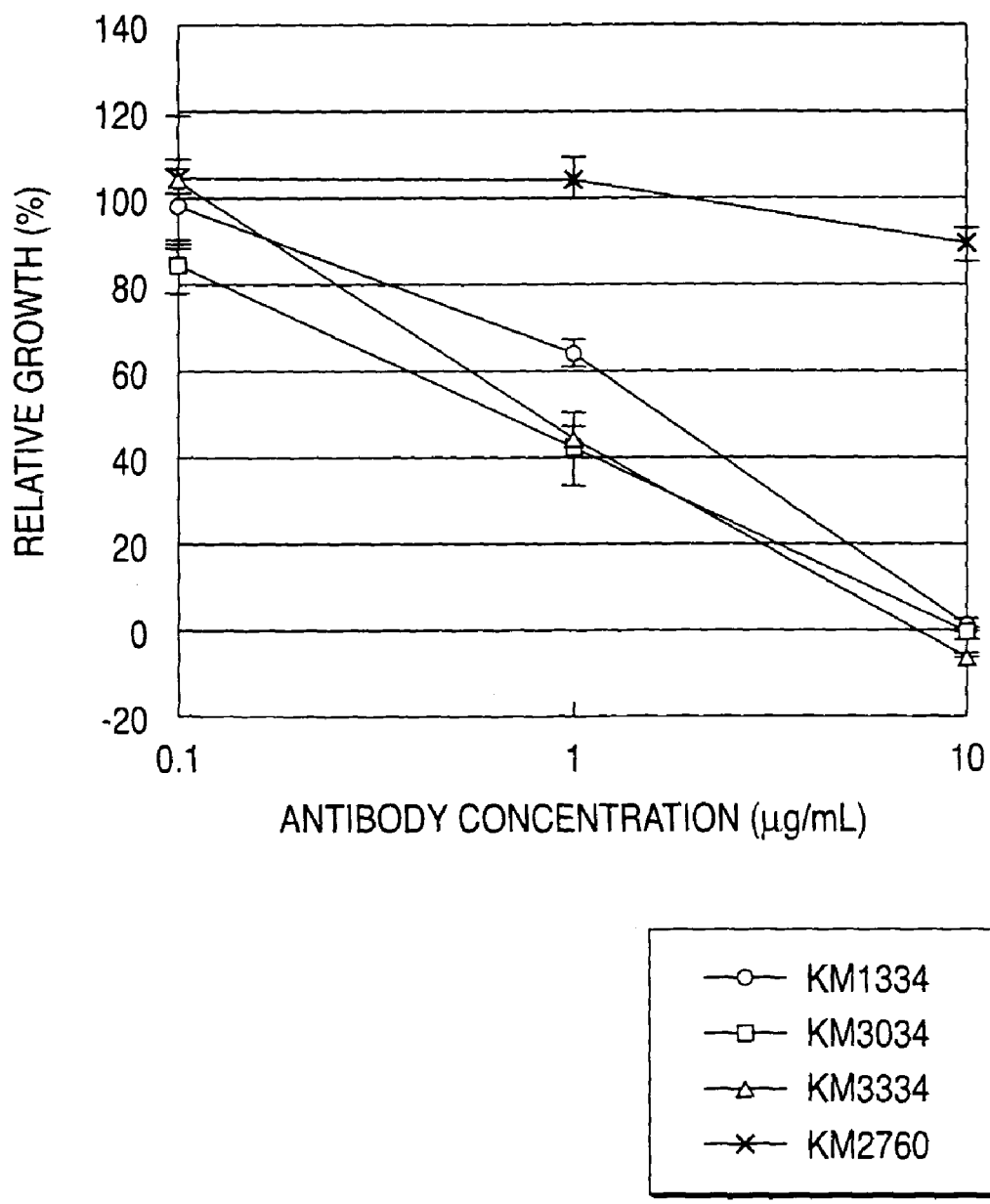
FIG. 4 shows neutralization activities of anti-FGF-8 mouse antibody KM1334 and anti-FGF-8 chimeric antibodies KM3034 and KM3334 on the FGF-8-dependent growth of mouse breast cancer cell line SC-3 cells. The abscissa and the ordinate indicate antibody concentration (μg/ml) and relative growth (%) when the growth by the addition of FGF-8 alone is defined as 100%, respectively. "○", "□", "Δ" and "x" indicate activities of KM1334, KM3034, KM3334 and KM2760 as a negative control, respectively.

FGF-8 neutralizing activity of purified anti-FGF-8 chimeric antibodies was evaluated by measuring the following FGF-8-dependent growth inhibitory effect of a mouse breast cancer cell line SC-3 [*Proc. Natl. Acad. Sci. USA*, 89, 8928 (1992)]. That is, the SC-3 cell was suspended at a density of $3.0\times10^4$ cells/ml in DMEM:Ham's F12 (1:1) medium (manufactured by Gibco) containing 2% activated carbon-treated FBS and inoculated at 150 μl ($4.5\times10^3$ cells)/well into a 96 well plate. After culturing at 37° C. for 18 hours in a 5% $CO_2$ incubator, the medium was exchanged by using 100 μl/well of a test medium. The test medium was prepared by dissolving 50 ng/ml FGF-8 (manufactured by R&D) and anti-FGF-8 chimeric antibody in each diluted concentration in DMEM: Ham's F12 (1:1) medium containing 0.1% BSA. Also, the chimeric antibody KM2760 for human chemokine receptor CCR4 described in WO01/64754 was used as a negative control antibody. After culturing at 37° C. for 48 hours in a 5% $CO_2$ incubator, the medium was exchanged with a freshly prepared test medium, followed by culturing for 48 hours. WST-1 reagent (manufactured by Roche) was added at 10 μl/well, followed by light stirring, and then $OD_{450/650}$ was measured after culturing at 37° C. for 1 hour in the 5% $CO_2$ incubator. In FIG. 4, the abscissa and the ordinate show the concentration of the added antibody and the relative growth (%) to the growth after addition of 50 ng/ml FGF-8 alone, respectively. The relative growth (%) to the growth after addition of 50 ng/ml FGF-8 alone was calculated by the following equation:

(Equation)

Relative growth (%) to the growth after addition of FGF-8 =

[(*OD* value after addition of FGF-8 and antibody) −

(*OD* value before addition of FGF-8 and antibody)] /

[(*OD* value after addition of FGF-8 alone) −

(*OD* value before addition of FGF-8 and antibody)] × 100

As shown in FIG. 4, each of the anti-FGF-8 mouse antibody KM1334 and anti-FGF-8 chimeric antibodies KM3034 and KM3334 showed similar SC-3 cell growth inhibitory activity so that reduction of the activity by chimeric antibody formation was not found.

Example 2

Preparation of Human CDR-Grafted Antibody for FGF-8;

1. Construction of cDNA Encoding VH and VL of Human CDR-Grafted Antibody Against FGF-8

(1) Design of Amino Acid Sequences of VH and VL of Human CDR-Grafted Antibody Against FGF-8

First, amino acid sequence of VH of a human CDR-grafted antibody against FGF-8 (anti-FGF-8 CDR-grafted antibody) was designed as follows. In order to graft the amino acid sequence of CDR in VH of the anti-FGF-8 mouse antibody KM1334 identified in the item 1(4) of Example 1, the amino acid sequence of FR in VH of a human antibody was selected. Kabat et al. have classified VH of various known human antibodies into three subgroups (HSG I to III) based on the homology of the amino acid sequences and then reported consensus sequences among respective subgroups [*Sequences of Proteins of Immunological Interest*, US Dep. Health and Human Services (1991)]. Since these consensus sequences have a possibility that the immunogenicity is reduced in human, it was decided to design the amino acid sequence of VH of an anti-FGF-8 CDR-grafted antibody based on these consensus sequences. In order to prepare an anti-FGF-8 CDR-grafted antibody having higher activity in designing it, it was decided to select the amino acid sequence of FR having the highest homology with the amino acid sequence of FR in VH of KM1334, among the amino acid sequences of FRs in consensus sequences of the three subgroups of VH of human antibodies. Results of the homology search are shown in Table 1. As shown in Table 1, the amino acid sequence of FR in the VH region of KM1334 showed the highest homology with the subgroup I.

TABLE 1

Homology between the amino acid sequence of FR in consensus sequence of each subgroup of human antibody VH and the amino acid sequence of FR in VH of KM1334

| HSG I | HSG II | HSG III |
|---|---|---|
| 79.3% | 51.7% | 59.8% |

Based on the above results, an amino acid sequence HV.0 of VH of the anti-FGF-8 CDR-grafted antibody describe in SEQ ID NO:16 was designed by grafting the amino acid sequence of CDR in VH of the anti-FGF-8 mouse antibody KM1334 to an appropriate position of the amino acid sequence of FR in the consensus sequence of subgroup 1 of VH of the human antibody.

Next, the amino acid sequence of VL of an anti-FGF-8 CDR-grafted antibody was designed as follows. In order to graft the amino acid sequence of CDR in VL of the anti-FGF-8 mouse antibody KM1334 identified in the item 1(4) of Example 1, the amino acid sequence of FR in VL of a human antibody was selected. Kabat et al. have classified the VL of various known human antibodies into four subgroups (HSG I to IV) based on the homology of the amino acid sequences and then reported consensus sequences among respective subgroups [*Sequences of Proteins of Immunological Interest*, US Dep. Health and Human Services (1991)]. Accordingly, similar to the case of VH, the amino acid sequence of FR having the highest homology with the amino acid sequence of FR in VL of KM1334 was selected from the amino acid sequences of FRs in consensus sequences of the four subgroups of VL of human antibodies.

Results of the homology search are shown in Table 2. As shown in Table 2, the amino acid sequence of FR in VL of KM1334 showed the highest homology with the subgroup II.

TABLE 2

Homology between the amino acid sequence of FR in consensus sequence of each subgroup of VL of human antibody and the amino acid sequence of FR in VL of KM1334

| HSG I | HSG II | HSG III | HSG IV |
|---|---|---|---|
| 66.3% | 83.8% | 66.2% | 73.8% |

Based on the above results, the amino acid sequence LV.0 of VL of the anti-FGF-8 CDR-grafted antibody shown in SEQ ID NO:17 was designed by grafting the amino acid sequence of CDR in VL of the anti-FGF-8 mouse antibody KM1334 to an appropriate position of the amino acid sequence of FR in the consensus sequence of subgroup II of VL of the human antibody.

The thus designed amino acid sequence HV.0 of VH and amino acid sequence LV.0 of VL of the anti-FGF-8 CDR-grafted antibody are sequences in which only the CDR amino acid sequence of the anti-FGF-8 mouse antibody KM1334 is grafted to the amino acid sequence of FR in the selected human antibody. In many cases, in the case of human CDR-grafted antibodies, the binding activity is decreased by grafting of the amino acid sequence of CDR in the mouse antibody alone. In order to avoid this reduction, among the amino acid residues in FR different between a human antibody and a mouse antibody, amino acid residues considered to have influences on the binding activity are grafted together with the amino acid sequence of CDR. Accordingly, an attempt was also made in this Example to identify the amino acid residues in FR considered to have influences on the binding activity.

First, a three-dimensional structure of an antibody V region comprising the amino acid sequence HV.0 of VH and the amino acid sequence LV.0 of VL of the anti-FGF-8 CDR-grafted antibody designed in the above (HV0LV0) was constructed by using computer modeling techniques. The preparation of three-dimensional structure coordinates was carried out by using software AbM (manufactured by Oxford Molecular), and the display of three-dimensional structure was carried out by using software Pro-Explore (manufactured by Oxford Molecular) or RasMol (manufactured by Glaxo) according to the respective manufacture's instructions attached thereto. Also, a computer model of the three-dimensional structure of the V region of anti-FGF-8 mouse antibody KM1334 was constructed in the same manner. In addition, a three-dimensional structure model of a modified antibody comprising an amino acid sequence in which amino acid residues different from anti-FGF-8 mouse antibody KM1334 in the amino acid sequences of FRs in VH and VL of HV0LV0 were substituted by the amino acid residues of positions corresponding to the anti-FGF-8 mouse antibody KM1334 in order, was constructed, and three-dimensional structures of V regions of the anti-FGF-8 mouse antibody KM1334, HV0 LV0 and modified structure were compared. As a result, as residues among the amino acid residues of FRs in HV0LV0 considered to have influences on the antibody activity by changing three-dimensional structure of the antigen-binding region, Lys at position 12, Lys at position 13, Ala at position 40, Pro at position 41, Met at position 48, Val at position 68, Ile at position 70, Thr at position 74, Thr at position 76, Glu at position 82, Arg at position 87 and Tyr at position 95 were selected for HV.0, and Ile at position 2, Val at position 3, Thr at position 14, Pro at position 15, Gln at position 50, Leu at position 51 and Tyr at position 92 were selected for LV.0, and used for the modification of amino acids. By changing at least one or more of these selected amino acid residues to the amino acid residues found in the mouse antibody KM1334, the VH and VL of human CDR-grafted antibodies having various modifications were designed as follows.

Specifically, the amino acid sequence shown in SEQ ID NO:18, in which 6 residues of Lys at position 12, Lys at position 13, Ala at position 40, Pro at position 41, Met at position 48 and Tyr at position 95 were changed to Ala, Arg, Arg, Ser, Ile and Phe, respectively, found in the mouse antibody KM1334, was designed as the VH. The amino acid sequence shown in SEQ ID NO:19, in which 6 residues of Ile at position 2, Thr at position 14, Pro at position 15, Gln at position 50, Leu at position 51 and Tyr at position 92 were changed to Val, Ser, Leu, Lys, Val and Phe, respectively, found in the mouse antibody KM1334, was designed as the VL.

(2) Construction of cDNA Encoding VH of Anti-FGF-8 CDR-Grafted Antibody

A cDNA encoding the anti-FGF-8 CDR-grafted antibody VH amino acid sequence HV.0 designed in the item 1(1) of Example 2 was constructed using PCR method in the following manner.

Firstly, the designed amino acid sequence was made into a full antibody amino acid sequence by ligating the secretory signal sequence of H chain of anti-FGF-8 mouse antibody KM1334 shown in SEQ ID NO:2. Next, the amino acid sequence was converted into genetic codons. When two or more genetic codons were present for one amino acid residue, corresponding genetic codon was determined by taking the codon usage found in nucleotide sequences of antibody genes into consideration [*Sequences of Proteins of Immunological Interest*, US Dept. Health and Human Services (1991)]. A nucleotide sequence of cDNA encoding the full antibody V region amino acid sequence was designed by ligating the thus determined genetic codons, and complementary nucleotide sequences of primers for use in the PCR amplification (including restriction enzyme recognition sequences for cloning into a humanized antibody expression vector) were added to the 5'-terminal and 3'-terminal. The thus designed nucleotide sequence was divided into sequences, each having 141 bases, from the 5'-terminal side, adjoining nucleotide sequences being designed such that the termini have an overlapping sequence of about 20 bases, and they were synthesized in alternating order of sense sequence and antisense sequence. Specifically, 4 synthetic oligonucleotides of SEQ ID NOs:20 to 23 were synthesized (manufactured by GENSET).

Each oligonucleotide was added to 50 µl of a reaction solution to give a final concentration of 0.1 µmol/l, and PCR was carried out by using 0.5 µmol/l M13 primer RV (manufactured by Takara Shuzo), 0.5µ mol/l M13 primer M4 (manufactured by Takara Shuzo) and 2.5 units of KOD polymerase (manufactured by TOYOBO) according to the manufacture's instructions attached to the KOD polymerase. Regarding the reaction conditions, the reaction solution was carried out by heating at 94° C. for 5 minutes, subsequent 25 cycles of the reactions at 94° C. for 30 seconds, 50° C. for 30 seconds 74° C. for 60 seconds as one cycle, and further heating at 74° C. for 5 minutes. The reaction solution was precipitated with ethanol, and the precipitate was dissolved in sterile water and reaction was carried out by using 10 units of a restriction enzyme EcoRI (manufactured by Takara Shuzo) and 10 units of a restriction enzyme SpeI (manufactured by Takara Shuzo) at 37° C. for 1 hour. The reaction solution was fractionated by agarose gel electrophoresis to collect about 0.3 µg of an EcoRI-SpeI fragment of about 0.47 kb.

Next, 3 µg of a plasmid pBluescript II SK(−) (manufactured by Stratagene) was allowed to react with 10 units of restriction enzyme EcoRI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2.9 µg of an EcoRI-SpeI fragment of about 2.95 kb.

Figure 5:
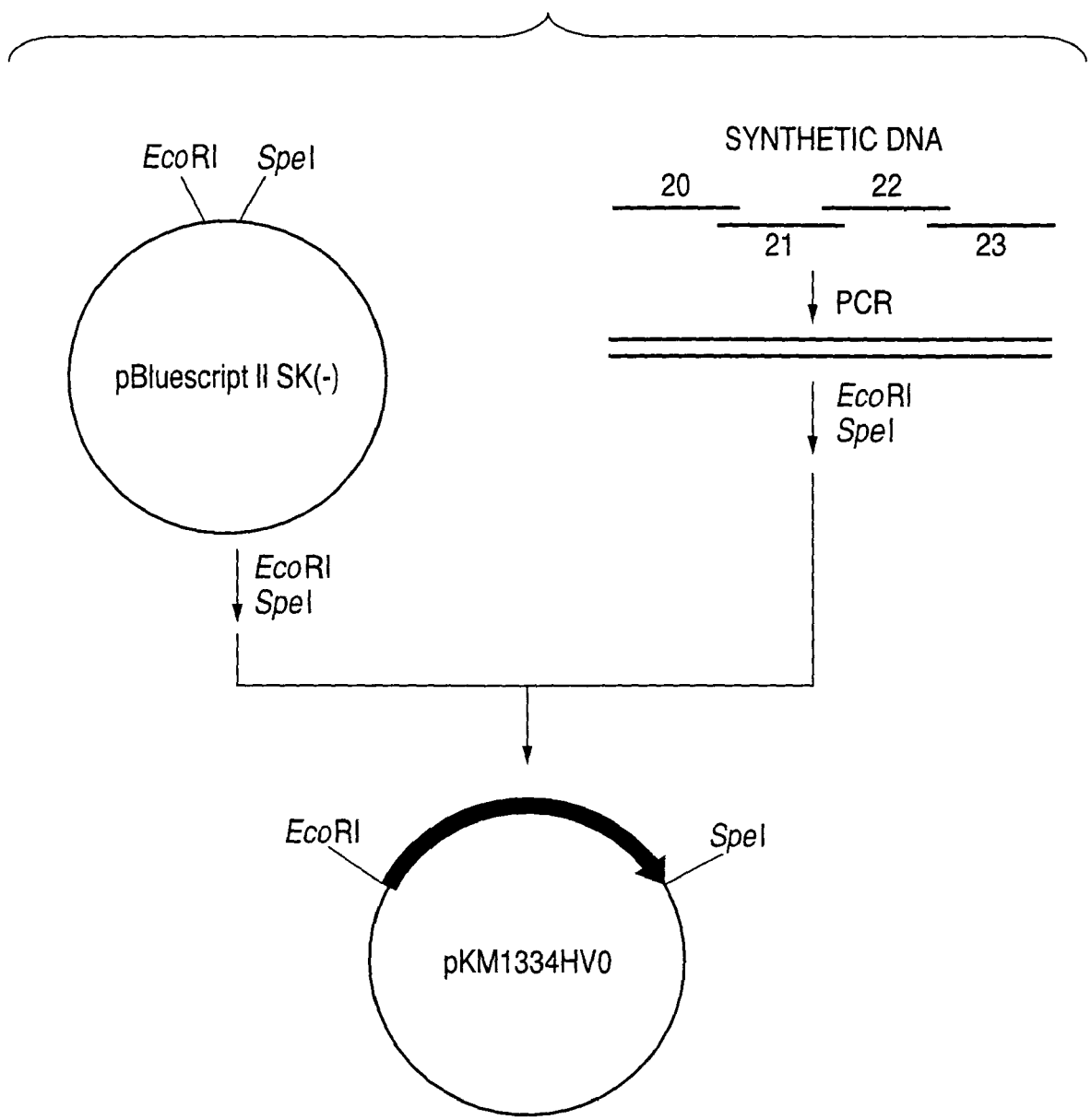
FIG. 5 shows construction steps of plasmid pKM1334HV0.

Next, 0.1 µg of the EcoRI-SpeI fragment of the PCR product of VH of the anti-FGF-8 CDR-grafted antibody and 0.1 µg of the EcoRI-SpeI fragment of the plasmid pBluescript II SK(−) both obtained in the above were added to 10 µl in total volume of sterile water and ligated using Ligation High (manufactured by TOYOBO). E. coli DH5α (manufactured by TOYOBO) was transformed by using the thus obtained recombinant plasmid DNA solution, each plasmid DNA was prepared from 10 clones of the transformants, and then nucleotide sequence analysis was carried out by the dideoxy method [*Molecular Cloning: A Laboratory Manual*, Cold Spring Harbor Lab. Press, New York (1989)] using Big Dye Terminator Kit ver. 2 (manufactured by Applied Biosystems). As a result of the nucleotide sequence analysis, a plasmid pKM1334HV0 shown in FIG. 5 having the nucleotide sequence of interest was obtained.

Also, a cDNA encoding the amino acid sequence HV.6 of VH of the anti-FGF-8 CDR-grafted antibody designed in the item 1(1) of Example 2 was constructed by PCR in the same manner as described above by using, as synthetic DNAs, 4 synthetic oligonucleotides of SEQ ID NOs:24 to 27 (manufactured by GENSET). As a result, a plasmid pKM1334HV6 containing HV.6-encoding cDNA was obtained.

(3) Construction of cDNA Encoding VL of Anti-FGF-8 CDR-Grafted Antibody

A cDNA encoding the amino acid sequence LV.0 of VL of the anti-FGF-8 CDR-grafted antibody designed in the item 1(1) of Example 2 was constructed by PCR in the same manner as in the case of VH. In this case, however, the anti-FGF-8 mouse antibody KM1334 L chain sequence shown in SEQ ID NO:4 was used as the secretory signal sequence, and 4 synthetic oligonucleotides of SEQ ID NOs: 28 to 31 (manufactured by GENSET) were used as synthetic DNAs. As a result, a plasmid pKM1334LV0 containing LV.0-encoding cDNA was obtained.

Also, a cDNA encoding the amino acid sequence LV.6 of VL of the anti-FGF-8 CDR-grafted antibody designed in the item 1(1) of Example 2 was constructed by PCR in the same manner as described above by using 4 synthetic oligonucleotides of SEQ ID NOs:32 to 35 (manufactured by GENSET) as synthetic DNAs. As a result, a plasmid pKM1334LV6 containing LV 6-encoding cDNA was obtained.

2. Construction of Anti-FGF-8 CDR-Grafted Antibody Expression Vector

Using the pKANTEX93 for humanized antibody expression described in WO97/10354 and the plasmids pKM1334HV0 and pKM1334LV4 obtained in the items 1(2) and 1(3) of Example 2, an anti-FGF-8 CDR-grafted antibody expression vector pKANTEX1334HV0LV0 was constructed in the following manner.

A reaction was carried out by mixing 3 µg of the plasmid pKM1334HV0 obtained in the item 1(2) of Example 2 with 10 units of restriction enzyme ApaI (manufactured by Takara Shuzo) and 10 units of restriction enzyme NotI (manufactured by Takara Shuzo) at 37° C. for 1 hour. The reaction solution was fractionated by agarose gel electrophoresis to collect about 0.3 µl of an ApaI-NotI fragment of about 0.47 kb.

Next, 3 µg of the humanized antibody expression vector pKANTEX93 was allowed to react with 10 units of restriction enzyme ApaI (manufactured by Takara Shuzo) and 10 units of restriction enzyme NotI (manufactured by Takara Shuzo) at 37° C. for 1 hour. The reaction solution was fractionated by agarose gel electrophoresis to collect about 2 µg of an ApaI-NotI fragment of about 12.8 kb.

Figure 6:
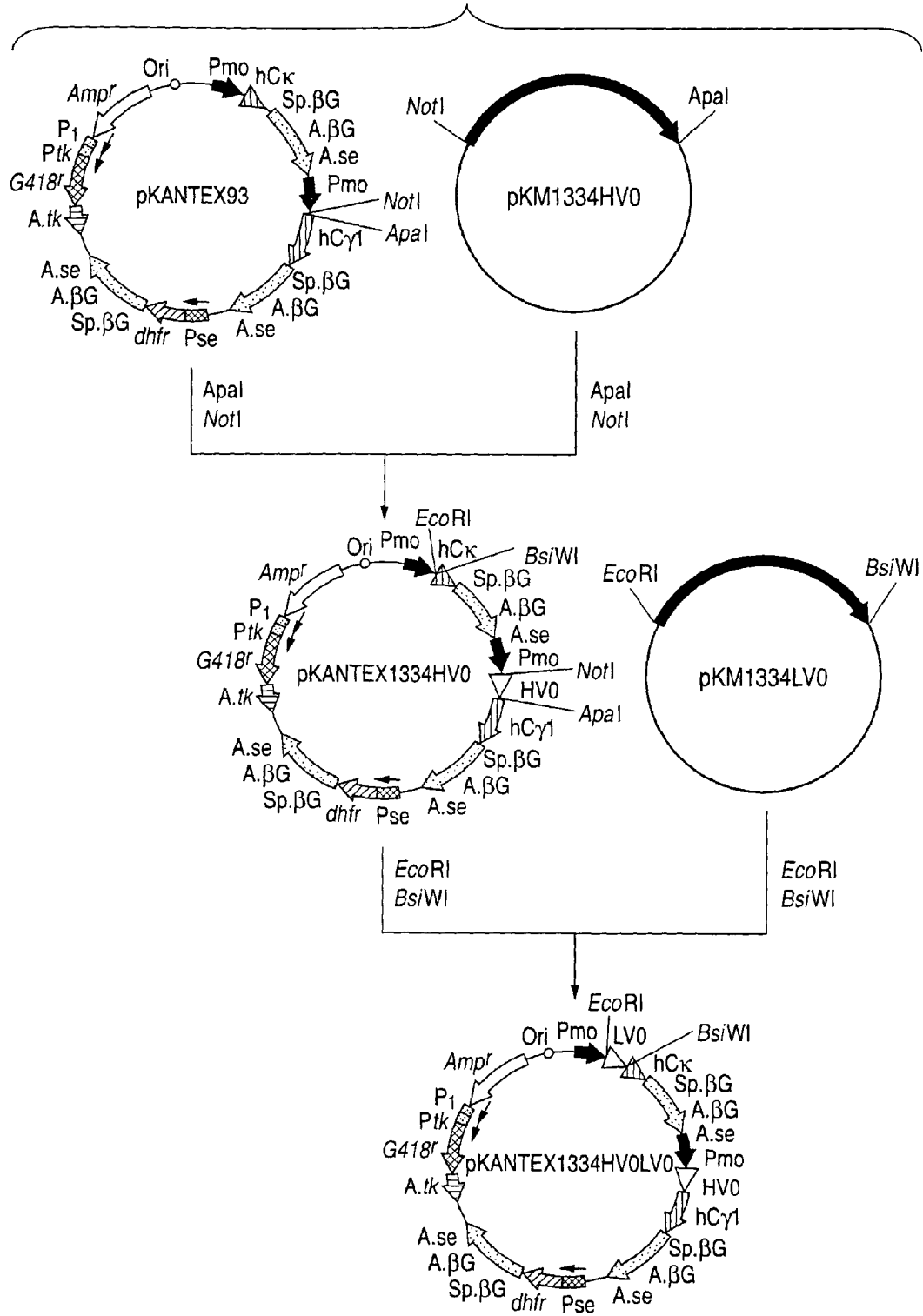
FIG. 6 shows construction steps of plasmid pKANTEX1334HV0LV0.

Next, 0.1 µg of the NotI-ApaI fragment derived from the plasmid pKM1334HV0 and 0.1 µg of the NotI-ApaI fragment derived from the plasmid pKANTEX93 were added to 10 µl in total volume of sterile water and ligated using Ligation High (manufactured by TOYOBO). Using the thus obtained recombinant plasmid DNA solution, E. coli DH5α was transformed to obtain a plasmid pKANTEX1334HV0 shown in FIG. 6.

Next, 3 µg of the plasmid pKM1334LV0 obtained in the item 1(3) of Example 2 was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 0.3 µg of an EcoRI-BsiWI fragment of about 0.45 kb.

Next, 3 µg of the plasmid pKANTEX1334HV0 obtained in the above was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 2 µg of an EcoRI-BsiWI fragment of about 13.30 kb.

Next, 0.1 µg of the EcoRI-BsiWI fragment derived from the plasmid pKM1334LV0 and 0.1 µg of the EcoRI-BsiWI fragment derived from the plasmid pKANTEX1334HV0 were added to 10 µl in total volume of sterile water and ligated by using Ligation High (manufactured by TOYOBO). Using the thus obtained recombinant plasmid DNA solution, the *E. coli* strain DH5α was transformed to obtain a plasmid pKANTEX1334HV0LV0 shown in FIG. 6.

Using 400 ng of the thus obtained plasmid, its nucleotide sequence was analyzed by the dideoxy method [*Molecular Cloning: A Laboratory Manual*, Cold Spring Harbor Lab. Press, New York (1989)] using Big Dye Terminator Kit ver. 2 (manufactured by Applied Biosystems) to thereby confirm that a plasmid into which the DNA of interest had been cloned was obtained.

Also, an expression vector pKANTEX1334HV0LV6 was constructed in the same manner as described above by using the plasmid pKM1334HV0 obtained in the item 1(2) of Example 2 and the plasmid pKANTEX1334LV6 obtained in the item 1(3) of Example 2.

In addition, an expression vector pKANTEX1334HV6LV6 was constructed by the same method described above using the plasmid pKM1334HV6 obtained in the item 1(2) of Example 2 and the plasmid pKANTEX1334LV6 obtained in the item 1(3) of Example 2.

3. Stable Expression of Anti-FGF-8 CDR-Grafted Antibody using YB2/0 Cell

Using the anti-FGF-8 CDR-grafted antibody expression vectors pKANTEX1334HV0LV0, pKANTEX1334HV0LV6 and pKANTEX1334HV6LV6 obtained in the item 2 of Example 2, stable expression of various anti-FGF-8 CDR-grafted antibodies in YB2/0 cell was carried out in accordance with the method described in the item 2(5) of Example 1.

4. Purification of Anti-FGF-8 CDR-Grafted Antibody

Culturing of transformants derived from YB2/0 cell expressing various anti-FGF-8 CDR-grafted antibodies obtained in the item 3 of Example 2 and purification of anti-FGF-8 CDR-grafted antibodies from culture supernatants were carried out according to the method described in the item 3(2) of Example 1. An antibody derived from a pKANTEX1334,HV0LV0-introduced transformant was named HV0LV0, an antibody derived from a pKANTEX1334.HV0LV6-introduced transformant was named HV0LV6 and an antibody derived from a pKANTEX1334HV6LV6-introduced transformant was named HV6LV6.

5. Analysis of Purified Anti-FGF-8 CDR-Grafted Antibodies

SDS-PAGE of various anti-FGF-8 CDR-grafted antibodies obtained in the item 4 of Example 2 was carried out in accordance with the method described in the item 4 of Example 1. As a result, it was confirmed that each antibody was expressed and purified as an antibody molecule of correct structure.

6. Measurement of Binding Activity of Anti-FGF-8 CDR-Grafted Antibody Against FGF-8 (ELISA)

Figure 7:
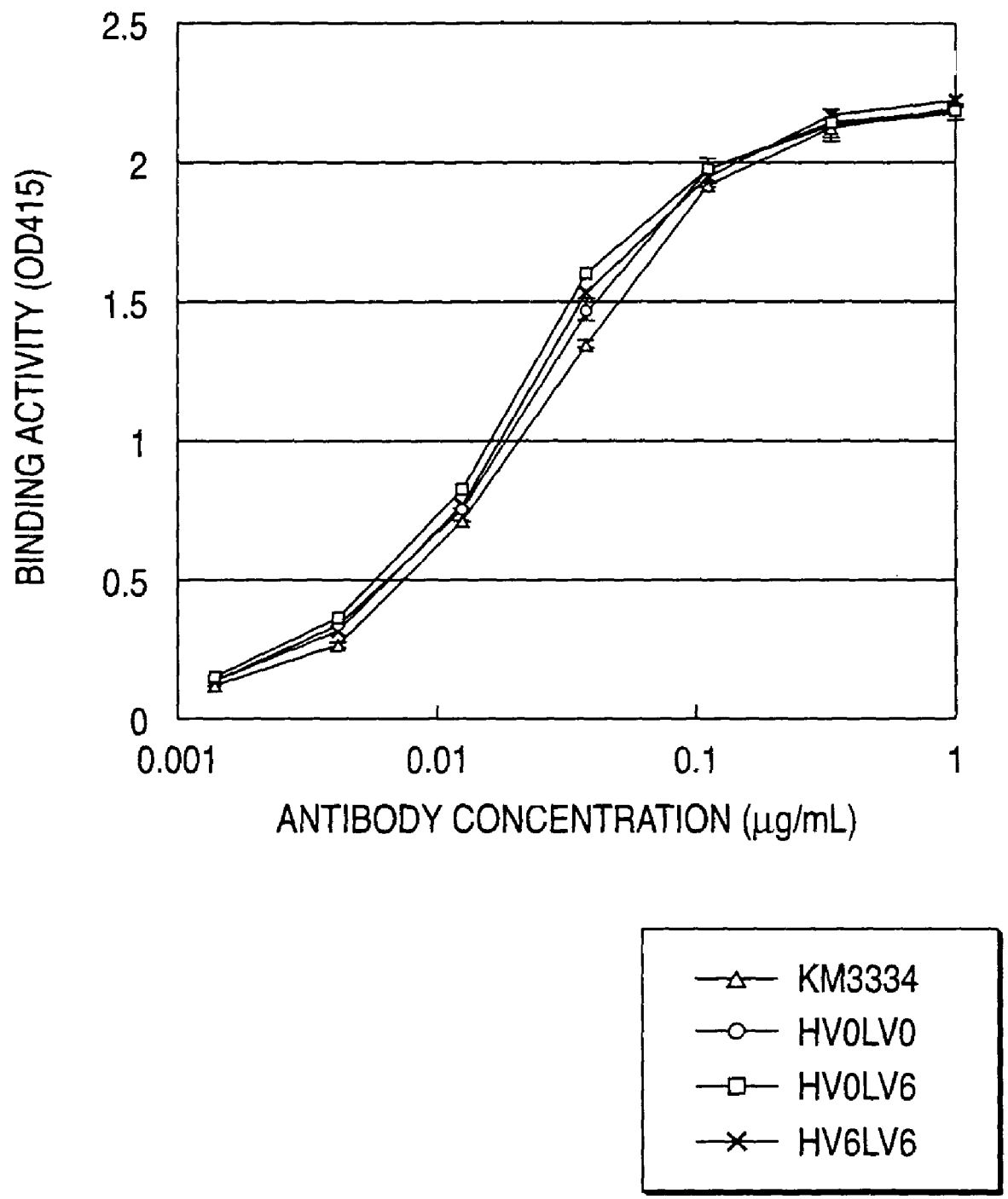
FIG. 7 shows results of the ELISA measurement of the FGF-8 binding activities of anti-FGF-8 chimeric antibody KM3334 and anti-FGF-8 CDR-grafted antibodies HV0LV0, HV0LV6 and HV6LV6. The abscissa and the ordinate show antibody concentration (μg/ml) and binding activity (OD415), respectively. "○", "□" "Δ" and "x" indicate activities of KM3334, HV0LV0, HV0LV6 and HV6LV6, respectively.

The activity of various anti-FGF-8 CDR-grafted antibodies obtained in the item 4 of Example 2 to bind to FGF-8 was measured by the ELISA described in the item 2(6) of Example 1. The YB2/0-derived anti-FGF-8 chimeric antibody KM3334 obtained in the item 3(2) of Example 1 was used as a positive control. The results are shown in FIG. 7. As shown in FIG. 7, each of the anti-FGF-8 CDR-grafted antibodies showed an FGF-8 binding activity similar to that of KM3334, so that significant reduction of the binding activity caused by the CDR grafting was not observed.

7. Measurement of Binding Activity of Anti-FGF-8 CDR-Grafted Antibodies for FGF-8

In order to examine the activity of various anti-FGF-8 CDR-grafted antibodies obtained in the item 4 of Example 2 to bind to FGF-8 in more detail, activities of various anti-FGF-8 CDR-grafted antibodies to bind to FGF-8 were measured and compared as follows by using BIAcore 2000 (manufactured by BIACORE). The YB2/0-derived anti-FGF-8 chimeric antibody KM3334 obtained in the item 3(2) of Example 1 was used as a positive control.

Hereinafter, HBS-EP (manufactured by BIACORE) was used as the buffer for dilution of samples and during the measurement. First, a sensor tip CM5 (manufactured by BIACORE) was set, and FGF-8 (manufactured by R&D) dissolved to give a concentration of 31.25 µg/ml by using 10 mmol/l acetate buffer (pH 4.0) was immobilized on the sensor tip surface by an amine coupling method. The immobilized amount was 4,498 RU.

Figure 8:
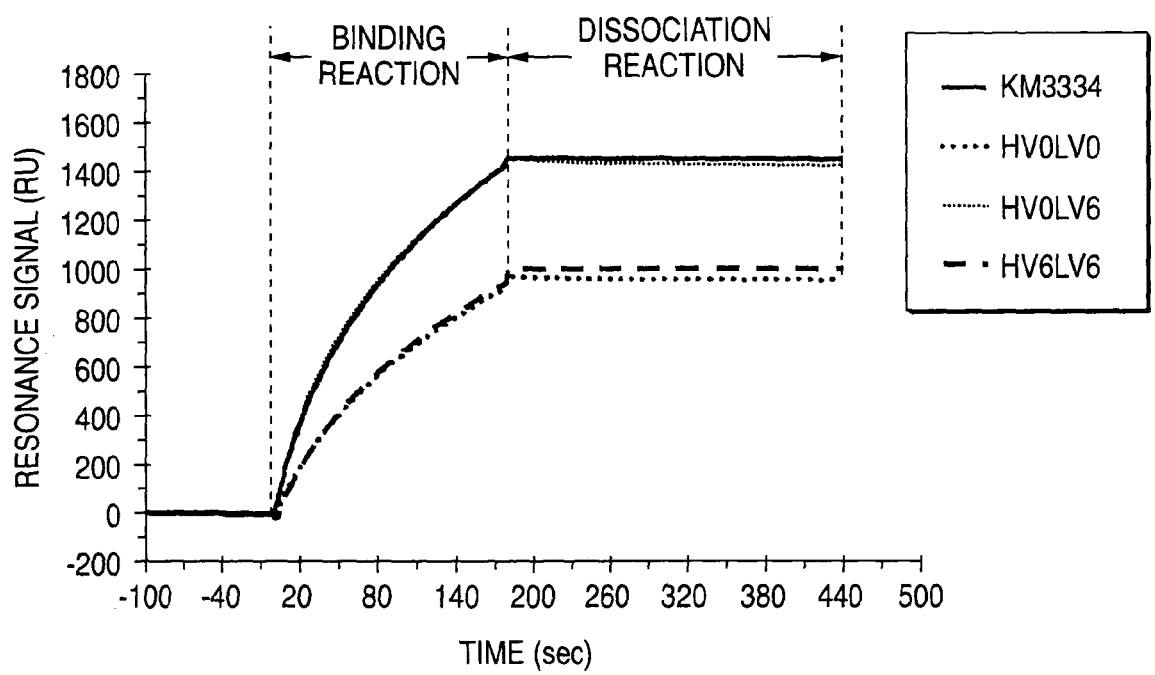
FIG. 8 shows results of the BIAcore 2000 measurement of the FGF-8 binding activities of anti-FGF-8 chimeric antibody KM3334 and anti-FGF-8 CDR-grafted antibodies HV0LV0, HV0LV6 and HV6LV6. The abscissa and the ordinate show time (seconds) and resonance signal (RU), respectively.

To the FGF-8 immobilized flow cell, 60 µl of each antibody solution was added at a flow rate of 20 µl/minute, and then the dissociation reaction was monitored for 3 minutes. After the dissociation reaction, the tip surface was regenerated by adding 20 µl of 10 mol/l Glycine-HCl buffer (pH 1.5) continuously twice to the flow cell. This cycle was carried out for antibody solutions of various concentrations (50 to 0.068 µg/ml), and a sensorgram at each concentration was obtained. The sensorgram of each antibody was made into a sensorgram of specific reaction by subtracting a sensorgram obtained using a chimeric antibody KM871 for GD3 [*Cancer Immunol. Immunother.*, 36, 373 (1993)] as a negative control. The sensorgram of 50 µg/ml of each antibody is shown in FIG. 8. As is apparent from the sensorgram, dissociation was hardly observed at the time of the dissociation reaction of each antibody, so that it was difficult to obtain an accurate dissociation constant. Accordingly, comparison of the binding activity of various antibodies was carried out by comparing heights of binding [resonance signal (RU)] at the time of the binding reaction. As a result, as shown in FIG. 8, the chimeric antibody KM3334 showed the highest binding reaction, and the CDR-grafted antibody HV0LV6 showed a high binding reaction similar to that of KM3334. On the other hand, the CDR-grafted antibodies HV0LV0 and HV6LV6 showed a slightly lower binding reaction than KM3334 and HV0LV6. The above results show that comparison of binding activities between antibodies which could not be recognized by ELISA is possible by the use of BIAcore and that binding activity of CDR-grafted antibody is recovered to the same level of chimeric antibody by the modification of 6 amino acid residues of FR of VL. In addition, the effect on the increase of binding activity was not recognized on the 6 amino acid residues of FR of VH.

The YB2/0 cell-derived CDR-grafted antibody HV0LV6 which showed a high binding reaction similar to that of the chimeric antibody KM3334 was named KM8037, and the YB2/0 cell-derived transformed cell line highly expressing KM8037 was also named KM8037. Also, the transformed cell line KM8037 has been deposited on Jun. 20, 2002, as FERM BP-8084 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

Example 3

Preparation of Anti-FGF-8 CDR-Grafted Antibody Having Lower Immunogenicity (1)

It was revealed from the results of Example 2 that the anti-FGF-8 CDR-grafted antibody having modification of 6 amino acid residues derived from the mouse antibody KM1334, in FR of VL, shows a binding activity similar to that of the corresponding chimeric antibody. Accordingly, the effect of these 6 residues on the recovery of the activity was further examined, and anti-FGF-8 CDR-grafted antibodies which have sufficient activity and contain smaller number of mouse antibody-derived amino acid residues and are expected to have more reduced immunogenicity were prepared as follows.

1. Design of Amino Acid Sequence of VL

Regarding the above 6 amino acid residues, amino acid sequences of 6 VLs having the following modifications were designed.

In LV.4-1, 4 residues of Ile at position 2, Gln at position 50, Leu at position 51 and Tyr at position 92 were changed to Val, Lys, Val and Phe, respectively, which are amino acid residues found in the mouse antibody KM1334.

In LV.4-2, 4 residues of Ile at position 2, Thr at position 14, Pro at position 15 and Tyr at position 92 were changed to Val, Ser, Leu and Phe, respectively, which are amino acid residues found in the mouse antibody KM1334.

In LV.3-1, 3 residues of Ile at position 2, Leu at position 51 and Tyr at position 92 were changed to Val, Val and Phe, respectively, which are amino acid residues found in the mouse antibody KM1334.

In LV.3-2, 3 residues of Thr at position 14, Pro at position 15 and Tyr at position 92 were changed to Ser, Leu and Phe, respectively, which are amino acid residues found in the mouse antibody KM1334.

In LV.2-1, 2 residues of Leu at position 51 and Tyr at position 92 were changed to Val and Phe, respectively, which are amino acid residues found in the mouse antibody KM1334.

In LV.2-2, 2 residues of Ile at position 2 and Tyr at position 92 were respectively changed to Val and Phe, respectively, which are amino acid residues found in the mouse antibody KM1334.

2. Construction of CDNA Encoding VL

The cDNAs encoding respective anti-FGF-8 CDR-grafted antibody VL amino acid sequences designed in the item 1 of Example 3 were constructed as follows.

(1) Construction of cDNA Encoding LV.4-1

The cDNA encoding LV.4-1 was constructed in accordance with the method described in the item 1(3) of Example 2, using four synthetic oligonucleotides of SEQ ID NOs:29, 32, 34 and 35 as synthetic DNA fragments (manufactured by GENSET). As a result, a plasmid pKM1334LV4-1 containing a CDNA encoding LV.4-1 was obtained.

(2) Construction of cDNA Encoding LV.3-1

Using 50 ng of the plasmid pKM1334LV6 obtained in the item 1(3) of Example 2 as the template, M13 primer RV (manufactured by Takara Shuzo) and the synthetic DNA having the nucleotide sequence describe in SEQ ID NO:38 (manufactured by GENSET) were added as primers to give a final concentration of 0.3 µmol/Lol/L, PCR was carried out according to the manufacture's instructions attached to KOD polymerase (manufactured by TOYOBO) by first heating at 94° C. for 2 minutes and subsequent 35 cycles of reactions at 94° C. for 15 seconds, 50° C. for 30 seconds and 68° C. for 1 minute as one cycle. The reaction solution was purified, the product was dissolved in sterile water, and a reaction was carried out by adding 10 units of a restriction enzyme KpnI (manufactured by Takara Shuzo) and 10 units of a restriction enzyme SpeI (manufactured by Takara Shuzo) thereto at 37° C. for 1 hour. The reaction solution was fractionated by agarose gel electrophoresis to collect about 0.3 µg of a KpnI-SpeI fragment of about 0.22 kb.

Next, 3 µg of the plasmid pKM1334LV4-1 obtained in the item 2(1) of Example 3 was allowed to react with 10 units of restriction enzyme KpnI (manufactured by Takara Shuzo) at 37° C. for 1 hour. The reaction solution was fractionated by agarose gel electrophoresis to collect about 0.2 µg of a KpnI-KpnI fragment of about 0.21 kb.

Next, 3 µg of the plasmid pBluescript II SK(−) was allowed to react 10 units of restriction enzyme KpnI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2 µg of a KpnI-SpeI fragment of about 2.95 kb.

Figure 9:
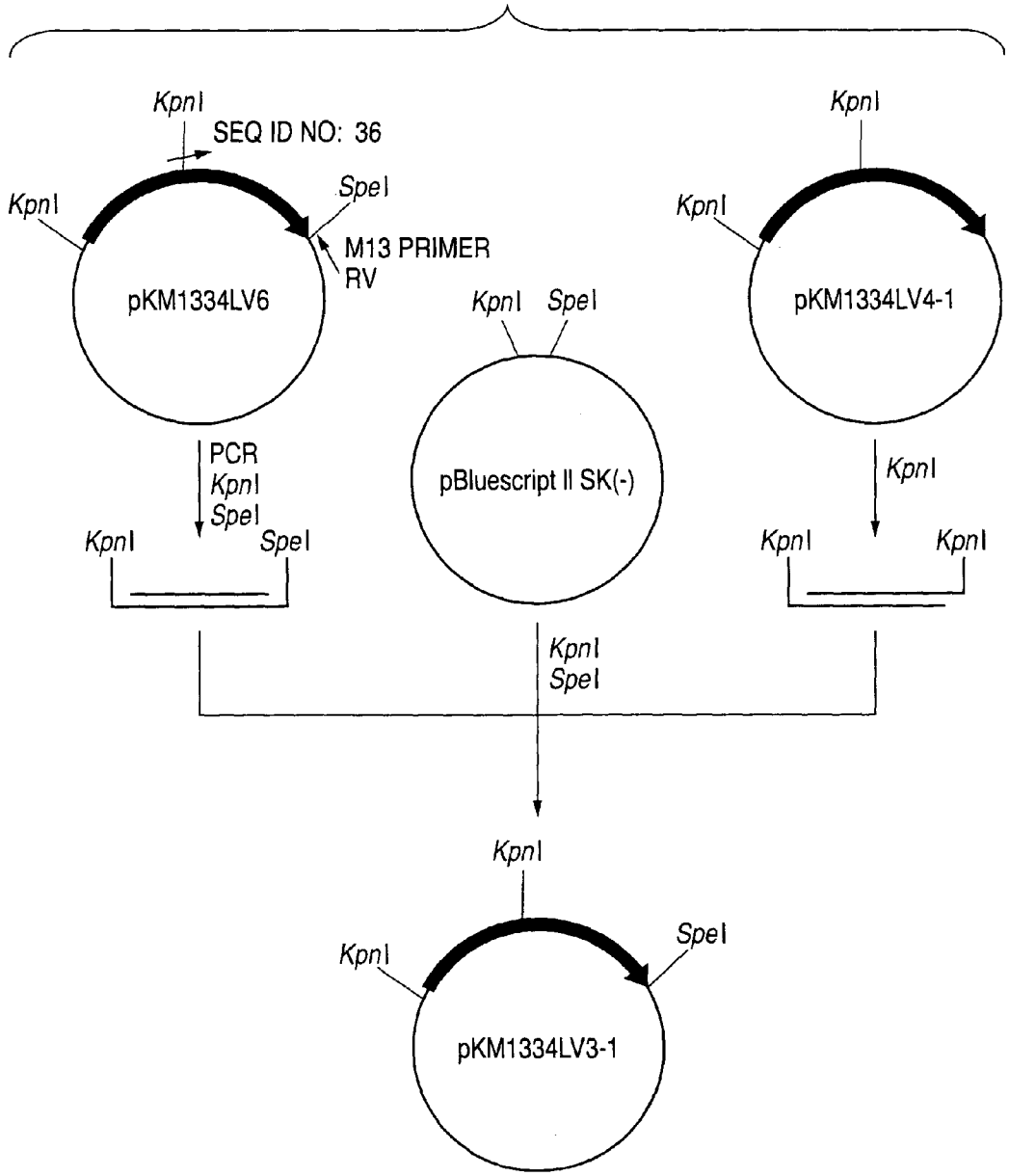
FIG. 9 shows construction steps of plasmid pKM1334LV3-1.

To 10 µl in total volume of sterile water, 0.1 µg of the KpnI-SpeI fragment of the VL cDNA, 0.1 µg of the KpnI-KpnI fragment derived from the plasmid pKM1334LV4-1 and 0.1 µg of the KpnI-SpeI fragment of the plasmid pBluescript II SK(−) each obtained in the above were added and ligated by using Ligation High (manufactured by TOYOBO). E. coli DH5α was transformed by using the thus obtained recombinant plasmid DNA solution to obtain a plasmid pKM1334LV3-1 shown in FIG. 9 containing a cDNA encoding the LV.3-1.

(3) Construction of cDNA Encoding LV.2-1

A plasmid pKM1334LV2-1 containing a cDNA encoding the LV.2-1 was obtained by a method similar to that described in the item 2(1) of Example 2, except that the plasmid pKM1334LV0 obtained in the item 1(3) of Example 2 was used instead of the plasmid pKM1334LV4-1.

(4) Construction of cDNA Encoding LV.2-2

A plasmid pKM1334LV2-2 containing a cDNA encoding the LV.2-2 was obtained by a method similar to that described in the item 2(1) of Example 2, except that the synthetic DNA shown in SEQ ID NO:37 was used instead of the synthetic DNA shown in SEQ ID NO:36 as a primer.

(5) Construction of cDNA Encoding LV.4-2

A reaction was carried out by mixing 3 µg of the plasmid pKM1334LV2-2 obtained in the item 2(4) of Example 5 with 10 units of restriction enzyme KpnI (manufactured by Takara Shuzo) at 37° C. for 1 hour. The reaction solution was fractionated by agarose gel electrophoresis to collect about 2 µg of a KpnI-KpnI fragment of about 3.16 kb.

Next, 3 µg of the plasmid pKM1334LV6 obtained in the item 1(3) of Example 2 was allowed to react with 10 units of restriction enzyme KpnI (manufactured by Takara Shuzo) at 37° C. for 1 hour. The reaction solution was fractionated by agarose gel electrophoresis to collect about 0.2 µg of a KpnI-KpnI fragment of about 0.21 kb.

Figure 10:
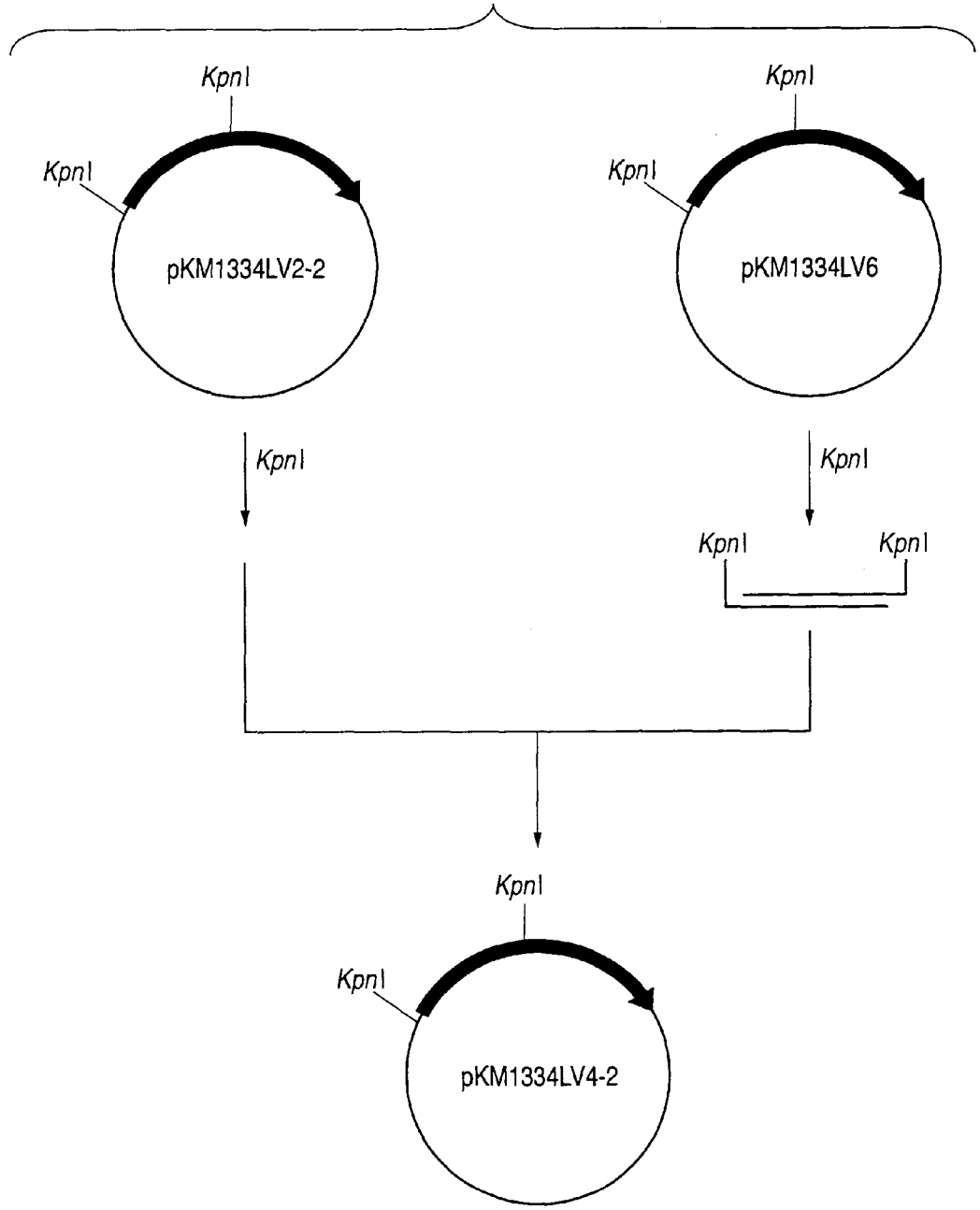
FIG. 10 shows construction steps of plasmid pKM 1334LV4-2.

To 10 µl in total volume of sterile water, 0.1 µg of the KpnI-KpnI fragment derived from the plasmid pKM1334LV2-2 and 0.1 µg of the KpnI-KpnI fragment derived from the plasmid pKM1334LV6 each obtained in the above were added and ligated by using Ligation High (manufactured by TOYOBO). E. coli DH5α was transformed by using the thus obtained recombinant plasmid DNA solution to obtain the plasmid pKM1334LV4-2 shown in FIG. 10 containing a cDNA encoding the LV.4-2.

(6) Construction of cDNA Encoding LV.3-2

A reaction was carried out by mixing 3 µg of the plasmid pKM1334LV4-2 obtained in the item 2(5) of Example 3 with 10 units of restriction enzymes Tth111I (manufactured by Takara Shuzo) and XmnI (manufactured by New England Biolabs) at 37° C. for 1 hour. The reaction solution was fractionated by agarose gel electrophoresis to collect about 2 µg of a Tth111I-XmnI fragment of about 2.24 kb.

Next, 3 µg of the plasmid pKM1334LV0 obtained in the item 1(3) of Example 2 was allowed to react with 10 units of restriction enzymes Tth111I (manufactured by Takara Shuzo) and XmnI (manufactured by New England Biolabs) at 37° C. for 1 hour. The reaction solution was fractionated by agarose gel electrophoresis to collect about 1 µg of a Tth111I-XmnI fragment of about 1.11 kb.

Figure 11:
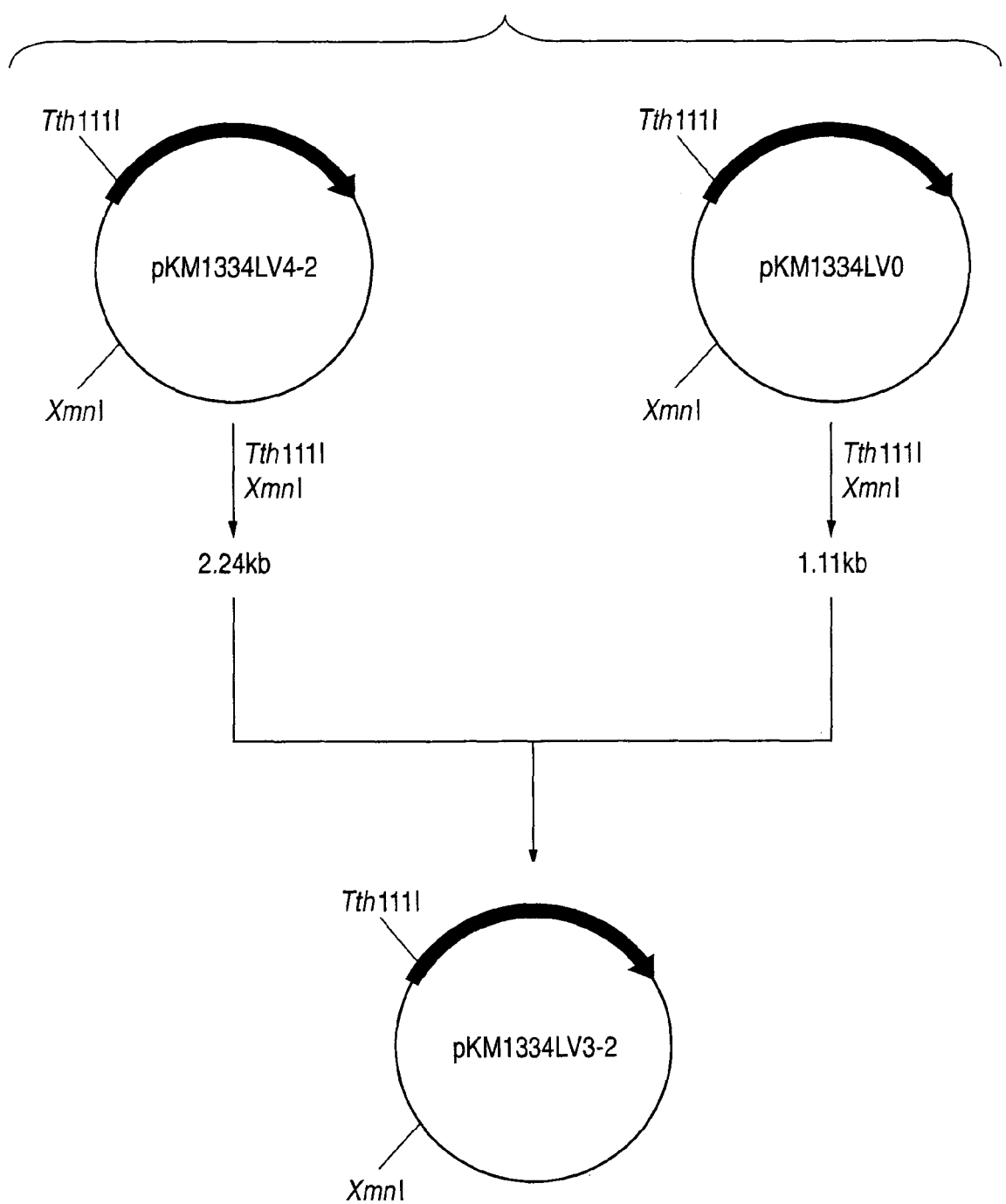
FIG. 11 shows construction steps of plasmid pKM1334LV3-2.

To 10 µl in total volume of sterile water, 0.1 µg of the Tth111I-XmnI fragment derived from the plasmid pKM1334LV4-2 and 0.1 µg of the Tth111I-XmnI fragment derived from the plasmid pKM1334LV0 each obtained in the above were added and ligated by using Ligation High (manufactured by TOYOBO). *E. coli* DH5α was transformed by using the thus obtained recombinant plasmid DNA solution to obtain a plasmid pKM1334LV3-2 shown in FIG. 11 containing a cDNA encoding the LV0.3-2.

3. Construction of Anti-FGF-8 CDR-Grafted Antibody Expression Vector

Various VL cDNA-containing anti-FGF-8 CDR-grafted antibody expression vectors were constructed by replacing the EcoRI-BsiWI fragment containing the VL cDNA of the expression vector pKANTEX1334HV0LV6 obtained in the item 2 of Example 2 by each of the various VL cDNA-containing EcoRI-BsiWI fragments constructed in the item 2 of Example 3. Specifically, 6 vectors pKANTEX1334HV0LV4-1, pKANTEX1334HV0LV4-2, pKANTEX1334HV0LV3-1, pKANTEX1334HV0LV3-2, pKANTEX1334HV0LV2-1 and pKANTEX1334HV0LV2-2 were constructed.

4. Stable Expression of Anti-FGF-8 CDR-Grafted Antibody using CHO/DG44 Cell

Stable expression of various anti-FGF-8 CDR-grafted antibodies in CHO/DG44 cell was carried out in accordance with the method described in the item 2(4) of Example 1, using the anti-FGF-8 CDR-grafted antibody expression vectors pKANTEX1334HV0LV0 and pKANTEX1334HV0LV6 obtained in the item 2 of Example 2 and the various anti-FGF-8 CDR-grafted antibody expression vectors obtained in the item 3 of Example 3.

5. Purification of Anti-FGF-8 CDR-Grafted Antibody

Culturing of CHO/DG44 cell-derived transformants expressing various anti-FGF-8 CDR-grafted antibodies obtained in the item 4 of Example 3 and purification of the anti-FGF-8 CDR-grafted antibodies from culture supernatants were carried out in accordance with the method described in the item 3(1) of Example 1. An antibody derived from a pKANTEX1334HV0LV0-introduced transformant was named HV0LV0/CHO, an antibody derived from a pKANTEX1334HV0LV6-introduced transformant was named HV0LV6/CHO, an antibody derived from a pKANTEX1334HV0LV4-1-introduced transformant was named HV0LV4-1/CHO, an antibody derived from a pKANTEX1334HV0LV4-2-introduced transformant was named HV0LV4-2/CHO, an antibody derived from a pKANTEX1334HV0LV3-1-introduced transformant was named HV0LV3-1/CHO, an antibody derived from a pKANTEX1334HV0LV3-2-introduced transformant was named HV0LV0/CH3-2, an antibody derived from a pKANTEX1334HV0LV2-1-introduced transformant was named HV0LV201/CHO and an antibody derived from a pKANTEX1334HV0LV2-2-introduced transformant was named HV0LV2-2/CHO.

6. Analysis of Purified Anti-FGF-8 CDR-Grafted Antibody

SDS-PAGE of various anti-FGF-8 CDR-grafted antibodies obtained in the item 5 of Example 3 was carried out in accordance with the method described in the item 4 of Example 1. As a result, it was confirmed that each antibody was expressed and purified as an antibody molecule of correct structure.

7. Measurement of Binding Activity of Anti-FGF-8 CDR-Grafted Antibody Against FGF-8 (BIAcore Biosensor)

In order to examine the activity of various anti-FGF-8 CDR-grafted antibodies obtained in the item 5 of Example 3 to bind to FGF-8 in more detail, activities of various anti-FGF-8 CDR-grafted antibodies to bind to FGF-8 were measured and compared as follows by using BIAcore 2000 (manufactured by BIACORE). The CHO/DG44-derived anti-FGF-8 chimeric antibody KM3034 obtained in the item 3(1) of Example 1 was used as a positive control.

Hereinbelow, HBS-EP (manufactured by Pharmacia) was used as the buffer solution for dilution of samples and during the measurement. First, a sensor tip SA (manufactured by BIACORE) was set, and 5 µl of a C-terminus-biotin labeled compound 1 (an N-terminus peptide of FGF-8; SEQ ID NO:15) prepared to a solution of 0.05 µg/ml was added thereto at a flow rate of 20 µl/minute. Thereafter, the tip surface was washed by adding 5 µl of 10 mmol/l Glycine-HCl buffer (pH 1.5) continuously twice. Immobilized amount of the FGF-8 peptide was 35 RU.

To the FGF-8 peptide immobilized flow cell, 60 µl of each antibody solution was added at a flow rate of 20 µl/minute, and then the dissociation reaction was monitored for 3 minutes. After the dissociation reaction, the tip surface was regenerated by adding 20 µl of 10 mmol/l Glycine-HCl buffer (pH 1.5) continuously twice. This cycle was carried out for antibody solutions of various concentrations (50 to 1.85 µg/ml), and a sensorgram at each concentration was obtained. The sensorgram of each antibody was made into a sensorgram of specific reaction by subtracting a sensorgram obtained using a chimeric antibody KM871 for GD3 [*Cancer Immunol. Immunother.*, 36, 373 (1993)] as a negative control.

Figure 12:
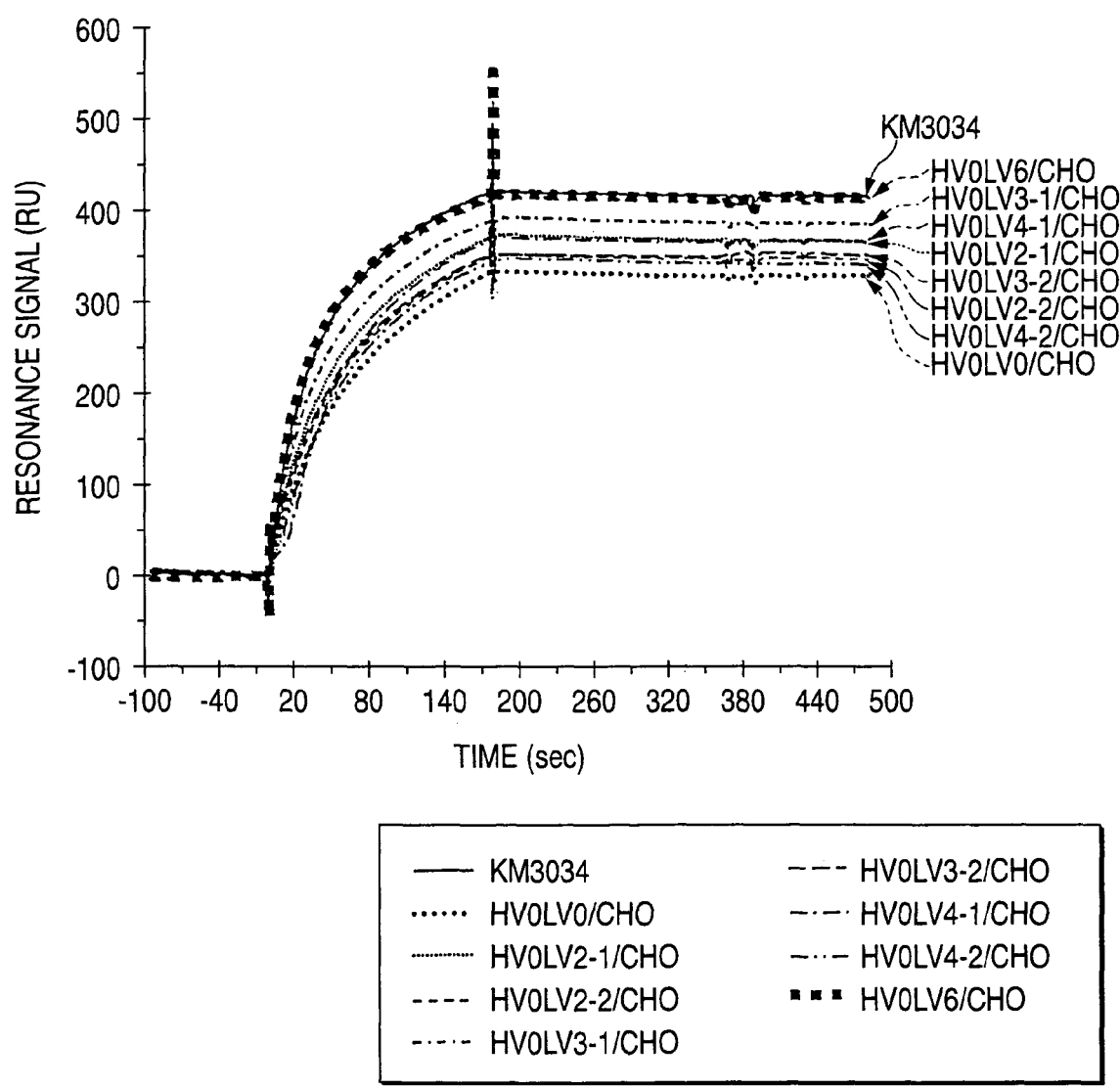
FIG. 12 shows results of BIAcore 2000 measurement of FGF-8 binding activities of anti-FGF-8 chimeric antibody KM3034 and anti-FGF-8 CDR-grafted antibodies HV0LV0/CHO, HV0LV2-1/CHO, HV0LV2-2/CHO, HV0LV3-1/CHO, HV0LV3-2/CHO, HV0LV4-1/CHO, HV0LV4-2/CHO and HV0LV6/CHO. The abscissa and the ordinate show time (seconds) and resonance signal (RU), respectively.

The sensorgram of 16.7 µg/ml of each antibody is shown in FIG. 12. As is apparent from the sensorgram, dissociation was hardly observed at the time of the dissociation reaction of each antibody, so that it was difficult to obtain accurate dissociation constant. Accordingly, the binding activity of various antibodies was carried out by comparing intensity of binding [resonance signal (RU)] at the time of the binding reaction.

As a result, as shown in FIG. 12, the chimeric antibodies KM3034 and HV0LV6/CHO showed the highest binding reaction, followed by HV0LV3-1/CHO, HV0LV4-1/CHO and HV0LV2-1/CHO in this order. On the other hand, HV0LV3-2/CHO, HV0LV2-2/CHO and HV0LV4-2/CHO showed low binding reaction, and HV0LV0/CHO showed the lowest binding reaction. These results coincided with the results using the YB2/0 cell-derived anti-FGF-8 CDR-grafted antibodies described in the item 7 of Example 2.

8. Measurement of Neutralization Activity of Anti-FGF-8 CDR-Grafted Antibodies for FGF-8

Figure 13:
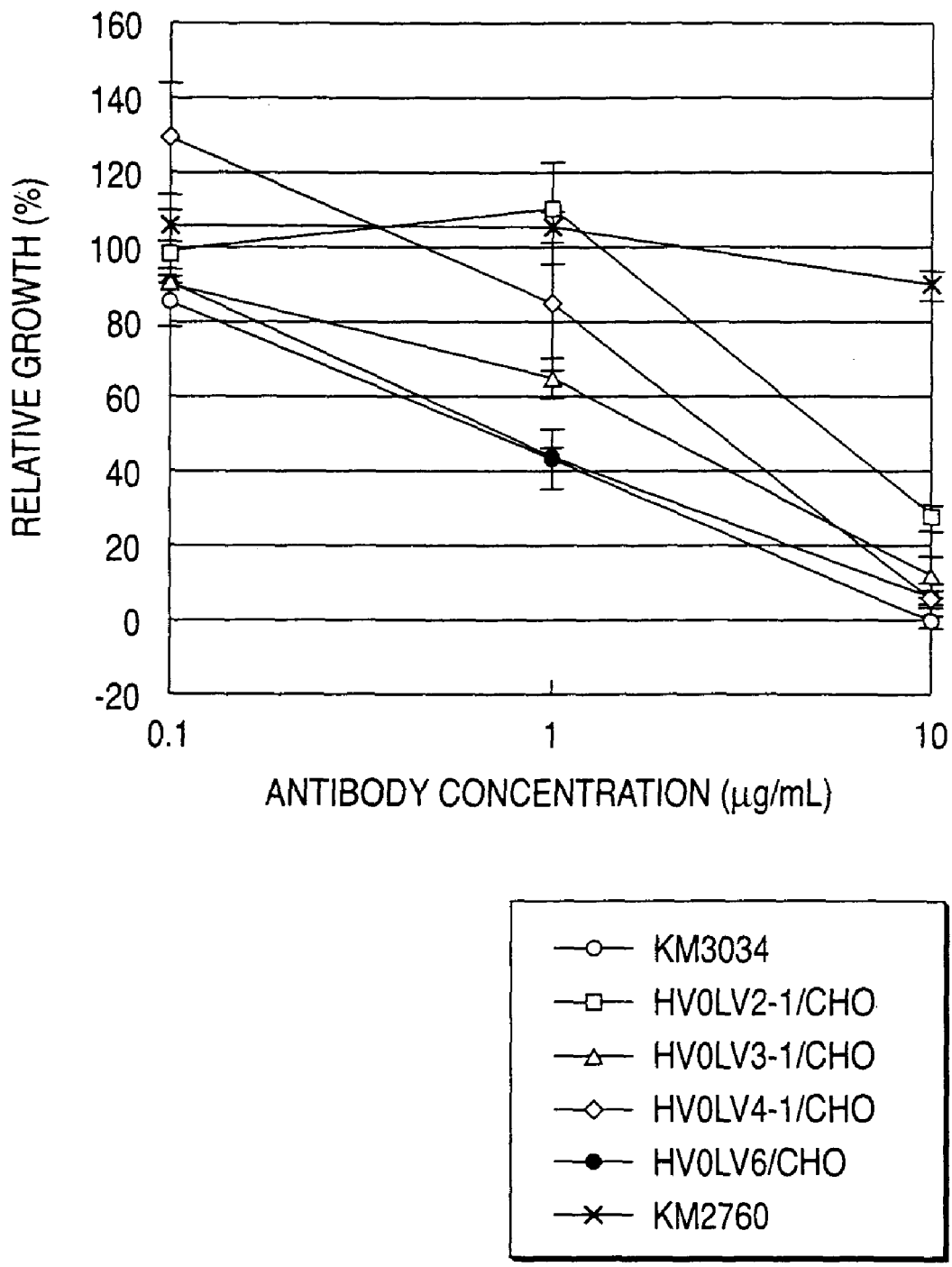
FIG. 13 shows neutralization activities of anti-FGF-8 chimeric antibody KM3034 and anti-FGF-8 CDR-grafted antibodies HV0LV2-1/CHO, HV0LV3-1/CHO, HV0LV4-1/CHO and HV0LV6/CHO on the FGF-8-dependent growth of mouse breast cancer cell line SC-3 cells. The abscissa and the ordinate show antibody concentration (μg/ml) and relative growth (%) when the growth by the addition of FGF-8 alone is defined as 100%, respectively. "○", "□", "Δ", "◇", "●" and "x" indicate activities of KM3034, HV0LV2-1/CHO, HV0LV3-1/CHO, HV0LV4-1/CHO, HV0LV6/CHO and KM2760 as a negative control, respectively.

Evaluation of neutralization activity of the four anti-FGF-8 CDR-grafted antibodies HV0LV6/CHO, HV0LV3-1/CHO, HV0LV4-1/CHO and HV0LV2-1/CHO whose high binding reaction for FGF-8 was confirmed in the item 7 of Example 3 was carried out in accordance with the method described in the item 5 of Example 2. The CHO/DG44 cell-derived anti-FGF-8 chimeric antibody KM3034 obtained in the item 3(1) of Example 1 was used as a positive control, and the chimeric antibody KM2760 for human chemokine CCR4 described in WO 01/64754 as a negative control. The results are shown in FIG. 13. As shown in FIG. 13, the HV0LV6/CHO showed similar FGF-8 neutralization activity to that of the chimeric antibody KM3034, and the HV0LV3-1/CHO showed the next high FGF-8 neutralization activity. The HV0LV4-1/CHO showed a slightly lower FGF-8 neutralization activity than the HV0LV3-1/CHO, and the HV0LV2-1/CHO showed the lowest neutralization activity.

Example 4

Preparation of Anti-FGF-8 CDR-Grafted Antibody having Lower Immunogenicity (2)

It was found from the results of Example 4 that among modifications of the 6 amino acid residues of LV6, modification at position 51 is essential for the activity recovery. Also, it was suggested that modification at position 2 has small effect for the activity recovery by its modification alone, but it contributes to the activity recovery cooperatively by its combination with the 51st position modification. Regarding the modifications at positions 14 and 15, it was suggested also that they contribute to the activity recovery cooperatively by their combination with the modification at position 51. On the other hand, it was suggested that effect of the modification of the 50th position is small. Accordingly, in order to examine which one of the modification at position 2 and the modification at position 14 or 15 has higher effect on the activity recovery, and for examining effect of the modification at position 92, preparation of anti-FGF-8 CDR-grafted antibodies was carried out again.

1. Re-Designing of VL Amino Acid Sequences

Amino acid sequences of two VLs having the following modifications were designed. Each case shows modification from amino acid residues of LV0.

In LV.4-3, 4 residues of Thr at position 14, Pro at position 15, Leu at position 51 and Tyr at position 92 were changed to Ser, Leu, Val and Phe, respectively, which are amino acid residues found in the mouse antibody KM1334.

In LV.3-3, 3 residues of Thr at position 14, Pro at position 15 and Leu at position 51 were changed to Ser, Leu and Val, respectively, which are amino acid residues found in the mouse antibody KM1334.

2. Construction of cDNA Encoding VL

The cDNAs encoding respective anti-FGF-8 CDR-grafted antibody VL amino acid sequences designed in the item 1 of Example 4 were constructed as follows.

(1) Construction of cDNA Encoding LV.4-3

This was constructed in accordance with the method described in the item 2(5) of Example 3. However, the plasmid pKM1334LV2-1 obtained in the item 2(3) of Example 3 was used instead of the plasmid pKM1334LV2-2 and the plasmid pKM1334LV3-2 obtained in the item 2(6) of Example 3 was used instead of the plasmid pKM1334LV6. As a result, a plasmid pKM1334LV4-3 containing a cDNA encoding LV.4-3 was obtained.

(2) Construction of cDNA Encoding LV.3-3

A reaction was carried out by mixing 3 μg of the plasmid pKM1334LV4-3 obtained in the item 2(1) of Example 4 with 10 units of restriction enzyme BamHI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2.5 μg of a BamHI-SpeI fragment of about 3.23 kb.

Next, 3 μg of the plasmid pKM1334LV0 obtained in the item 1(3) of Example 2 was allowed to react with 10 units of restriction enzyme BamHI (manufactured by Takara Shuzo) and 10 units of restriction enzyme SpeI (manufactured by Takara Shuzo) at 37° C. for 1 hour. The reaction solution was fractionated by agarose gel electrophoresis to collect about 0.15 μg of a BamHI-SpeI fragment of about 0.13 kb.

Figure 14:
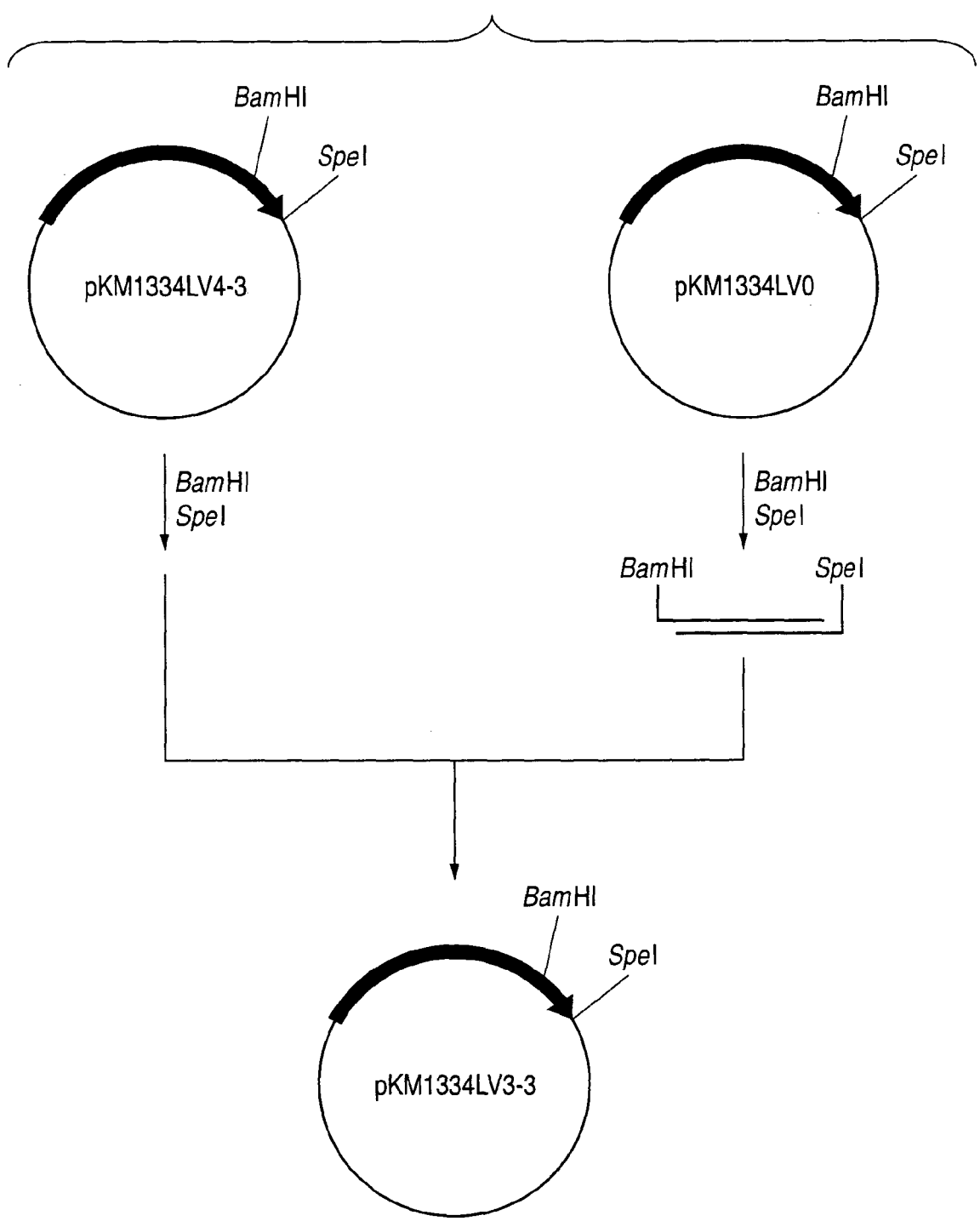
FIG. 14 shows construction steps of plasmid pKM1334LV3-3.

To 10 μl in total volume of sterile water, 0.1 μg of the BamHI-SpeI fragment derived from the plasmid pKM1334LV4-3 and 0.1 μg of the BamHI-SpeI fragment derived from the plasmid pKM1334LV0 each obtained in the above were added and ligated by using Ligation High (manufactured by TOYOBO). E. coli DH5α was transformed by using the thus obtained recombinant plasmid DNA solution to obtain the plasmid pKM1334LV3-3 shown in FIG. 14 containing a cDNA encoding the LV.3-3.

3. Construction of Anti-FGF-8 CDR-Grafted Antibody Expression Vectors

Anti-FGF-8 CDR-grafted antibody expression vectors having various VL cDNAs were constructed by replacing the EcoRI-BsiWI fragment containing the VL cDNA of the expression vector pKANTEX1334HV0LV6 obtained in the item 2 of Example 2 by the EcoRI-BsiWI fragments containing various VL cDNAs constructed in the item 2 of Example 4. Specifically, 2 vectors pKANTEX1334HV0LV4-3 and pKANTEX1334HV0LV3-3 were constructed.

4. Stable Expression of Anti-FGF-8 CDR-Grafted Antibody using CHO/DG44 Cell

Stable expression of various anti-FGF-8 CDR-grafted antibodies in CHO/DG44 cell was carried out in accordance with the method described in the item 2(4) of Example 1 by using various anti-FGF-8 CDR-grafted antibody expression vectors obtained in the item 3 of Example 4.

5. Purification of Anti-FGF-8 CDR-Grafted Antibody

Culturing of CHO/DG44 cell-derived transformants expressing various anti-FGF-8 CDR-grafted antibodies obtained in the item 4 of Example 4 and purification of the anti-FGF-8 CDR-grafted antibodies from culture supernatants were carried out in accordance with the method described in the item 3(1) of Example 1. An antibody derived from a pKANTEX1334HV0LV4-3-introduced transformant was named HV0LV4-3/CHO, and an antibody derived from a pKANTEX1334HV0LV3-3-introduced transformant was named HV0LV3-3/CHO.

6. Analysis of Purified Anti-FGF-8 CDR-Grafted Antibody

SDS-PAGE of various anti-FGF-8 CDR-grafted antibodies obtained in the item 5 of Example 4 was carried out according to the method described in the item 4 of Example 1. As a result, it was confirmed that each antibody was expressed and purified as an antibody molecule of correct structure.

7. Measurement of Binding Activity of Anti-FGF-8 CDR-Grafted Antibodies for FGF-8

The FGF-8 binding activities of the anti-FGF-8 CDR-grafted antibodies HV0LV6/CHO and HV0LV3-1/CHO obtained in the item 5 of Example 3 and the anti-FGF-8 CDR-grafted antibodies HV0LV4-3/CHO and HV0LV3-3/CHO obtained in the item 5 of Example 4 were measured in accordance with the method described in the item 7 of Example 3. The CHO/DG44-derived anti-FGF-8 chimeric antibody KM3034 obtained in the item 3(1) of Example 1 was used as a positive control.

Figure 15:
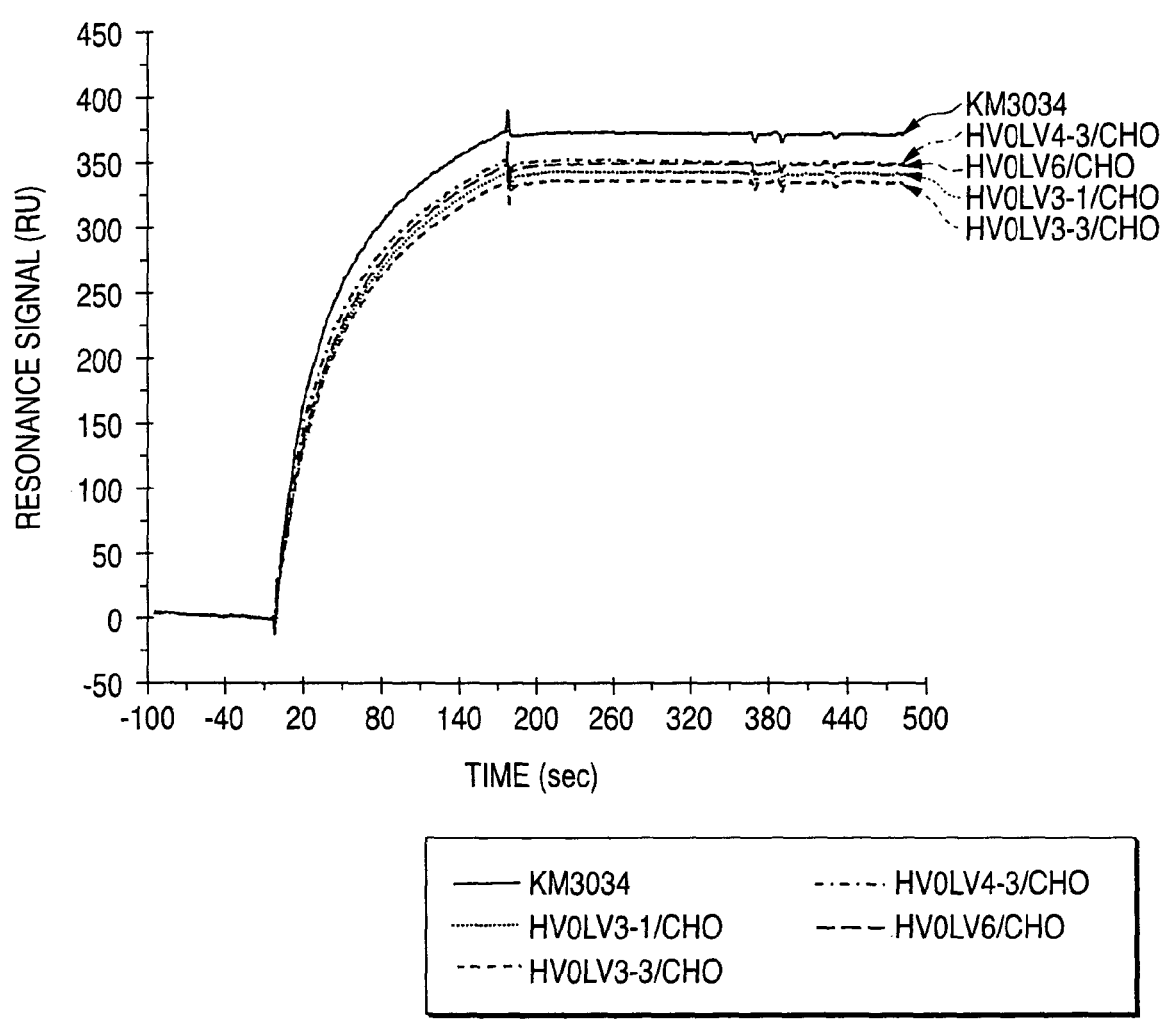
FIG. 15 shows results of BIAcore 2000 measurement of FGF-8 binding activities of anti-FGF-8 chimeric antibody KM3034 and anti-FGF-8 CDR-grafted antibodies HV0LV3-1/CHO, HV0LV3-3/CHO, HV0LV4-3/CHO and HV0LV6/CHO. The abscissa and the ordinate show time (seconds) and resonance signal (RU), respectively.

The sensorgram of 16.7 μg/ml of each antibody is shown in FIG. 15. As is apparent from the sensorgram, dissociation was hardly observed at the time of the dissociation reaction of each antibody, so that it was difficult to obtain accurate dissociation constant. Accordingly, the binding activity of respective antibodies was carried out by comparing intensity of binding [resonance signal (RU)] at the time of the binding reaction. As a result, as shown in FIG. 15, the chimeric antibodies KM3034 showed the highest binding reaction, and HV0LV4-3/CHO showed a binding reaction which was higher than that of HV0LV3-1/CHO and similar to that of HV0LV3-3/CHO. Binding reaction of HV0LV3-3/CHO was lower than that of HV0LV3-1. From the above results, it was suggested that regarding the height of the binding reaction, the modification at position 14 or 15 functions more cooperatively than the modification at position 2, and modification at position 92 is essential for the recovery of the activity.

8. Measurement of Neutralization Activity of Anti-FGF-8 CDR-Grafted Antibody for FGF-8

Evaluation of neutralization activity of the anti-FGF-8 CDR-grafted antibodies HV0LV6/CHO and HV0LV3-1/CHO obtained in the item 5 of Example 3 and the anti-FGF-8

Figure 16:
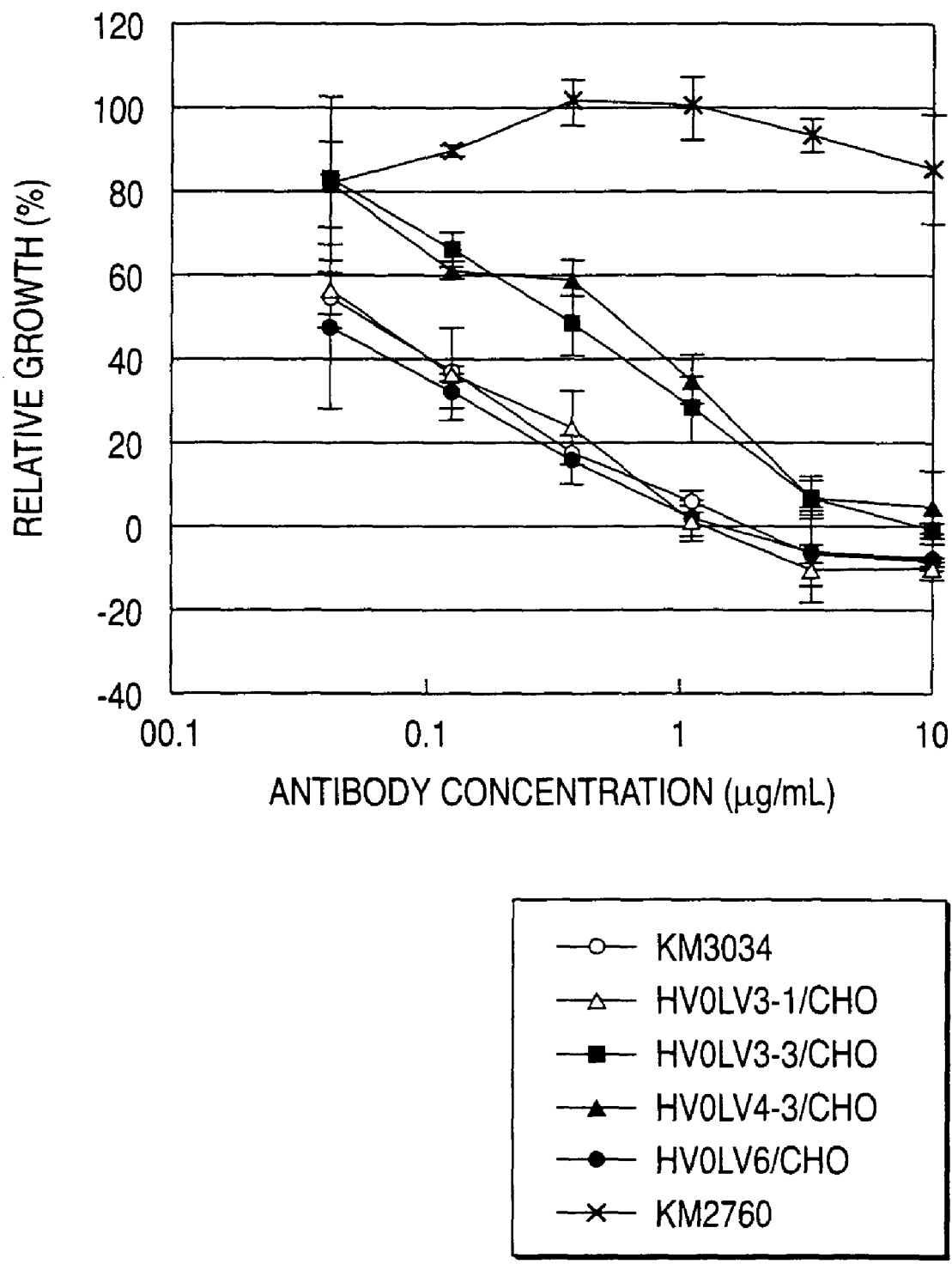
FIG. 16 shows neutralization activities of anti-FGF-8 chimeric antibody KM3034 and anti-FGF-8 CDR-grafted antibodies HV0LV3-1/CHO, HV0LV3-3/CHO, HV0LV4-3/CHO and HV0LV6/CHO on the FGF-8-dependent growth of mouse breast cancer cell line SC-3 cells. The abscissa and the ordinate show antibody concentration (μg/ml) and relative growth (%) when the growth by the addition of FGF-8 alone is defined as 100%, respectively. "○", "Δ", "■", "▲", "●" and "x" indicate activities of KM3034, HV0LV3-1/CHO, HV0LV3-3/CHO, HV0LV4-3/CHO, HV0LV6/CHO and KM2760 as a negative control, respectively.

CDR-grafted antibodies HV0LV4-3/CHO and HV0LV3-3/CHO obtained in the item 5 of Example 4 was carried out in accordance with the method described in the item 5 of Example 2. The CHO/DG44 cell-derived anti-FGF-8 chimeric antibody KM3034 obtained in the item 3(1) of Example 1 was used as a positive control, and the chimeric antibody KM2760 for human chemokine CCR4 described in WO 01/64754 as a negative control. The results are shown in FIG. 16. As shown in FIG. 16, HV0LV6/CHO and HV0LV3-1/CHO showed similar FGF-8 neutralization activity to that of the chimeric antibody KM3034. On the other hand, HV0LV4-3/CHO and HV0LV3-3/CHO showed almost the same neutralization activity, and the activity was about ½ of that of the chimeric antibody KM3034. Neutralization activity of HV0LV3-1/CHO and HV0LV4-3/CHO showed no correlation with the height of the binding reaction by BIAcore, and it was suggested that the amino acid residue at position 2 and amino acid residues at positions 14 and 15 have independent influences on the binding activity for FGF-5 and the FGF-8 neutralization activity for cells.

Based on the above results of respective evaluations, the CHO/DG44 cell-derived CDR-grafted antibody HV0LV6/CHO which showed high binding reaction and FGF-8 neutralization activity similar to those of the chimeric antibody KM3034 was named KM8034, and the CHO/DG44 cell-derived transformed cell clone highly expressing KM8034 was named KM8034 in the same manner. Also, the CHO/DG44 cell-derived CDR-grafted antibody HV0LV4-3/CHO which showed high binding reaction similar to that of KM8034 was named KM8035, and the CHO/DG44 cell-derived transformed cell line highly expressing KM8035 was named KM8035 in the same manner. The VL amino acid sequence LV.4-3 of KM8035 is shown in SEQ ID NO:38. Furthermore, the transformed cell line KM8035 has been deposited on Jun. 20, 2002, as FERM BP-8082 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan). In addition, the CHO/DG44 cell-derived CDR-grafted antibody HV0LV3-1/CHO which showed a high binding reaction similar to that of KM8034 was named KM8036, and the CHO/DG44 cell-derived transformed cell line highly expressing KM8036 was named KM8036 in the same manner. The amino acid sequence LV0.3-1 of VL of KM8036 is shown in SEQ ID NO:39. Also, the transformed cell line KM8036 has been deposited on Jun. 20, 2002, as FERM BP-8083 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

Since the anti-FGF-8 CDR-grafted antibody KM8034 shows high binding reaction and FGF-8 neutralization activity similar to those of the chimeric antibody KM3034, and the immunogenicity in human is reduced than the chimeric antibody, its therapeutic effects higher than the chimeric antibody is expected. Although there is a possibility that the binding activity and FGF-8 neutralization activity of the anti-FGF-8 CDR-grafted antibodies KM8036 and KM8035 are slightly reduced in comparison with KM8034, amino acid residues of the V region FR derived from the mouse antibody KM1334 are 3 residues and 4 residues, respectively, so that further reduced immunogenicity than the KM8034 is expected.

INDUSTRIAL APPLICABILITY

The present invention provides a humanized antibody or the antibody fragment thereof which specifically reacts with FGF-8 which is considered to be a growth factor of prostate cancer, breast cancer, ovarian cancer and the like and which further inhibits the function of FGF-8.

Free Text of Sequence Listings:

SEQ ID NO:11—Explanation of artificial sequence: Synthetic DNA
SEQ ID NO:12—Explanation of artificial sequence: Synthetic DNA
SEQ ID NO:13—Explanation of artificial sequence: Synthetic DNA
SEQ ID NO:14—Explanation of artificial sequence: Synthetic DNA
SEQ ID NO:20—Explanation of artificial sequence: Synthetic DNA
SEQ ID NO:21—Explanation of artificial sequence: Synthetic DNA
SEQ ID NO:22—Explanation of artificial sequence: Synthetic DNA
SEQ ID NO:23—Explanation of artificial sequence: Synthetic DNA
SEQ ID NO:24—Explanation of artificial sequence: Synthetic DNA
SEQ ID NO:25—Explanation of artificial sequence: Synthetic DNA
SEQ ID NO:26—Explanation of artificial sequence: Synthetic DNA
SEQ ID NO:27—Explanation of artificial sequence: Synthetic DNA
SEQ ID NO:28—Explanation of artificial sequence: Synthetic DNA
SEQ ID NO:29—Explanation of artificial sequence: Synthetic DNA
SEQ ID NO:30—Explanation of artificial sequence: Synthetic DNA
SEQ ID NO:31—Explanation of artificial sequence: Synthetic DNA
SEQ ID NO:32—Explanation of artificial sequence: Synthetic DNA
SEQ ID NO:33—Explanation of artificial sequence: Synthetic DNA
SEQ ID NO:34—Explanation of artificial sequence: Synthetic DNA
SEQ ID NO:35—Explanation of artificial sequence: Synthetic DNA
SEQ ID NO:36—Explanation of artificial sequence: Synthetic DNA
SEQ ID NO:37—Explanation of artificial sequence: Synthetic DNA

The invention claimed is:

1. A human complementarity determining region (CDR)-grafted antibody which specifically reacts with fibroblast growth factor-8 (FGF-8) and inhibits biological function of FGF-8, or a FGF-8-binding antibody fragment thereof,
wherein a heavy chain variable region (VH) of the antibody comprises the amino acid sequence represented by SEQ ID NO:16, and
wherein a light chain variable region (VL) of the antibody comprises the amino acid sequence represented by SEQ ID NO:19.

2. A human complementarity determining region (CDR)-grafted antibody which specifically reacts with fibroblast growth factor-8 (FGF-8) and inhibits biological function of FGF-8, or a FGF-8-binding antibody fragment thereof,
wherein a heavy chain variable region (VH) of the antibody comprises the amino acid sequence represented by SEQ ID NO:16, and
wherein a light chain variable region (VL) of the antibody comprises the amino acid sequence represented by SEQ ID NO:38.

3. A human complementarity determining region (CDR)-grafted antibody which specifically reacts with fibroblast growth factor-8 (FGF-8) and inhibits biological function of FGF-8, or a FGF-8-binding antibody fragment thereof,
wherein a heavy chain variable region (VH) of the antibody comprises the amino acid sequence represented by SEQ ID NO:16, and
wherein a light chain variable region (VL) of the antibody comprises the amino acid sequence represented by SEQ ID NO:39.

4. An isolated DNA encoding the variable region of the human CDR-grafted antibody or the FGF-8-binding antibody fragment thereof according to any of claims 1, 2 or 3.

5. A recombinant vector comprising the DNA according to claim 4.

6. An isolated transformed host cell comprising the recombinant vector according to claim 5.

7. A process for producing an antibody or a FGF-8-binding antibody fragment thereof, which comprises culturing the transformed host cell according to claim 6 in a medium to prepare and accumulate the human CDR-grafted antibody or the FGF-8-binding antibody fragment in the culture, and recovering the human CDR-grafted antibody or the FGF-8-binding antibody fragment thereof from the culture.

8. A composition which comprises at least one selected from the human CDR-grafted antibody and the FGF-8-binding antibody fragment thereof according to any of claims 1, 2 or 3, and a pharmaceutically acceptable carrier.

* * * * *